(12) United States Patent
Mwale et al.

(10) Patent No.: US 10,202,420 B2
(45) Date of Patent: Feb. 12, 2019

(54) METHODS AND COMPOSITIONS FOR TREATMENT OF CARTILAGE AND DISC TISSUE PATHOLOGIES

(71) Applicant: THE ROYAL INSTITUTION FOR ADVANCEMENT OF LEARNING/MCGILL UNIVERSITY, Montreal, Québec (CA)

(72) Inventors: Fackson Mwale, Montreal (CA); John Antoniou, Westmount (CA); Lisbet Haglund, Montreal (CA); Peter J. Roughley, Beaconsfield (CA); Rahul Gawri, Toronto (CA); Laura M. Epure, Pierrefonds (CA); Michael P. Grant, Sainte-Catherine (CA)

(73) Assignee: THE ROYAL INSTITUTION FOR THE ADVANCEMENT OF LEARNING/MCGILL UNIVERSITY, Montreal (CA)

( * ) Notice: Subject to any disclaimer, the term of this patent is extended or adjusted under 35 U.S.C. 154(b) by 351 days.

(21) Appl. No.: 14/914,452

(22) PCT Filed: Aug. 27, 2014

(86) PCT No.: PCT/CA2014/000656
§ 371 (c)(1),
(2) Date: Feb. 25, 2016

(87) PCT Pub. No.: WO2015/027322
PCT Pub. Date: Mar. 1, 2016

(65) Prior Publication Data
US 2016/0207959 A1    Jul. 21, 2016

Related U.S. Application Data

(60) Provisional application No. 61/975,329, filed on Apr. 4, 2014, provisional application No. 61/870,394, filed on Aug. 27, 2013.

(51) Int. Cl.
| | |
|---|---|
| *C07K 7/06* | (2006.01) |
| *A61K 35/32* | (2015.01) |
| *C07K 7/08* | (2006.01) |
| *A61K 35/28* | (2015.01) |
| *A61K 38/00* | (2006.01) |

(52) U.S. Cl.
CPC ............ *C07K 7/06* (2013.01); *A61K 35/28* (2013.01); *A61K 35/32* (2013.01); *C07K 7/08* (2013.01); *A61K 38/00* (2013.01)

(58) Field of Classification Search
None
See application file for complete search history.

(56) References Cited

U.S. PATENT DOCUMENTS

2016/0207959 A1*   7/2016   Mwale

FOREIGN PATENT DOCUMENTS

| WO | WO-02/083860 A2 | 10/2002 |
|---|---|---|
| WO | WO-2015/027322 A1 | 3/2015 |

OTHER PUBLICATIONS

Extended European Search Report for European Application No. 14839126.1, dated Mar. 17, 2017 (7 pages).
Gawri, Rahul, thesis: "Link-N Peptide: A potential therapeutic agent for biological repair of early degenerated Human Intervertebral Discs," Division of Surgical Research, McGill University, 2013.
Liu et al., "An N-terminal peptide from link protein can stimulate biosynthesis of collagen by human articular cartilage," Arch Biochem Biophys. 378(1):116-22 (2000).
Liu et al., "An N-terminal peptide from link protein stimulates synthesis of cartilage proteoglycans," Biochem Soc Trans. 25(3):427S (1997).
Gawri et al., "Link N is cleaved by human annulus fibrosus cells generating a fragment with retained biological activity," J Orthop Res. 32(9):1189-97 (2014).
International Search Report for International Application No. PCT/CA2014/000656, dated Dec. 4, 2014 (9 pages).

* cited by examiner

*Primary Examiner* — Michael D Burkhart
(74) *Attorney, Agent, or Firm* — Clark & Elbing LLP

(57) ABSTRACT

An isolated polypeptide comprising a peptide selected from: i) DHX$_1$SDNYT, wherein X$_1$ is L or H (SEQ ID NO:3); ii) a conservative variant of i) iii) a fragment of i) or ii); wherein the conservative variant and/or fragment retains biological activity and the peptide is 15 or less amino acids as well as recombinant cells, and uses thereof.

13 Claims, 33 Drawing Sheets
Specification includes a Sequence Listing.

Fig. 1
Figure 1 a
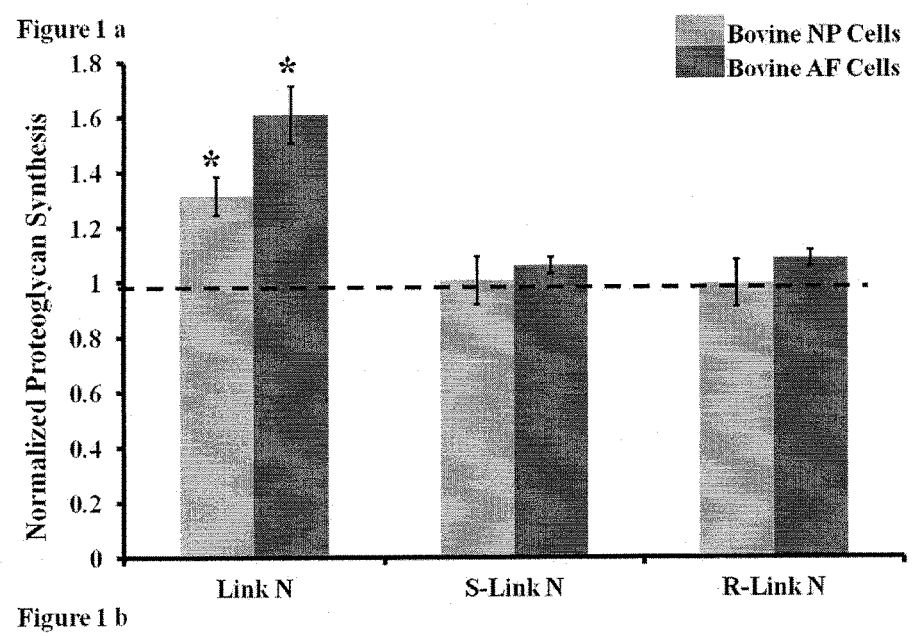
Figure 1 b
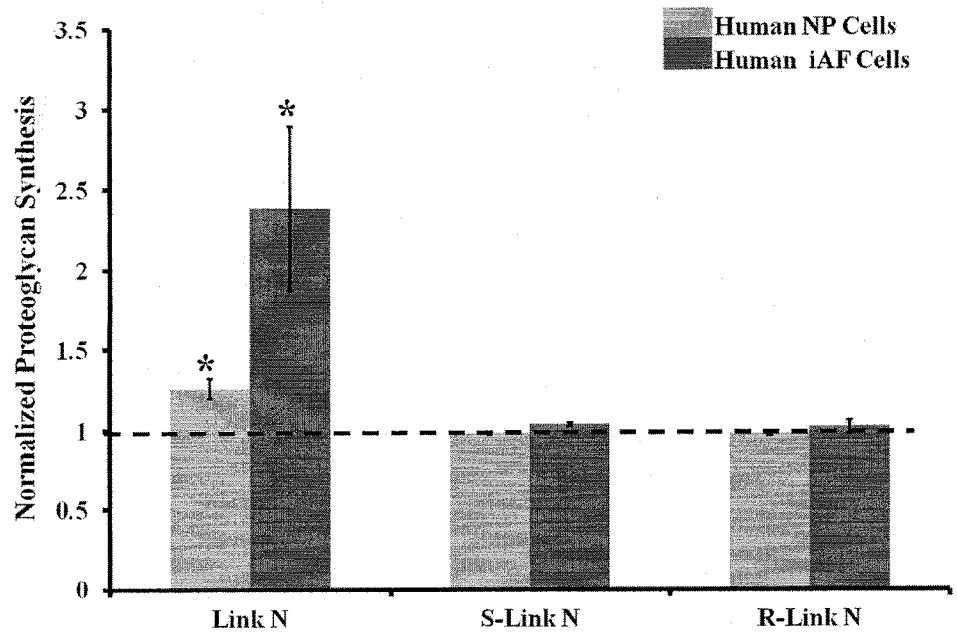

Fig. 4
Figure 4 a
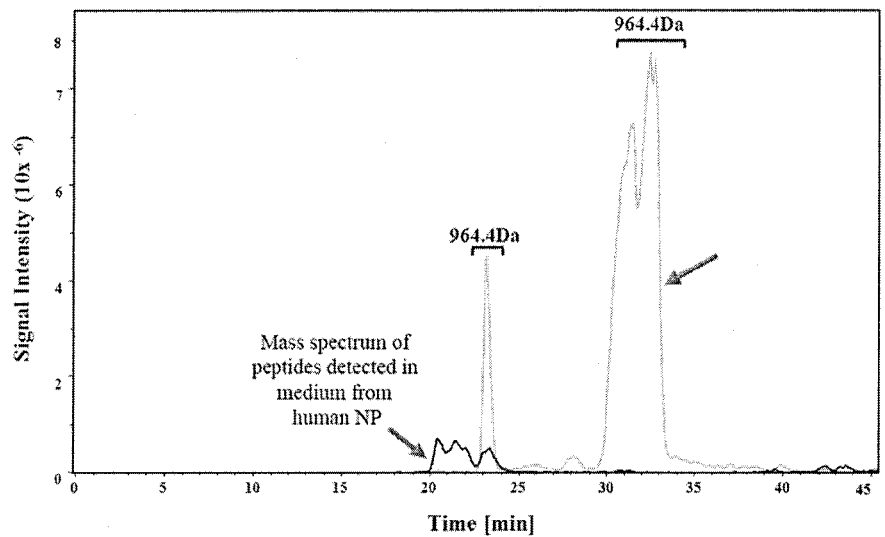
Figure 4 b
M+ Mol. Mass 964.401kDa
$$[\text{D-H-L-S-D-N-Y-T-L-D-H-D-R-A-I-H}]$$
— 1st Possible Sequence (Correct)
---- 2nd Possible Sequence
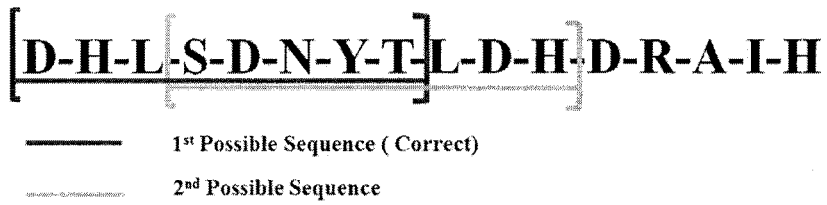
Figure 4 c
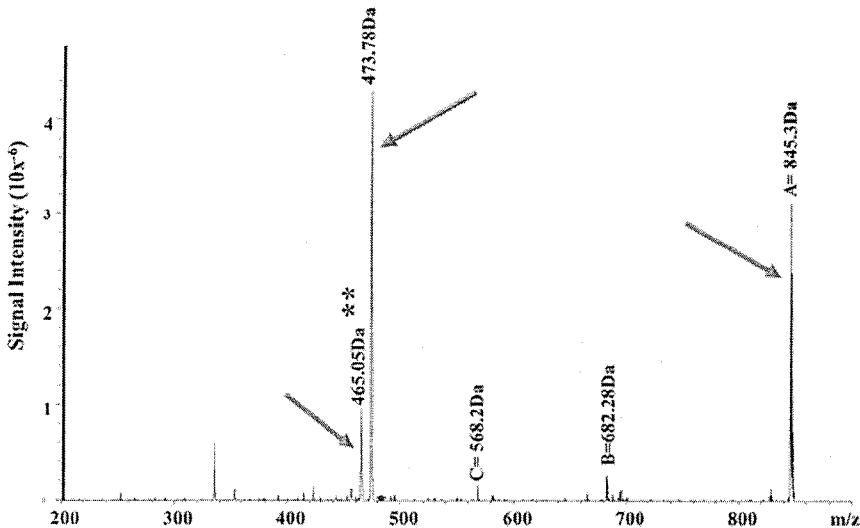

Fig. 5
Figure 5 a
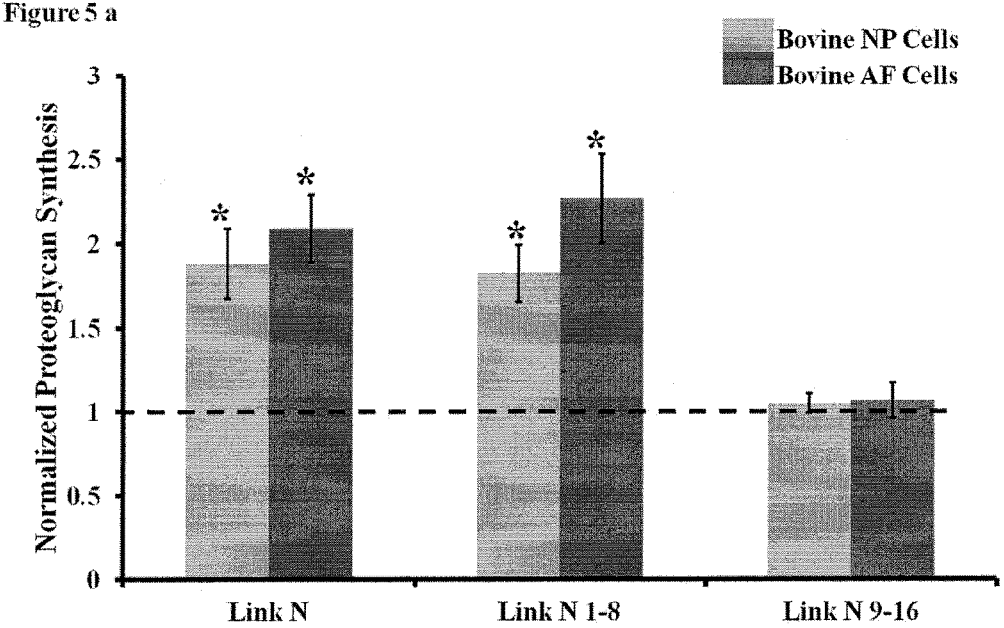
Figure 5 b
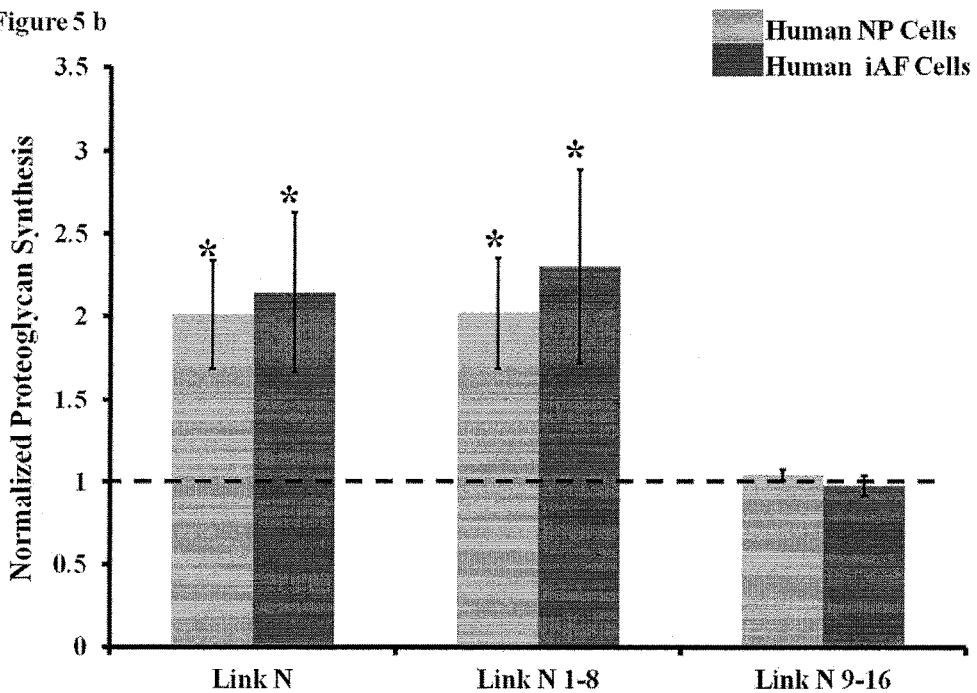

Fig.6
A) Link N 1-16
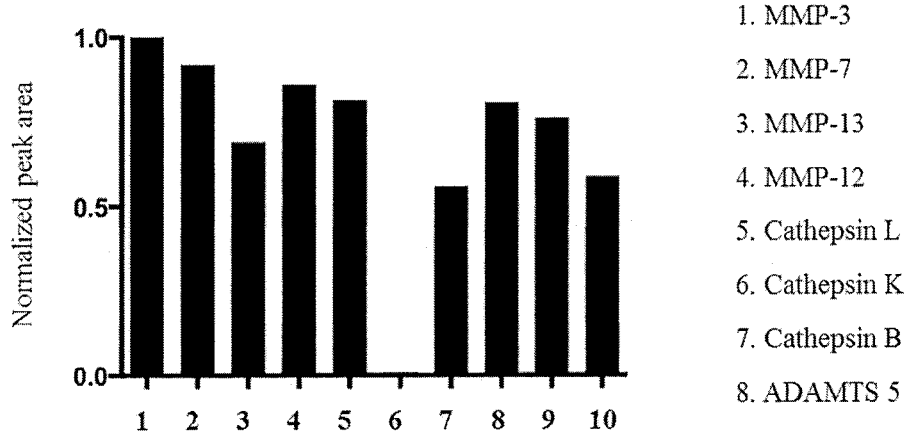
1. MMP-3
2. MMP-7
3. MMP-13
4. MMP-12
5. Cathepsin L
6. Cathepsin K
7. Cathepsin B
8. ADAMTS 5
9. ADAMTS 4
10. HTRA1
B) Link N 1-8
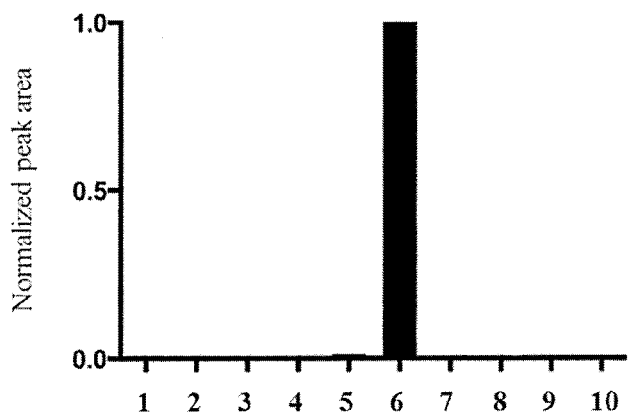
C) Link N 9-16
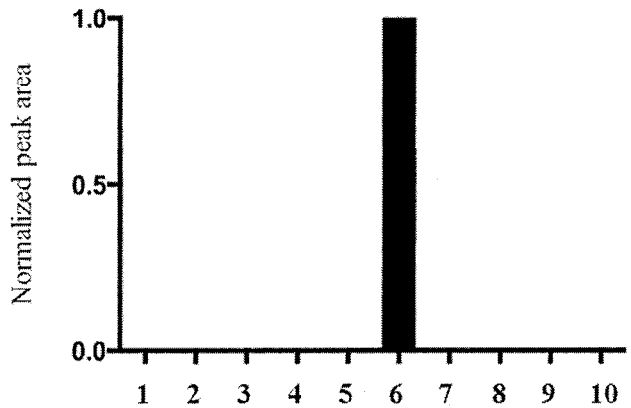

Fig. 10 MMP-13 and Col X expression in OA explants

A) NFκB activation decrease in dose response pattern in normal chondrocytes

B) NFκB activation decrease in dose response pattern in OA chondrocytes

Fig. 14
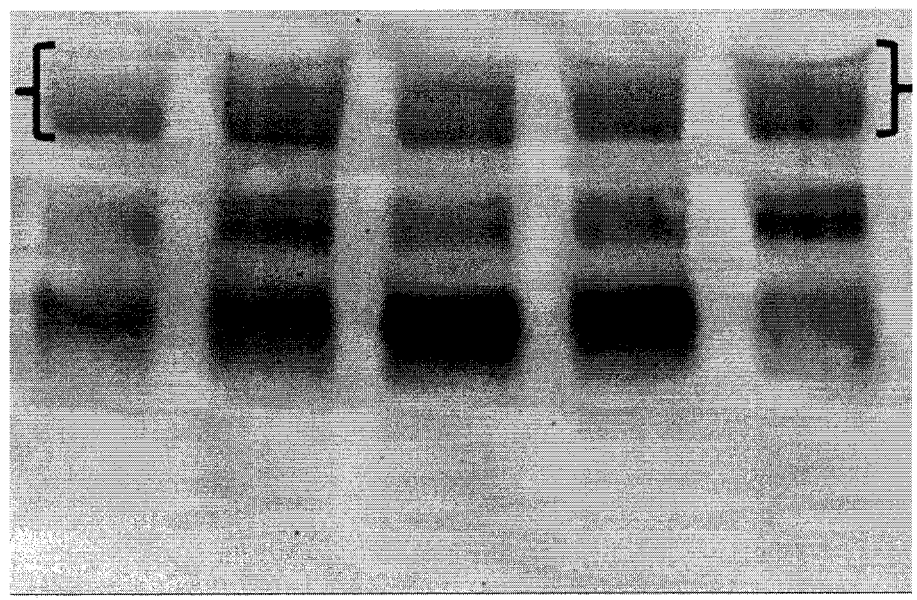
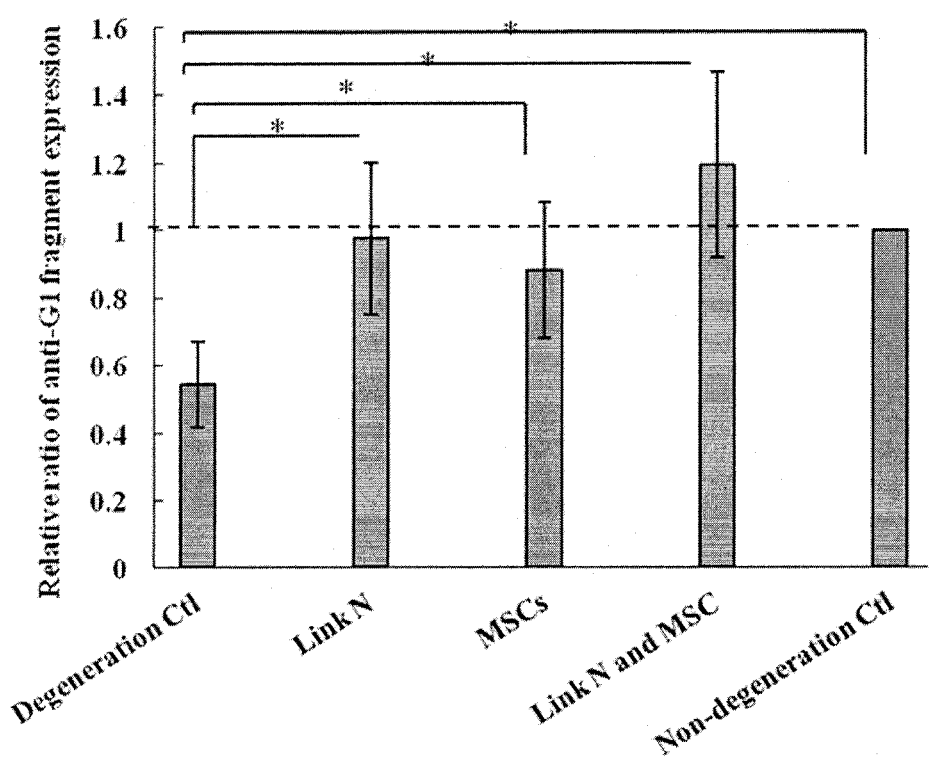

Effect of Link N 1-8 on proteoglycan synthesis, aggrecan and type II collagen expression in bovine disc organ culture

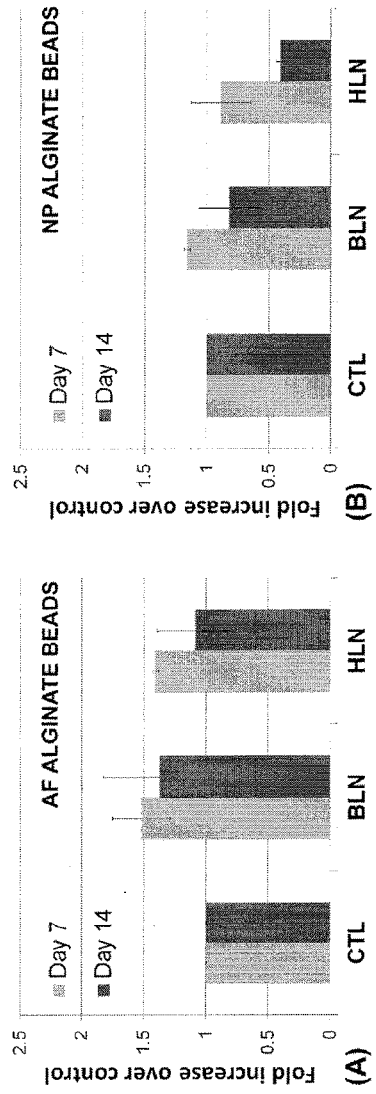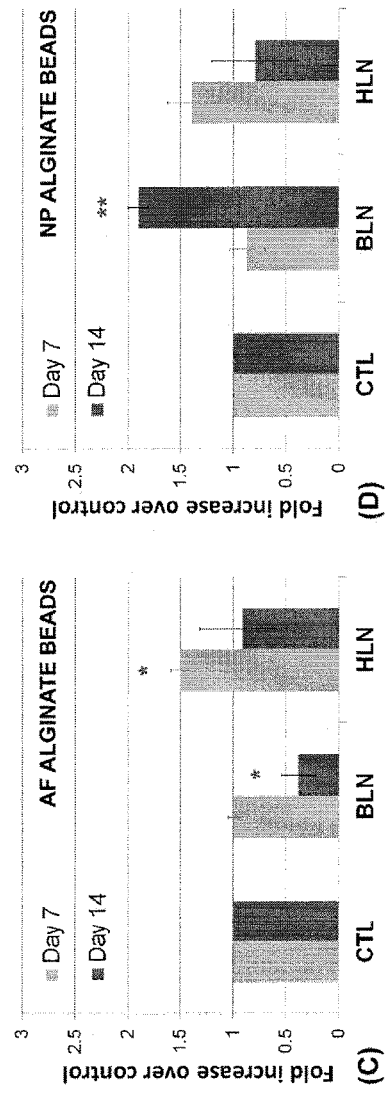
Fig. 24

NGF gene expression and NGF release in grade 4 human AF cells.

Link N reduced Substance P release from injured bovine IVD

SEQUENCE LISTING

```
<160> NUMBER OF SEQ ID NOS: 32

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Leu or His

<400> SEQUENCE: 1

Asp His Xaa Ser Asp Asn Tyr Thr
1               5
```

-continued

```
<210> SEQ ID NO 2
<211> LENGTH: 8
<212> TYPE: PRT
<213> ORGANISM: Homo sapiens

<400> SEQUENCE: 2

Asp His Leu Ser Asp Asn Tyr Thr
1               5

<210> SEQ ID NO 3
<211> LENGTH: 8
<212> TYPE: PRT
<213> ORGANISM: Bos taurus

<400> SEQUENCE: 3

Asp His His Ser Asp Asn Tyr Thr
1               5

<210> SEQ ID NO 4
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Leu or His
<220> FEATURE:
<221> NAME/KEY: MOD_RES
<222> LOCATION: (9)..(9)
<223> OTHER INFORMATION: Xaa is Leu or Val
<220> FEATURE:
<221> NAME/KEY: MOD_RES
<222> LOCATION: (14)..(14)
<223> OTHER INFORMATION: Xaa is Ala or Val

<400> SEQUENCE: 4

Asp His Xaa Ser Asp Asn Tyr Thr Xaa Asp His Asp Arg Xaa Ile
1               5                   10                  15

<210> SEQ ID NO 5
<211> LENGTH: 16
<212> TYPE: PRT
<213> ORGANISM: Bos taurus

<400> SEQUENCE: 5

Asp His His Ser Asp Asn Tyr Thr Val Asp His Asp Arg Val Ile His
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is any amino acid, optionally Leu, His,
      Arg, Gln
<220> FEATURE:
<221> NAME/KEY: MOD_RES
<222> LOCATION: (4)..(4)
<223> OTHER INFORMATION: Xaa is Ser or Leu
<220> FEATURE:
<221> NAME/KEY: MOD_RES
<222> LOCATION: (5)..(5)
<223> OTHER INFORMATION: Xaa is Asp, Ser, or Asn
<220> FEATURE:
<221> NAME/KEY: MOD_RES
```

```
<222> LOCATION: (6)..(6)
<223> OTHER INFORMATION: Xaa is Asn or Asp
<220> FEATURE:
<221> NAME/KEY: MOD_RES
<222> LOCATION: (7)..(7)
<223> OTHER INFORMATION: Xaa is Tyr or Ser
<220> FEATURE:
<221> NAME/KEY: MOD_RES
<222> LOCATION: (8)..(8)
<223> OTHER INFORMATION: Xaa is Thr or Tyr
<220> FEATURE:
<221> NAME/KEY: MOD_RES
<222> LOCATION: (9)..(9)
<223> OTHER INFORMATION: Xaa is Leu, Val or Thr
<220> FEATURE:
<221> NAME/KEY: MOD_RES
<222> LOCATION: (10)..(10)
<223> OTHER INFORMATION: Xaa is any amino acid, optionally Asp, Gly, Asn
      or Pro
<220> FEATURE:
<221> NAME/KEY: MOD_RES
<222> LOCATION: (11)..(11)
<223> OTHER INFORMATION: Xaa is His, Tyr or Pro
<220> FEATURE:
<221> NAME/KEY: MOD_RES
<222> LOCATION: (13)..(13)
<223> OTHER INFORMATION: Xaa is Arg or Gln
<220> FEATURE:
<221> NAME/KEY: MOD_RES
<222> LOCATION: (14)..(14)
<223> OTHER INFORMATION: Xaa is Ala, Val or Asp
<220> FEATURE:
<221> NAME/KEY: MOD_RES
<222> LOCATION: (15)..(15)
<223> OTHER INFORMATION: Xaa is Ile or Arg
<220> FEATURE:
<221> NAME/KEY: MOD_RES
<222> LOCATION: (16)..(16)
<223> OTHER INFORMATION: Xaa is His or Val

<400> SEQUENCE: 6

Asp His Xaa Xaa Xaa Xaa Xaa Xaa Xaa Xaa Xaa Asp Xaa Xaa Xaa Xaa
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is any amino acid, optionally Leu, His,
      Arg, Gln
<220> FEATURE:
<221> NAME/KEY: MOD_RES
<222> LOCATION: (5)..(5)
<223> OTHER INFORMATION: Xaa is Asp, Ser or Asn
<220> FEATURE:
<221> NAME/KEY: MOD_RES
<222> LOCATION: (9)..(9)
<223> OTHER INFORMATION: Xaa is Leu, Val or Thr
<220> FEATURE:
<221> NAME/KEY: MOD_RES
<222> LOCATION: (10)..(10)
<223> OTHER INFORMATION: Xaa is any amino acid, optionally Asp, Gly, Asn
      or Pro

<400> SEQUENCE: 7

Asp His Xaa Ser Xaa Asn Tyr Thr Xaa Xaa His Asp Arg Val Ile His
1               5                   10                  15

<210> SEQ ID NO 8
<211> LENGTH: 15
```

-continued

```
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Leu or His
<220> FEATURE:
<221> NAME/KEY: MOD_RES
<222> LOCATION: (9)..(9)
<223> OTHER INFORMATION: Xaa is Leu or Val
<220> FEATURE:
<221> NAME/KEY: MOD_RES
<222> LOCATION: (14)..(14)
<223> OTHER INFORMATION: Xaa is Ala or Val

<400> SEQUENCE: 8

Asp His Xaa Ser Asp Asn Tyr Thr Xaa Asp His Asp Arg Xaa Ile
1               5                   10                  15

<210> SEQ ID NO 9
<211> LENGTH: 15
<212> TYPE: PRT
<213> ORGANISM: Homo sapiens

<400> SEQUENCE: 9

Asp His Leu Ser Asp Asn Tyr Thr Leu Asp His Asp Arg Ala Ile
1               5                   10                  15

<210> SEQ ID NO 10
<211> LENGTH: 15
<212> TYPE: PRT
<213> ORGANISM: Bos taurus

<400> SEQUENCE: 10

Asp His His Ser Asp Asn Tyr Thr Val Asp His Asp Arg Val Ile
1               5                   10                  15

<210> SEQ ID NO 11
<211> LENGTH: 16
<212> TYPE: PRT
<213> ORGANISM: Equus caballus

<400> SEQUENCE: 11

Asp His Arg Ser Asp Asn Tyr Thr Leu Asp His Asp Arg Val Ile His
1               5                   10                  15

<210> SEQ ID NO 12
<211> LENGTH: 16
<212> TYPE: PRT
<213> ORGANISM: Oryctolagus cuniculus

<400> SEQUENCE: 12

Asp His Gln Ser Asn Asn Tyr Thr Leu Gly His Asp Arg Val Ile His
1               5                   10                  15

<210> SEQ ID NO 13
<211> LENGTH: 16
<212> TYPE: PRT
<213> ORGANISM: Canis lupus

<400> SEQUENCE: 13

Asp His His Ser Asp Asn Tyr Thr Leu Asn Tyr Asp Arg Val Ile His
1               5                   10                  15

<210> SEQ ID NO 14
```

```
<211> LENGTH: 16
<212> TYPE: PRT
<213> ORGANISM: Mus musculus

<400> SEQUENCE: 14

Asp His His Leu Ser Asp Ser Tyr Thr Pro Pro Asp Gln Asp Arg Val
1               5                   10                  15

<210> SEQ ID NO 15
<211> LENGTH: 16
<212> TYPE: PRT
<213> ORGANISM: Homo sapiens

<400> SEQUENCE: 15

Asp His Leu Ser Asp Asn Tyr Thr Leu Asp His Asp Arg Ala Ile His
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Synthetic Construct

<400> SEQUENCE: 16

His Ile Ala Arg Asp His Asp Leu Thr Tyr Asn Asp Ser Leu His Asp
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Synthetic Construct

<400> SEQUENCE: 17

Asp Leu Asn Arg Ala His Leu His Ile Asp Tyr His Thr Asp Ser Asp
1               5                   10                  15

<210> SEQ ID NO 18
<211> LENGTH: 8
<212> TYPE: PRT
<213> ORGANISM: Homo sapiens

<400> SEQUENCE: 18

Leu Asp His Asp Arg Ala Ile His
1               5

<210> SEQ ID NO 19
<211> LENGTH: 7
<212> TYPE: PRT
<213> ORGANISM: Homo sapiens

<400> SEQUENCE: 19

Asp His Leu Ser Asp Asn Tyr
1               5

<210> SEQ ID NO 20
<211> LENGTH: 6
<212> TYPE: PRT
<213> ORGANISM: Homo sapiens

<400> SEQUENCE: 20

Asp His Leu Ser Asp Asn
1               5
```

<210> SEQ ID NO 21
<211> LENGTH: 5
<212> TYPE: PRT
<213> ORGANISM: Homo sapiens

<400> SEQUENCE: 21

Asp His Leu Ser Asp
1               5

<210> SEQ ID NO 22
<211> LENGTH: 20
<212> TYPE: DNA
<213> ORGANISM: Artificial Sequence
<220> FEATURE:
<223> OTHER INFORMATION: Synthetic Construct

<400> SEQUENCE: 22
aatgcccagg actaccagtg                                        20

<210> SEQ ID NO 23
<211> LENGTH: 20
<212> TYPE: DNA
<213> ORGANISM: Artificial Sequence
<220> FEATURE:
<223> OTHER INFORMATION: Synthetic Construct

<400> SEQUENCE: 23
cccttctcat gccagatcat                                        20

<210> SEQ ID NO 24
<211> LENGTH: 20
<212> TYPE: DNA
<213> ORGANISM: Artificial Sequence
<220> FEATURE:
<223> OTHER INFORMATION: Synthetic Construct

<400> SEQUENCE: 24
caatgcactg gtctgaatgg                                        20

<210> SEQ ID NO 25
<211> LENGTH: 20
<212> TYPE: DNA
<213> ORGANISM: Artificial Sequence
<220> FEATURE:
<223> OTHER INFORMATION: Synthetic Construct

<400> SEQUENCE: 25
ctaggagaca gtgcccgaag                                        20

<210> SEQ ID NO 26
<211> LENGTH: 20
<212> TYPE: DNA
<213> ORGANISM: Artificial Sequence
<220> FEATURE:
<223> OTHER INFORMATION: Synthetic Construct

<400> SEQUENCE: 26
gggaccatat gctctcctga                                        20

<210> SEQ ID NO 27
<211> LENGTH: 20
<212> TYPE: DNA
<213> ORGANISM: Artificial Sequence
<220> FEATURE:
<223> OTHER INFORMATION: Synthetic Construct

<400> SEQUENCE: 27
aatgctggtg aggatggaag                                                    20

<210> SEQ ID NO 28
<211> LENGTH: 20
<212> TYPE: DNA
<213> ORGANISM: Artificial Sequence
<220> FEATURE:
<223> OTHER INFORMATION: Synthetic Construct

<400> SEQUENCE: 28
ggagcgattt gtctgggtta                                                    20

<210> SEQ ID NO 29
<211> LENGTH: 20
<212> TYPE: DNA
<213> ORGANISM: Artificial Sequence
<220> FEATURE:
<223> OTHER INFORMATION: Synthetic Construct

<400> SEQUENCE: 29
cgctgagcca gtcagtgtag                                                    20

<210> SEQ ID NO 30
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is any amino acid, optionally Leu, His,
      Arg, Gln
<220> FEATURE:
<221> NAME/KEY: MOD_RES
<222> LOCATION: (4)..(4)
<223> OTHER INFORMATION: Xaa is Ser or Leu
<220> FEATURE:
<221> NAME/KEY: MOD_RES
<222> LOCATION: (5)..(5)
<223> OTHER INFORMATION: Xaa is  Asp, Ser or Asn
<220> FEATURE:
<221> NAME/KEY: MOD_RES
<222> LOCATION: (6)..(6)
<223> OTHER INFORMATION: Xaa is Asn or Asp
<220> FEATURE:
<221> NAME/KEY: MOD_RES
<222> LOCATION: (7)..(7)
<223> OTHER INFORMATION: Xaa is Tyr or Ser
<220> FEATURE:
<221> NAME/KEY: MOD_RES
<222> LOCATION: (8)..(8)
<223> OTHER INFORMATION: Xaa is Thr or Tyr

<400> SEQUENCE: 30

Asp His Xaa Xaa Xaa Xaa Xaa Xaa
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is any amino acid, optionally Leu, His,
      Arg, Gln
<220> FEATURE:

```
<221> NAME/KEY: MOD_RES
<222> LOCATION: (5)..(5)
<223> OTHER INFORMATION: Xaa is Asp, Ser or Asn

<400> SEQUENCE: 31

Asp His Xaa Ser Xaa Asn Tyr Thr
1               5

<210> SEQ ID NO 32
<211> LENGTH: 16
<212> TYPE: PRT
<213> ORGANISM: Homo sapiens

<400> SEQUENCE: 32

Asp His Leu Ser Asp Asn Tyr Thr Leu Asp Leu Asp Arg Ala Ile His
1               5                   10                  15
```

METHODS AND COMPOSITIONS FOR TREATMENT OF CARTILAGE AND DISC TISSUE PATHOLOGIES

This is a Patent Cooperation Treaty application which claims the benefit of 35 U.S.C. § 119 based on the priority of U.S. Provisional Patent Applications No. 61/870,394, filed Aug. 27, 2013 and 61/975,329, filed Aug. 4, 2014, which are incorporated herein by reference in their entirety.

FIELD

The disclosure relates to methods and compositions for the treatment of cartilage and disc disorders and particularly to methods and compositions using Link N fragments for the treatment of cartilage and disc disorders such as arthritis and intervertebral disc degeneration.

BACKGROUND

The intervertebral discs (IVDs) link adjacent vertebrae within the spine. They are composed of the peripheral annulus fibrosus (AF) and the central nucleus pulposus (NP). The AF is a fibrosus tissue with concentric lamellae rich in collagen fibrils (1). The NP has a more amorphous consistency, with collagen fibrils that have a random orientation and a high content of aggrecan that give it a gelatinous appearance and provides for the ability to resist compressive loads. Aggrecan is a large proteoglycan with numerous glycosaminoglycan (GAG) chains attached to its core protein, which in the NP provides the osmotic properties needed to counter the effects of compression.

Mechanisms that contribute to degenerative changes in the disc lead to biochemical alterations in the composition and structure of extracellular matrix due to both depleted synthesis and increased degradation, with aggrecan being particularly susceptible to proteolytic damage and loss. Aging, poor nutrition, biomechanical (2-5), biochemical (6-10) and genetic influences (11-14) are associated with increased IVD degeneration. During degeneration, loss of GAG content in the NP occurs, changing it from a gelatinous structure to a fibrotic texture as it becomes more collagenous, and fissures appear in both the NP and AF (15,16). This is commonly associated with low back pain, possibly due to the nerve ingrowth and loss of disc height, which are facilitated by proteoglycan depletion (17). Currently, there is no medical treatment for IVD degeneration, ultimately leaving surgical excision of the damaged tissue, insertion of a cage or prosthesis to restore the IVD space, and vertebral bone fusion as the only offered option. While this may provide relatively good clinical short-term results (18) in pain relief, in many instances it also alters spine biomechanics leading to subsequent adjacent-level disc degeneration.

Biological repair of the degenerating IVD would be preferable to surgical excision.

Disc degeneration starts early in life and progresses with increasing age (48, 49). This process is characterised by a phenotypic change of the resident cells and results in increased production of inflammatory cytokines (50, 51). A number of cytokines have been linked to disc degeneration; IL-1β and TNF-α were the first to be described, but additional candidates such as IL-6 and IL-8 have more recently been described especially in animal models (17). Studies of human discs from degenerate/herniated specimens showed, in addition to IL-13 and TNF-α, increased levels of IL-2, IL-4, IL-10, IL-12 and IL-17 when compared to healthy control (52). The exact mechanism leading to increased cytokine production is unclear. Multiple internal and external cues could influence cytokine production, such as heredity, mechanical loading, oxygenation, or the presence of inflammatory cells (17). In addition, accumulation of specific matrix fragmentation products may activate Toll-like receptors and thereby induce cytokine production.

Inflammatory cytokines are known to induce protease production, which subsequently leads to structural failure and loss of IVD height due to degradation of the extracellular matrix (ECM), including aggrecan and collagen (53). Although proteases are responsible for fragmentation and breakdown of important components of the ECM, they also have significant roles in normal remodeling of the disc. Cathepsin K activity, along with matrix metalloproteinase (MMP) proteolysis of aggrecan, has been suggested to be mainly a process of normal tissue remodeling in the disc (54, 55). However, matrix metalloproteinases (MMP1, 2, 3, 7, 9, 13), aggrecanases (ADAMTS4, 5), and cathepsins (cathepsins D and L) are all elevated during disc degeneration (56, 9). In addition, the serine protease HTRA1, is thought to play a central role in disc degeneration as elevated levels of HTRA1 and its degradation of CHAD correlated to the degree of disc degeneration (10, 57).

Degradation of the protein and proteoglycan content of the nucleus pulposus (NP) can result in loss of disc height and the weight bearing capacity of the disc. In the final stages of disc degradation fissures in the annular ring occur, leading to extrusion of NP material and pain due to compression of nerves. A repair strategy of the painful degenerate disc requires production of ECM components and down regulation of proteinase activity in the inflammatory milieu. These properties are associated with several growth factors such as TGF-β and BMP 7 (58-61). However, the use of growth factors in clinical practice is limited by their high cost and potential side effects.

Osteoarthritis (OA) is a chronic degenerative joint disorder that affects millions of people. It is characterized by the destruction of articular cartilage due to an imbalance in the anabolic and catabolic activities of chondrocytes. Articular cartilage is an avascular connective tissue, covering the bony parts of diarthrodial joints allowing the frictionless motion of the joint, by absorbing and dissipating load. These properties are related to the composition and structure of its extracellular matrix (ECM). It is composed of collagen fibrils, proteoglycans (predominantly aggrecan), noncollagenous proteins and a high content of water. The only cell type in articular cartilage is the chondrocyte, and is responsible for the synthesis and maintenance of the extracellular matrix.

During osteoarthritis (OA), characterized by degradation of articular cartilage and inflammation of the synovial membrane, this equilibrium is disrupted due to increased degradation of collagens and proteoglycans from the matrix and depleted synthesis of molecules. Cartilage responds to a complex multitude of autocrine and paracrine (anabolic and catabolic) factors that regulate gene expression and protein synthesis in chondrocytes.

Matrix degradation is mediated by matrix metalloproteinases (MMPs) and ADAMTS-4 and -5, induced by Interleukin-1beta (IL-1β) the major cytokine implicated in OA. Other cytokines that have been implicated in OA pathogenesis include tumor necrosis factor-alpha (TNF-α), IL-6, other common c-chain cytokines such as IL-2, IL-7, IL-15, and IL-21, and chemokines. These factors produced by synovial cells and chondrocytes results in the upregulation of members of the matrix metalloproteinase (MMP) and a disintegrin and metalloproteinase with thrombospondin motifs (ADAMTS) families of enzymes. MMPs are involved in ECM turnover and cartilage degeneration. Aging, obesity, and joint injuries are associated with increased OA. It is characterized by progressive cellular and molecular changes in all joint tissues, including articular cartilage, subchondral bone, synovium, ligaments, and peri-articular muscles. There are currently no therapies that reverse or repair cartilage degradation in OA patients.

There is general agreement that since inflammatory processes play a fundamental role in the pathogenesis of various rheumatic diseases, such as, OA and rheumatoid arthritis (RA) selective inhibition of inflammatory activities is vital for therapy and that the family of NF-κB transcription factors play a prominent role in this process. Thus several studies have been directed towards the pharmacologic modulation of the NF-κB pathways using non-steroidal anti-inflammatory drugs, corticosteroids, nutraceuticals, antisense DNA therapy, RNA interference and anti-rheumatic drugs.

Link N is a 16 amino acid sequence that has been shown to increase proteoglycan synthesis and production of other matrix components by IVD cells (29, 34). It has also been shown to increase disc height in a rabbit disc puncture degeneration model, thereby demonstrating a regenerative potential also in vivo (31). This naturally occurring peptide represents the N-terminal region of the link protein that stabilizes proteoglycan aggregates in both disc and cartilage, and is generated by MMPs during tissue turnover in vivo. Link N interacts with the Bone Morphogenetic Protein (BMP) Type 11 Receptor and activates Smad1/5 signaling in cultured rabbit IVD cells (33).

Fragments of Link N have been tested. Wang et al. reported that the stimulatory effect of Link N was lost when they evaluated a number of shorter Link N-derived peptides (33) including a peptide spanning amino acid residues 1-12.

SUMMARY

An aspect of the disclosure includes an isolated polypeptide comprising a peptide selected from:
  i) DHX$_1$SDNYT, wherein X$_1$ is L or H (SEQ ID NO:1);
  ii) a conservative variant of i)
  iii) a fragment of i) or ii);
wherein the conservative variant and/or fragment retains biological activity and the peptide is 15 or less amino acids.

In an embodiment, the isolated polypeptide comprises a peptide sequence consisting of: 1) DHLSDNYT (SEQ ID NO:2); and/or a conservative variant thereof that retains biological activity or 2) DHHSDNYT (SEQ ID NO:3) or a conservative variant thereof that retains biological activity In another embodiment, the isolated polypeptide comprises a peptide selected from:
i) DHX$_1$SDNYTX$_2$DHDR X$_3$I, wherein X$_1$ is L or H, X$_2$ is L or V and X$_3$ is A or V (SEQ ID NO: 4);
ii) a conservative variant of i); and
iii) a fragment of i) or ii)
wherein the conservative variant and/or fragment retains biological activity.

Another aspect includes an isolated nucleic acid that encodes a polypeptide comprising a Link N fragment peptide.

A further aspect includes a vector comprising 1) a nucleic acid that encodes a polypeptide comprising a Link N fragment peptide; or 2) a Link N fragment polypeptide.

A further aspect is a recombinant cell expressing a polypeptide comprising a Link N fragment peptide.

Yet another aspect is a composition comprising a polypeptide comprising a Link fragment polypeptide, a recombinant cell expressing a polypeptide comprising a Link N fragment peptide, Methods for making and using said products are also described.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the present disclosure will now be described in relation to the drawings in which:

FIG. 1: Proteoglycan synthesis by bovine or human disc cells. Synthesis was estimated by evaluating $^{35}SO_4$ incorporation, after 48 h in the presence of Link N (1 µg/mL), scrambled S-Link N (1 µg/mL), reversed R-Link N (1 µg/mL) or media without peptide supplementation. Relative proteoglycan expression is shown in bovine nucleus pulposus (NP) and annulus fibrosus (AF) cells (a), and in human nucleus pulposus (NP) and inner annulus fibrosus (iAF) cells (b). Data are expressed as a mean±SD, of the ratio relative to incorporation by control cells exposed to medium alone (n=3). Values where p≤0.05 (*) were taken as significant.

FIG. 4: Mass spectrometry of processed Link N. (a) Mass spectrum of peptides detected in medium from human NP (black) and AF (grey) cells. Fragmented Link N with a mass of 964.4 Da is indicated in the graph. The 964.4 Da peptide eluted from the column in 2 different regions, with retention times of around 23 and 32 min. (b) Schematic illustration of the two possible Link N fragments of 964.4 Da, Link N 1-8 (highlighted in dark gray) and Link N 4-11 (highlighted in light gray). (c) The amino acid sequence of the generated 964.4 Da fragment was identified by tandem MS. The sequence was confirmed by evaluating the generated fragmentation products of the peptide. Major detected peaks are A [(845.3 Da) DHLSDNY (SEQ ID NO: 19) (+1)], B [(682.28 Da) DHLSDN (SEQ ID NO: 20) (+1)] and C [(568.2 Da) DHLSD (SEQ ID NO: 21) (+1)], masses that can only be generated by the 1-8 sequence.

FIG. 5: Proteoglycan synthesis by bovine and human cells in response to Link N fragments. Synthesis was estimated by evaluating $^{35}SO_4$ incorporation after 48 h in the presence of Link N (1 µg/mL), Link N 1-8 (0.5 µg/mL), Link N 9-16 (0.5 µg/mL) or media without peptide supplementation. Relative proteoglycan expression is shown in bovine nucleus pulposus (NP) and annulus fibrosus (AF) (a), and human nucleus pulposus (NP) and inner annulus fibrosus (iAF) cells (b). Data are expressed as mean±SD, of the ratio relative to incorporation by control cells exposed to medium alone (n=3). Values where $p \leq 0.05$ (*) were taken as significant.

FIG. 6: Exposure of Link 1-16 to proteinases described to be involved in disc degeneration. Link 1-16 was exposed to MMPs 3, 7, 12, 13, Cathepsins L, K, and B, ADAMTS 4, 5 and HTRA1 and the peak area intensity was quantified using mass spectrometry. A, Relative intensity of the intact Link N 1-16, peptide. B, Relative intensity of the Link N 1-8, peptide. C Relative intensity of the Link N 9-16, peptide.

FIG. 14. Analysis of aggrecan core protein in the discs. Immunoblotting and semi-quantitative analysis of intact aggrecan core protein with a molecular weight of about 320 kDa in degeneration control, Link N treated, MSCs treated, both Link N and MSCs treated, and no degeneration control discs. The results are represented as mean±SD of seven discs from different bovine tails. (*p<0.05)

FIG. 24: Changes in aggrecan ADAMTS-4 and ADAMTS-5 gene expression. Changes in (A, B) ADAMTS-4 and (C, D) ADAMTS-5 gene expression of the annulus fibrosus (AF) and nucleus pulposus (NP) bovine cells beaded in 1.2% alginate at 1 week and 2 weeks after incubation in medium supplemented with either 1 µg/ml bovine (BLN) or human Link N (HLN). Gene expression was measured by RT-PCR. 18S rRNA was used as a housekeeping gene and served to normalize the results. The values are expressed as a ratio of the gene expression of cells exposed to Link N relative to that of cells exposed to medium alone (CTL). ($*p<0.05$, $**p<0.001$).

DETAILED DESCRIPTION OF THE DISCLOSURE

I. Definitions

Figure 2:
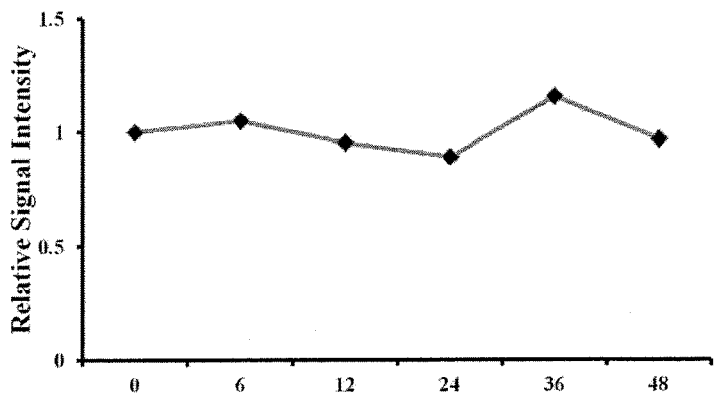
FIG. 2: Stability of Link-N in culture medium. Link N was incubated for 48 h at 37° C., 5% $CO_2$ in culture medium and the peak intensity of the intact peptide was followed by mass spectrometry. Aliquots were analyzed at 6, 12, 24, 36 and 48 h. Data is plotted as ratio relative to signal intensity at time 0. The plot is one out of three representative experiments.

The term "cartilage cell" as used herein means chondrocyte lineage cells, for example found in cartilage tissue and which can be used to produce cartilage tissue.

The term "chondrocyte lineage cells" as used herein means chondrocyte cells and cells that are cytochemically similar and express chondrocyte markers, including for example Sox9 and collagen II, and behave as chondrocyte cells. The chondrocyte cells can be articular cartilage lineage chondrocytes or hypertrophic lineage chondrocytes that are capable of hypertrophy.

The term "cartilage tissue" as used herein means cartilage tissue and tissue that is histologically similar and expresses cartilage markers, for example collagen II and aggrecan, and behaves as cartilage, including articular cartilage tissue and/or growth plate cartilage like tissue.

The term "conservative variant" as used herein means a Link N polypeptide fragment comprising one or more conservative amino acid substitutions.

A "conservative amino acid substitution" as used herein, is one in which one amino acid residue is replaced with another amino acid residue without abolishing the peptide's desired properties. Suitable conservative amino acid substitutions can be made by substituting amino acids with similar hydrophobicity, polarity, and R-chain length for one another. Examples of conservative amino acid substitution include:

| Conservative Substitutions | |
|---|---|
| Type of Amino Acid | Substitutable Amino Acids |
| Hydrophilic | Ala, Pro, Gly, Glu, Asp, Gln, Asn, Ser, Thr |
| Sulphydryl | Cys |
| Aliphatic | Val, Ile, Leu, Met |
| Basic | Lys, Arg, His |
| Aromatic | Phe, Tyr, Trp |

The term "culturing" as used herein incubating and/or passaging cells in an adherent, suspension or 3D cell and/or organ culture. The 3D cell or organ culture can comprise a culture in which cells are cultured in or on a 3-dimensional scaffold.

The term "disc cell" as used herein means cells of the NP or AF cell lineage.

The terms "enriching" or "enriched" as used herein mean that the yield (fraction) of cells of one type is increased by at least about 10%, at least about 20%, at least about 30%, at least about 40%, at least about 50% or at least about 60% over the fraction of cells of that type in the starting culture or preparation. Enriching and partially purifying can be used interchangeably.

The population of cells can be enriched using different methods such as methods based on markers such as cell surface markers (e.g. FACS sorting etc).

As used herein, the term "express" refers to the transcription of a polynucleotide or translation of a polypeptide in a cell, such that levels of the molecule are measurably higher in a cell that has been contacted with or exposed to the molecule (e.g. the Link N fragment) than they are in a cell that has not been contacted or exposed to the molecule. Methods to measure the expression of a molecule are well known to those of ordinary skill in the art, and include without limitation, Northern blotting, RT-PCR, in situ hybridization, Western blotting, and immunostaining such as FACS.

The term "hybridize" refers to the sequence specific non-covalent binding interaction with a complementary nucleic acid. The hybridization is conducted under at least moderately stringent conditions. In a preferred embodiment, the hybridization is under high stringency conditions. Appropriate stringency conditions which promote hybridization are known to those skilled in the art, or can be found in Current Protocols in Molecular Biology, John Wiley & Sons, N.Y. (1989), 6.3.1 6.3.6. For example, 6.0× sodium chloride/sodium citrate (SSC) at about 45° C. for 15 minutes, followed by a wash of 2.0×SSC at 50° C. for 15 minutes may be employed. The stringency may be selected based on the conditions used in the wash step. For example, the salt concentration in the wash step can be selected from a high stringency of about 0.2×SSC at 50° C. for 15 minutes. In addition, the temperature in the wash step can be at high stringency conditions, at about 65° C. for 15 minutes.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature ($Tm=81.5°$ C.$-16.6$ (Log 10 [Na+])$+0.41$(% (G+C)$-600/l$), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% sequence identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm−5° C. based on the above equation, followed by a wash of 0.2×SSC/0.1% SDS at 60° C. for 15 minutes. Moderately stringent hybridization conditions include a washing step in 3×SSC at 42° C. for 15 minutes. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1-6.3.6 and in: Sambrook et al., Molecular Cloning, a Laboratory Manual, Cold Spring Harbor Laboratory Press, 2000, Third Edition.

The term "sequence identity" as used herein refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present application. BLAST protein searches can be performed with the XBLAST program parameters set, e.g., to score-50, wordlength=3 to obtain amino acid sequences homologous to a protein molecule described herein. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). The percent identity between two sequences can be determined using techniques similar to those described above, with or without allowing gaps. In calculating percent identity, typically only exact matches are counted. In an embodiment, the isolated nucleic acids are useful as primers.

The term "isolated" as used herein refers to a component (e.g. polypeptide, nucleic acid, recombinant cell, induced cell) hat has been removed and separated from a mixed or heterogeneous milieu comprising the component. For example with respect to a polypeptide, the term "isolated polypeptide" refers to a proteinaceous agent, such as a peptide, polypeptide or protein, which is substantially free of cellular material or culture medium when produced recombinantly, or chemical precursors, or other chemicals, when chemically synthesized. The term "polypeptide" as used herein refers to a polymer consisting a number of amino acid residues bonded together in a chain and can include polymers comprising naturally occurring amino acids as well as modified bases.

With respect to a nucleic acid means a polymer of A, G, T, C and or modified residues, such as DNA, RNA and cDNA substantially free of cellular material or culture medium when produced by recombinant DNA techniques, or chemical precursors, or other chemicals when chemically synthesized. An "isolated nucleic acid" is also substantially free of sequences which naturally flank the nucleic acid (i.e. sequences located at the 5' and 3' ends of the nucleic acid) from which the nucleic acid is derived. The term "nucleic acid" is intended to include DNA and RNA and can be either double stranded or single stranded.

With respect to an isolated population of cells refers to a population of cells that has been removed and separated from a mixed or heterogeneous population of cells. In some embodiments, an isolated population is a substantially pure population of cells as compared to the heterogeneous population from which the cells were isolated or enriched from.

The term "Link N" as used herein means naturally occurring 16 amino acid peptide cleaved from Link protein by MMP and includes human link N having sequence DHLSDNYTLDHDRAIH (SEQ ID NO: 15) and bovine Link N having sequence DHHSDNYTVDHDRVIH (SEQ ID NO: 5). It is produced in both articular and intervertebral discs and promotes aggrecan/collagen synthesis by disc (NP and AF) and articular cartilage (chondrocyte) cells.

There term "Link N fragment" as used herein means a polypeptide comprising a peptide selected from i) DHX$_1$SDNYT, wherein X$_1$ is L or H (SEQ ID NO:1); ii) a conservative variant of i) or iii) a fragment of i) or ii); wherein the conservative variant and/or fragment retains biological activity and the peptide is 15 amino acids or less. The Link N fragment can for example be a polypeptide having a sequence selected from any one of SEQ ID NOs 1-6, a conservative variant thereof and/or a fragment thereof that retains biological activity.

The term "mesenchymal stem cell" or MSC as used herein refers to a cell with the capacity, under different conditions, to differentiate to more than one differentiated mesenchymal cell type. MSC include induced mesenchymal stem cells and non-induced stem cells.

The term "substantially pure", with respect to a particular cell population, refers to a population of cells that is at least about 65%, preferably at least about 75%, at least about 85%, more preferably at least about 90%, and most preferably at least about 95% pure, with respect to the cells making up a total cell population.

The term "subject" as used herein includes all members of the animal kingdom including mammals, preferably humans.

The terms "treat", "treating", "treatment", etc., as applied to an isolated cell, include subjecting the cell to any kind of process or condition or performing any kind of manipulation or procedure on the cell. As applied to a subject, the terms refer to providing medical or surgical attention, care, or management to a subject.

The term "treatment" as used herein as applied to a subject, refers to an approach aimed at obtaining beneficial or desired results, including clinical results and includes medical procedures and applications including for example pharmaceutical interventions, surgery, radiotherapy and naturopathic interventions as well as test treatments for treating cartilage and/or disc tissue pathologies. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. Treatment can include for example, administering the isolated Link N fragment polypeptide to a subject or implanting cells or transplanting tissue treated with the isolated Link N fragment polypeptide and/or recombinant cell expressing said polypeptide. As used herein, the terms "administering", "implanting" and "transplanting" are used interchangeably in the context of delivering isolated polypeptides, cells, tissues and/or products described herein into a subject, by a method or route which results in at least partial localization of the introduced cells at a desired site. The cells can be implanted directly to a vertebrae or joint, or alternatively be administered by any appropriate route which results in delivery to a desired location in the subject.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

The term "consisting" and its derivatives, as used herein, are intended to be closed ended terms that specify the presence of stated features, elements, components, groups, integers, and/or steps, and also exclude the presence of other unstated features, elements, components, groups, integers and/or steps.

Further, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

More specifically, the term "about" means plus or minus 0.1 to 50%, 5-50%, or 10-40%, 10-20%, 10%-15%, preferably 5-10%, most preferably about 5% of the number to which reference is being made As used in this specification and the appended claims, the singular forms "a", "an" and "the" include plural references unless the content clearly dictates otherwise. Thus for example, a composition containing "a compound" includes a mixture of two or more compounds. It should also be noted that the term "or" is generally employed in its sense including "and/or" unless the content clearly dictates otherwise.

The definitions and embodiments described in particular sections are intended to be applicable to other embodiments herein described for which they are suitable as would be understood by a person skilled in the art.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about".

Further, the definitions and embodiments described are intended to be applicable to other embodiments herein described for which they are suitable as would be understood by a person skilled in the art. For example, in the passages herein, different aspects of the invention are defined in more detail. Each aspect so defined can be combined with any other aspect or aspects unless clearly indicated to the contrary. In particular, any feature indicated as being preferred or advantageous can be combined with any other feature or features indicated as being preferred or advantageous.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

III. Methods and Products

As described herein, it has been found that a fragment of Link N comprising the first 8 amino acids induces and restores extracellular proteoglycan levels in organ cultures and further induces proteoglycan and collagen II synthesis is disc cells and cartilage cells, including in an inflammatory milieu. For example, as demonstrated in Example 3 the GAG content significantly increased compared to the control when osteoarthritic explants were treated with Link N in the presence of IL-1β. Western blot analysis revealed that this also led to a decrease in the quantities of the active form of MMP-13 when compared to IL-1β alone. The quantity of extractable type II collagen was also increased when explants from OA cartilage were treated with Link N, in the presence of IL-1β. Link N significantly inhibited IL-1β stimulated P-P65(NF-kB) in chondrocytes from normal and OA patients.

Further it is demonstrated that bovine link N (BLN) also induces proteoglycan and collagen II synthesis in disc cells as does human link N (HLN).

Link N is a 16 amino acid peptide. Prior to the present disclosure, it was not known whether fragments of Link N existed and/or were active. For example Wang et al (33) reported that a link N fragment comprising the first, 12 amino acids of Link N did not have activity.

An aspect includes an isolated polypeptide (referred to herein as a Link N fragment or Link N fragment polypeptide) comprising a peptide selected from:

i) DHX$_1$X$_2$X$_3$ X$_4$X$_5$X$_6$;     (SEQ ID NO: 30)

wherein
X1 is any amino acid, optionally L, H, R Q;
X2 is S or L;
X3 is D, S or N;
X4 is N or D;
X5 is Y or S; and/or
X6 is T or Y;
ii) a conservative variant of i); and/or
iii) a fragment of i) and/or ii);
wherein the conservative variant and/or fragment retains biological activity and the peptide is 15 or less amino acids.

Examples of Link N sequences are provided in Example 10. In an embodiment, Link N fragment polypeptides include sequences described or based on the conservation motif determinable from the sequences described in Example 10.

In an embodiment, the isolated polypeptide comprises a peptide consisting of DHX$_1$SX$_3$ NYT (SEQ ID NO: 31); wherein X1 is any amino acid, optionally L, H, R Q; and/or X3 is D, S or N; a conservative variant thereof and/or a fragment thereof; wherein the conservative variant and/or fragment retains biological activity and the peptide is 15 or less amino acids.

In an embodiment the isolated polypeptide (referred to herein as a Link N fragment or Link N fragment polypeptide) comprising a peptide selected from i) DHX₁SDNYT, wherein X₁ is L or H (SEQ ID NO: 1);
ii) a conservative variant of i); and
iii) a fragment of i) and/or ii);
wherein the conservative variant and/or fragment retains biological activity and the peptide is 15 or less amino acids.

The conservative variant b) can for example comprise one or more conservative variant substitutions.

In an embodiment the biological activity is binding BMP receptor type II and/or activation of SMAD 1/5 activity.

In an embodiment, the encompassed conservative variant polypeptides are those that binds BMP receptor II and activates SMAD1/5 activity compared to scrambled or reverse Link N.

The fragment c) can for example be 4 amino acids, 5 amino acids, 6, amino acids or 7 amino acids of SEQ ID NO:1, 2, 3, 4 or 5. The fragment can comprise the N terminal most amino acids or the C terminal most amino acids.

For example, smaller fragments can be tested for activity as described for example in Example 9.

In an embodiment, the fragment binds BMP receptor II and activates SMAD1/5 activity compared to scrambled or reverse Link N.

BMP receptor type II binding and/or SMAD activation can be assessed for example as described in the literature for example in Wang et al (33).

In an embodiment, the peptide consists of DHX₁SDNYT (SEQ ID NO: 1); wherein X, is L or H or a conservative variant thereof that retains biological activity.

In another embodiment, the isolated polypeptide comprises a peptide sequence consisting of DHLSDNYT (SEQ ID NO: 2) or a conservative variant thereof that retains biological activity.

In another embodiment, the isolated polypeptide comprises a peptide sequence consisting of DHHSDNYT (SEQ ID NO: 3) or a conservative variant thereof that retains biological activity. In an embodiment, the isolated polypeptide comprises a peptide consisting of DHLSDNYT (SEQ ID NO: 2) or DHHSDNYT (SEQ ID NO: 3).

Larger fragments include up to 15 amino acids of Link N (e.g. human or bovine Link N). In an embodiment, the peptide is 4, 5, 6, 7, 8, 9, 10, 11, 12, 13, 14 or 15 amino acids.

Accordingly in an embodiment, the isolated polypeptide comprises a peptide selected from:

```
                                              (SEQ ID NO: 6)
i) DHX₁X₂X₃ X₄X₅X₆X₇ X₈ X₉DX₁₀ X₁₁X₁₂, X₁₃,
``` wherein X1 is any amino acid, optionally L, H, R Q;
X2 is S or L;
X3 is D, S or N;
X4 is N or D:
X5 is Y or S;
X6 is T or Y;
X7 is L V or T;
X8 is any amino acid, optionally D G, N or P;
X9 is H Y or P;
X10 is R or Q;
X11 is A V or D;
X12 is I or R; and/or
X13 is H or V;
ii) a conservative variant of i); and/or
iii) a fragment of i) and/or ii);
wherein the conservative variant and/or fragment retains biological activity and wherein the peptide is 15 amino acids or less and one or more consecutive C terminal and/or N terminal residues are deleted.

In an embodiment the isolated polypeptide comprises a peptide selected from:
i) DHX₁SX₃ NYTX₇X₈ HDRVIH (SEQ ID NO: 7) or DHX₁ SDNYTX7DHDRX12I (SEQ ID NO: 8); wherein X₁ is L or H, X₇ is L or V and/or X12 is A or V;
ii) a conservative variant of i); and
iii) a fragment of i) and/or ii);
wherein the conservative variant and/or fragment retains biological activity.

In another embodiment, the isolated polypeptide comprises the sequence DHLSDNYTLDHDRAI (SEQ ID NO: 9) or a conservative variant and/or fragment thereof that retains biological activity.

In another embodiment, the isolated polypeptide comprises the sequence DHHSDNYTVDHDRVI (SEQ ID NO: 10) or a conservative variant and/or fragment thereof that retains biological activity.

It is demonstrated herein that bovine Link N and human Link N which share 81% sequence identity both have biological activity. Accordingly, in an embodiment, the isolated polypeptide comprises a peptide that has at least 80%, 85%, 90%, 95% sequence identity to SEQ ID NO: 1, 2, 3, 4, 5 or 6. In an embodiment, residues corresponding to X₁, X₂ and/or X₃ of SEQ ID NO: 4 are modified.

In an embodiment the fragment is 4 amino acids, 5 amino acids, 6, amino acids, 7 amino acids, 8 amino acids, 9 amino acids, 10 amino acids, 11 amino acids, 12 amino acids, 13 amino acids, 14 amino acids or 15 amino acids of SEQ ID NO: 4, 5 or 6.

The fragment can comprise the N terminal most amino acids or the C terminal most amino acids.

In an embodiment, the fragment binds BMP receptor II and activates SMAD1/5 activity compared to scrambled or reverse Link N.

In an embodiment, the isolated peptide is conjugated to a solid support, optionally a gel type support such as solvated polymers with a distribution of functional groups, for example, polystyrene: Styrene cross-linked with 1-2% divinylbenzene; Polyacrylamide: A hydrophilic alternative to polystyrene; Polyethylene glycol (PEG): PEG-Polystyrene (PEG-PS). In an embodiment the solid support is a PEG-based supports for example composed of a PEG-polypropylene glycol network or PEG with polyamide or polystyrene. In an embodiment, the solid support is a surface-type support including for example controlled pore glass, cellulose fibers, and highly cross-linked polystyrene. In an embodiment, the solid support is a composite for example a gel-type polymer supported by rigid matrix.

In an embodiment, the isolated polypeptide comprises one or more protected groups. In an embodiment, the isolated polypeptide has a N-terminal protecting group. In an embodiment, the isolated polypeptide has a C-terminal protecting group. In an embodiment, the isolated polypeptide has a side change protecting group.

In an embodiment, the isolated peptide comprises a N protected group.

In an embodiment, the isolated polypeptide comprises a Fmoc protecting group. In an embodiment, the isolated polypeptide comprises a t-Boc protecting group. Fmoc. In an embodiment, the protecting group is a Benzylozy carbonyl (Z) group. In an embodiment, the isolated polypeptide has an alloc protecting group. In another embodiment, the isolated polypeptide has a lithographic protecting group.

In an embodiment, the isolated polypeptide is configured or comprised in a dendrimer. In an embodiment, the dendrimer comprises at least 2, at least 3 at least 4 or more isolated polypeptides described herein conjugated to a dendrimer scaffold. In an embodiment the dendrimer scaffold is a poly lysine scaffold.

In an embodiment the isolated polypeptide is conjugated to a carrier moiety such as PEG or albumin, a bead.

In an embodiment, the peptide is conjugated to an activity moiety selected from a homing moiety, a stabilizing moiety, a protection moiety and an administration moiety, optionally wherein the activity moiety is proteinaceous.

For example, a stabilizing moiety can be a protein sequence of amino acids that resists natural degradation and/or protein turnover such as an immunoglobulin Fc portion, albumin and the like optionally wherein the moiety conjugated to the N and/or C terminus of the isolated peptide.

In an embodiment the isolated polypeptide is conjugated to a detectable or purification tag, for example a moiety such as a peptide sequence that can be appended or introduced into recombinant protein and is useful for detecting its expression or purifying the polypeptide. In an embodiment, the purification tag is conjugated to the isolated peptide via a linker that comprises a proteolytic cleavage site.

In an embodiment, the isolated peptide is comprised in a liposome or nanoparticle. In an embodiment, the liposome is a slow release liposome. In an embodiment the liposome is a pegylated liposome.

A further aspect is an isolated nucleic acid that encodes the isolated Link N fragment polypeptide described herein. The isolated nucleic acid can be naked or comprised in a vector. Also provided in an embodiment is nucleic acid that hybridizes to a nucleic acid that encodes the isolated Link N fragment polypeptide described herein. In an embodiment, the nucleic acid is codon optimized.

Accordingly a further aspect includes a vector comprising the isolated nucleic acid and/or isolated polypeptide described herein. Vectors can include retroviral vectors, adenoviral vectors and DNA virus vectors for nucleic acids and liposomes or nanoparticles for polypeptides. In an embodiment, the vector is a liposome or nanoparticle. In an embodiment, the liposome is a slow release liposome The isolated polypeptide and/or nucleic acid can be made using recombinant techniques, and or synthesized synthetically.

In an embodiment, the isolated polypeptide is produced synthetically and is unglycosylated or differentially glycosylated compared to human in vivo expressed polypeptide.

In an embodiment, the isolated polypeptide is cyclized. In an embodiment, the isolated polypeptide comprises one or more D amino acids or more or more L amino acids.

A further aspect includes a recombinant cell expressing the isolated Link N fragment polypeptide described herein and/or comprising the isolated nucleic acid or vector described herein.

A variety of recombinant cells can be made expressing the Link N fragments of the disclosure. For example a cell can be transformed, transfected or transduced with a vector comprising a nucleic acid encoding a Link N fragment of the application.

In an embodiment, the cell is a chondrocyte lineage cell, a stem cell or a disc cell, optionally wherein the stem cell is a mesenchymal stem cell. In an embodiment, the recombinant cell is for therapeutic use.

A further aspect is a composition comprising the isolated polypeptide described herein and optionally a carrier or diluent.

Also provided in another aspect is a composition comprising the isolated nucleic acid, vector, or recombinant cell described herein.

In an embodiment, the diluent is a physiological buffer, optionally a sterile physiological buffer.

In an embodiment, the composition is a pharmaceutical composition comprising a pharmaceutically acceptable carrier or diluent.

The isolated polypeptide, isolated nucleic acid, vector, recombinant cell can optionally by lyophilized, or in a liquid, gel or solid composition.

The composition can be a lyophilized powder or aqueous or non-aqueous solution or suspensions, which may further contain antioxidants, buffers, bacteriostats and solutes. Other components that may be present in such compositions include water, surfactants (such as Tween), alcohols, polyols, glycerin and vegetable oils, for example.

Suitable diluents for nucleic acids include but are not limited to water, saline solutions and ethanol.

Suitable diluents for polypeptides, and/or cells include but are not limited to saline solutions, pH buffered solutions and glycerol solutions or other solutions suitable for freezing polypeptides and/or cells.

The composition can further comprise stabilizing agents, for example reducing agents, hydrophobic additives, and protease inhibitors which are added to physiological buffers.

In an embodiment, the composition comprises a scaffold formed of a biocompatible material comprising the isolated polypeptide, recombinant cell and/or composition described herein.

In an embodiment, the biocompatible material is selected from an alginate agarose, chitosan, Polycaprolacton and/or hyaluronic acid (or hyaluronate) based biomaterial. Generic scaffolds for chondrocytes and/or IVD cells can also be used.

In embodiment, the scaffold is formed into a hydrogel, microsphere, microcapsule, sponge, foam or fiber.

In an embodiment, the composition is for preparing a cartilage or disc cell for transplant into a subject, the composition comprising an isolated polypeptide and/or recombinant cell described herein, a cartilage and/or disc cell and a carrier or diluent, wherein the cartilage and/or disc cell is exposed to an effective amount of said isolated polypeptide and/or recombinant cell sufficient to induce the cartilage cell and/or disc cell to increase proteoglycan and/or collagen II synthesis. The composition and/or cells of the composition can be isolated and used for example for treating a tissue pathology in a subject upon administration of the composition to the subject.

In an embodiment, the pharmaceutical composition is for use in the treatment of a cartilage or disc tissue pathology in a subject, the composition comprising an isolated polypeptide and/or recombinant cell described herein, a cartilage and/or disc cell and a pharmaceutically acceptable carrier or diluent, wherein the treatment comprises exposing the cartilage and/or disc cell to an effective amount of said isolated polypeptide and/or recombinant cell sufficient to induce the cartilage cell and/or disc cell to increase proteoglycan and/or collagen II synthesis for treating the tissue pathology in the subject upon administration of the composition to the subject.

In an embodiment, the composition (including the pharmaceutical composition) comprises a scaffold formed of a biocompatible material, and wherein the cartilage and/or disc cell is disposed on or in the scaffold.

In an embodiment, the composition comprising the cartilage and/or disc cell is cultured for at least 1 day, at least 2 days at least 3 days, at least 4 days or at least 5 days prior to administration.

Another aspect includes a method of inducing matrix synthesis optionally proteoglycan synthesis and/or collagen II synthesis in a cartilage and/or disc cell or in a tissue comprising a cartilage and/or disc cell the method comprising incubating the cartilage and/or disc cell with an effective amount of the isolated polypeptide, recombinant cell expressing said isolated polypeptide and/or composition as described herein, under conditions to induce proteoglycan synthesis, producing an induced cartilage and/or disc cell with increased matrix synthesis.

Matrix synthesis can be measured for example by assessing proteoglycan and/or collagen II synthesis as described in the Examples.

In an embodiment the method is conducted in vitro in a cell culture, optionally a disc organ culture, to produce a cell or tissue with increased matrix synthesis.

In an embodiment, the cell and/or tissue is contacted under conditions to produce cartilage, optionally for use in cartilage transplantation.

In an embodiment, the cartilage cell is a chondrocyte. In an embodiment, the disc cell is an AP cell optionally an IAP cell. In another embodiment, the disc cell is a NP cell. In a further embodiment, a mixed population of cells is used e.g. comprising AP and NP. In an embodiment, the tissue comprises cartilage lineage cells. In an embodiment, the tissue comprises AP and/or NP lineage cells.

In an embodiment, the recombinant cell is a MSC expressing an isolated polypeptide described herein.

In an embodiment, the cartilage cell, disc cell and/or tissue is in a subject and the contacting is conducted by administering to the subject an isolated polypeptide, a recombinant cell or a composition of claim 14 or 15, described herein.

In an embodiment, the induced cartilage and/or disc cell is introduced into the subject.

In an embodiment, the cartilage cell and/or disc cell is an autologous cell that is treated in vitro. For example, in mosaicplasty small often circular (4-8 mm) autogenous grafts are taken for example from non-weight bearing regions of the knee. In an embodiment, Link N is injected or administered before taking and/or when reintroducing the autogenous graft to try to promote repair. For example this may help repair the harvest site and/or treating the implantation site may promote repair around the graft and where the graft was taken from.

Another aspect includes a method of producing cartilage and/or disc tissue for implanting into a subject, the method comprising incubating/cultured the cartilage and/or disc cell with an effective amount of the isolated polypeptide, recombinant cell expressing said isolated polypeptide and/or composition as described herein, under conditions to induce proteoglycan synthesis, producing an induced cartilage and/or disc cell with increased matrix synthesis, optionally increased proteoglycan synthesis; and isolating a substantially pure population of induced cartilage and/or disc cells.

In an embodiment, the matrix comprises a cartilaginous matrix. In an embodiment, the cartilaginous matrix comprises proteoglycan and/or collagen, for example collagen II.

In an embodiment the proteoglycan synthesis is aggrecan.

In an embodiment, the cartilage and/or disc cell is in cultured in a 3D culture comprising a scaffold, such as an alginate scaffold for example as described in the Examples.

In an embodiment the induced cartilage and/or disc cell is implanted into a subject.

In an embodiment approximately 0.5 micrograms/mL is for example used in a cell culture and/or for administration. In another embodiment, about 0.5 micrograms/mL to about 10 mg/ml is used, optionally about 10 micrograms/mL, about 100 micrograms/mL, about 1000 micrograms/mL, about 2 mgrams/mL, about 3 mgrams/mL, about 4 mgrams/mL, about 5 mgrams/mL, about 6 mgrams/ml, about 7 mgrams/mL, about 8 mgrams/mL about 9 mgrams/mL or about 10 mgrams/mL. In an embodiment, the dose is any 10 microgram/mL increment of 0.5 micrograms up to about 10 mgs. In an embodiment, the amount is weight/volume. In an embodiment, per injection amount is administered. For example, in an embodiment, up to or about 1 mg is injected per lumbar disc or up to 1 mg is introduced per joint.

A further aspect includes a method of alleviating a symptom associated with—and/or treating—a cartilage and/or disc tissue pathology comprising administering to a subject in need thereof an isolated polypeptide, a recombinant cell, induced cartilage and/or disc cell and/or a pharmaceutical composition described herein.

Figure 28:
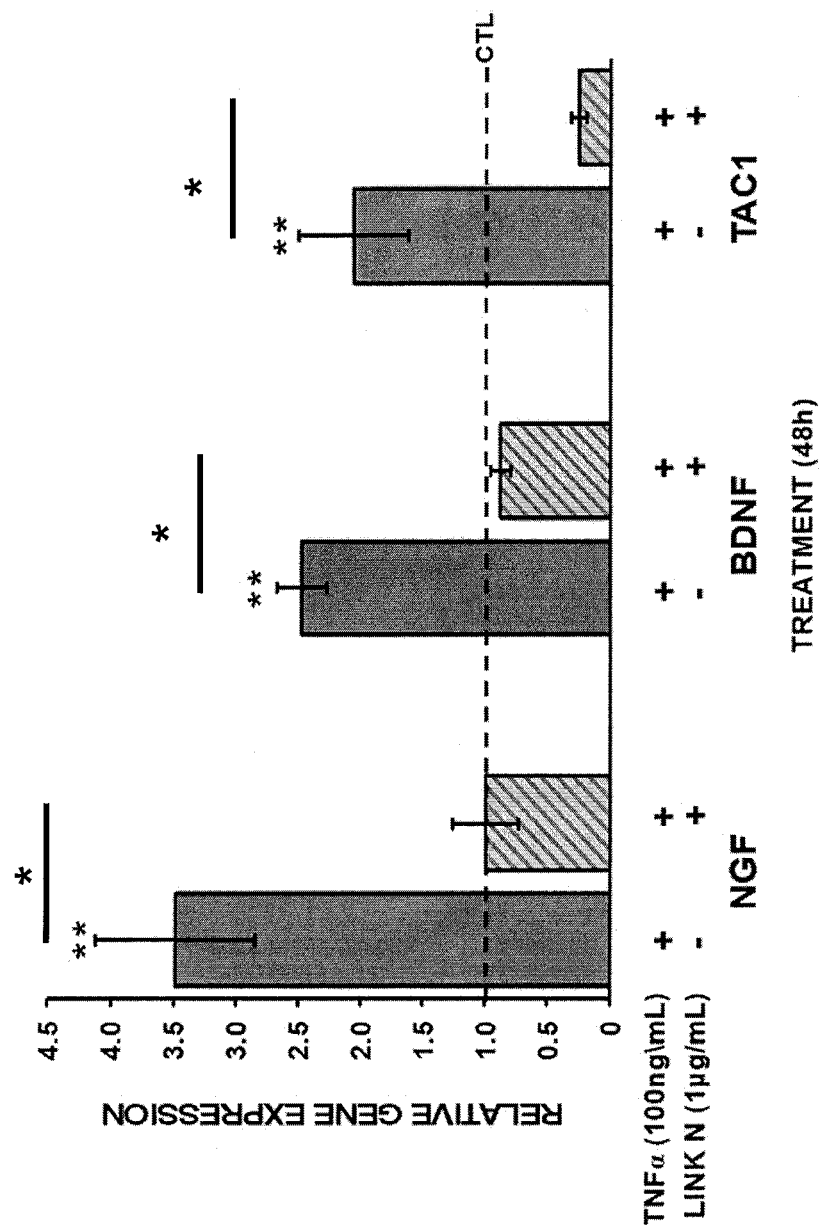
FIG. 28: Link N suppresses TNFα stimulated expression of neurotrophin (NGF and BDNF) and Substance P (TAC1) in annulus fibrosus (AF) cell. AF cells from grade 2 human discs were stimulated 24 hrs with either Link N (1 µg/ml)+TNFα (100 ng/ml) or TNFα (100 ng/ml) alone. The results are shown as means±S.D. of four independent experiments with four different donors. $*p<0.05$ vs. control.
Figure 29:
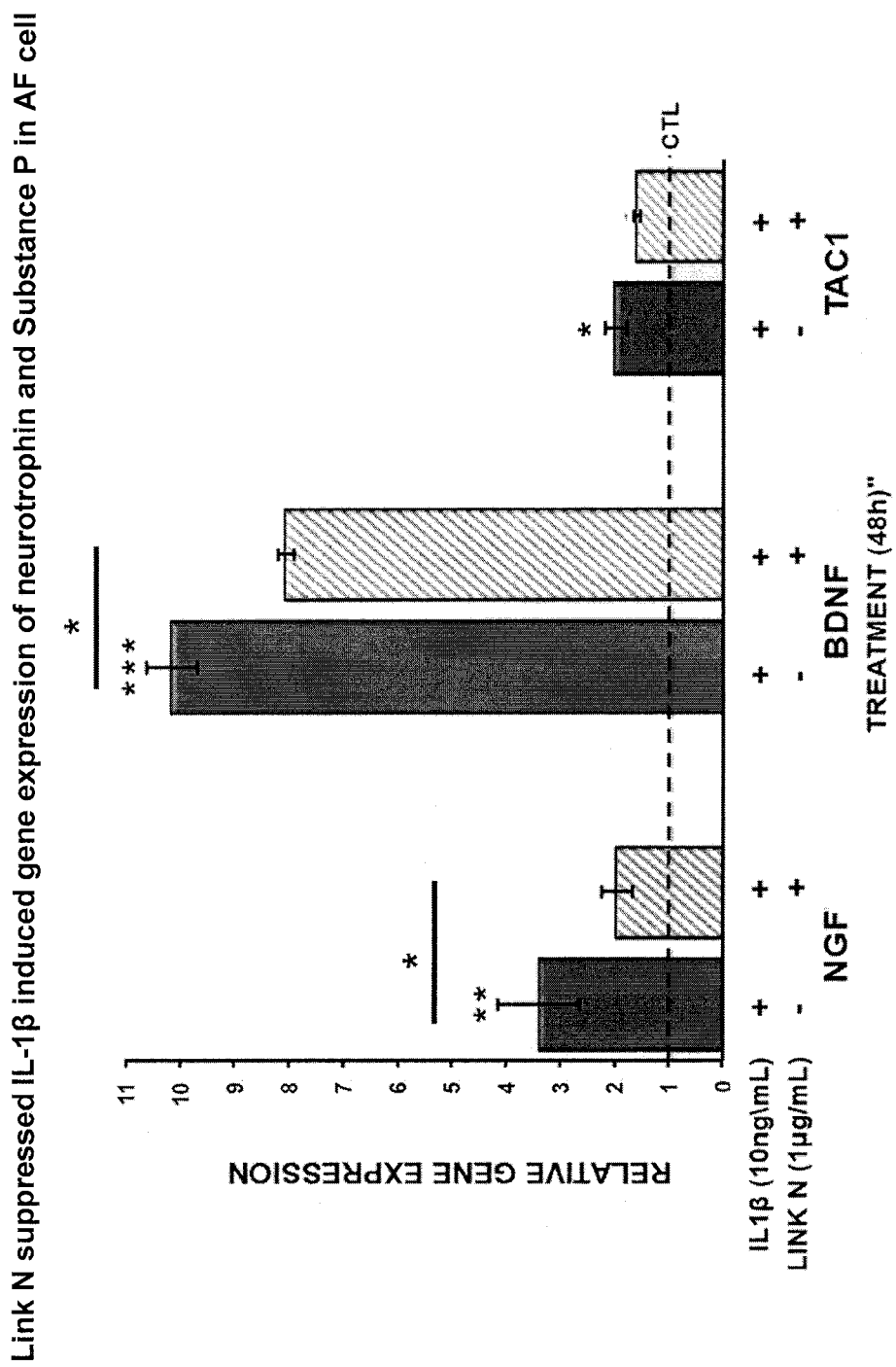
FIG. 29: Link N suppresses IL-1β stimulated expression of neurotrophin (NGF and BDNF) and Substance P (TAC1) in annulus fibrosus (AF) cell. AF cells from grade 2 human discs were stimulated 24 hrs with either Link N (1 µg/ml)+IL-1β (10 ng/ml) or IL-1β (10 ng/ml) alone. The results are shown as means±S.D. of four independent experiments with four different donors. $*p<0.05$ vs. control.

In an embodiment, the symptom is pain. As demonstrated in FIGS. 27-30 NGF expression in IVD increases with degeneration in both NP and AF cells and Link N can suppress the TNF alpha induced gene expression of neurotrophins (NGF, BDNF) and Substance P (TAC1) in AF cells. FIG. 29 demonstrates that Link N suppresses IL-1beta induced expression of neurotrophins (NGF, BDNF) and substance P (TAC1) in AF cells. Neurotrophins, and substance P are mediators of pain.

In an embodiment, the cartilage and/or disc tissue pathology is intervertebral disc degeneration. In an embodiment, the intervertebral disc degeneration is early stage. For example early stage disc degeneration includes Thompson grade 1, 2 and/or 3 degeneration, or optionally while the AF is substantially intact for example as determinable upon imaging such as MRI. Late stage disc degeneration can include for example Thompson grade 4, Thompson grade 5 or greater degeneration and/or where fusion has taken place. For example the products and methods described herein can be used to treat and/or prevent adjacent disc degeneration after fusion.

Sensitive and/or quantitative MRI methods can be used for selecting subjects suitable for receiving a treatment described herein. In an embodiment, the treatment is administered prophylactically, e.g. after detectable degeneration but before painful degenerate disc to repair and/or retard degeneration.

In an embodiment, the subject has decreased cell density and/or metabolic activity, optionally wherein the decreased cell density and/or metabolic activity is due to age.

In an embodiment, the cartilage and/or disc tissue pathology is an inflammatory or degenerative joint disease selected from arthritis, undesirable osteogenesis and/or calcification.

In an embodiment, the arthritis is osteoarthritis.

In another embodiment, the arthritis is rheumatoid arthritis.

In an embodiment, the cartilage and/or disc tissue pathology is osteoporosis. In an embodiment, the cartilage and/or disc tissue is osteolysis.

In an embodiment, the cartilage and/or disc tissue pathology is a mechanical injury.

In an embodiment, the subject is a mammal optionally selected from a human, horse, cow, goat or dog. In an embodiment, the subject is human.

It has been shown that loss of BMP receptor II expression causes endothelial inflammation and atherosclerosis is a mouse model. Link N has been shown to bind BMP type II receptor and is shown herein to inhibit NFkappaB activation. Accordingly a further aspect is a method of alleviating a symptom and/or treating a subject with endothelial inflammation and/or atherosclerosis comprising administering to a subject in need thereof an isolated Link N fragment polypeptide, a recombinant cell, induced cartilage and/or disc cell and/or a pharmaceutical composition described herein.

In an embodiment, the isolated polypeptide, recombinant cell and/or pharmaceutical composition is administered to the subject in a scaffold.

The isolated Link N polypeptide, recombinant cell, induced cell or pharmaceutical composition can be administered to the subject percutaneously and/or near or at the site of tissue pathology. For disc tissue pathologies, the isolated Link N fragment polypeptide, recombinant cell and/or induced cells can be administered, implanted or transplanted into a subject by intradiscal injection for example, injection into the NP, the AF, optionally the inner AF. For joint pathologies, the isolated Link N fragment polypeptide, recombinant cell and/or induced cells can be administered, implanted or transplanted into a subject by injecting into the affected region. In some embodiments, autologous cells and/or tissues for example as done in mosaicplasty are excised, treated as described and re-implanted.

In an embodiment, the isolated Link N fragment polypeptide, recombinant cell and/or induced cells can be administered, implanted or transplanted into a subject by injecting into synovial fluid. In an embodiment, where the subject has a implant scaffold for example to repair lesions, the administration can proceed by injection/introduction into the embedded implant scaffold.

In an embodiment, an existing ex vivo scaffold comprising chondrocytes and/or MSC and/or induced cells can be further impregnated with isolated Link N polypeptides, compositions comprising Link N fragment products described herein. The scaffold can then be injected into a subject in need thereof.

Disc and cartilage repair can be enhanced by mesenchymal MSC and Link N supplementation to maximize extracellular matrix production.

In an embodiment, the isolated Link N fragment polypeptide, recombinant cell induced cell and/or composition comprising one or more of the foregoing is used to repair a disc lesion. Natural disc degeneration can involve the creation of fissures. To repair such lesions, Link N fragments and stem cells can be implanted in a polymerizable scaffold that will fill the lesions and allow uniform distribution of the introduced agents.

In a further embodiment, the isolated polypeptide or pharmaceutical composition comprising the isolated polypeptide is administered in a combination therapy.

In an embodiment, the subject has received an implant, optionally treated as described herein or untreated. The subject is for example administered an isolated polypeptide described herein to increase proteoglycan production.

In an embodiment, the method further comprises contacting the cell or tissue with or administering to the subject, MSC in combination with an isolated polypeptide, recombinant cell or composition described herein.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Presently, there are no established treatments to prevent, stop or even retard back pain arising from disc degeneration. Previous studies have shown that Link N can act as a growth factor and stimulate the synthesis of proteoglycans and collagens, in IVD. However, the sequences in Link N involved in modulating cellular activity are not well understood. To determine if disc cells can proteolytically process Link N, human disc cells were exposed to native Link N over a 48 h period and as described further below, mass spectrometric analysis revealed that a peptide spanning residues 1 to 8 was generated in the presence of AF cells but not NP cells. Link N 1-8 significantly induced proteoglycan production in the presence of IL-1β NP and AF cells, confirming that the biological effect is maintained in the first 8 amino acids of the peptide and indicating that the effect is sustained in an inflammatory environment.

The unique effects of Link N in modulating cellular activity suggest a sequence and/or motif specific interaction. However, it is less clear if Link N is stable in a biological system. The fate of Link N in a biological system was also studied.

Method and Materials

Materials

Pronase was from Calbiochem (Darmstadt, Germany). Collagenase 1A, GlutaMAX, NaCl and formic acid were purchased from Sigma (St. Louis, Mo., USA). Low viscosity alginate (Keltone LV) was obtained from Kelco Chemical Co. (San Diego, Calif., USA). Penicillin/streptomycin, gentamicin sulphate, amphotericin B, Dulbecco's Modified Eagle Medium (DMEM) and foetal calf serum (FCS) were obtained from Gibco (Burlington, ON, Canada). 20 G 1½ inch needles to make alginate beads were obtained from BD syringes, (Concord, ON, Canada). HPLC grade acetonitrile was purchased from Rathburn (Walkerburn, Scotland). Trypsin Gold mass spectrometry grade was purchased from Promega (Madison, Wis., USA). TopSert, TPX-Short Thread-Vial, 32×11.6 mm with integrated 0.2 mL Glass-Micro-Insert, 15 mm top were purchased from Skandinaviska GeneTec AB (Västra Frölunda, Sweden). Vydac UltraMicro Spin® Silica C18 300 Å columns were purchased from The Nest Group (Southborough, Mass., USA). Sequencing grade chymotrypsin was purchased from Roche Diagnostics GmbH (Mannheim, Germany). $^{35}SO_4$, 2 mCi, stabilized aqueous solution was ordered from Perkin Elmer (Montreal, Quebec, Canada). NUNC 6 well culture plates were purchased from Corning Inc. (Edmonton, Alberta, Canada). MMPs 3, 7, 12, 13, ADAMTS 4,5, were from R&D Systems (Minneapolis, Minn.). HTRA1 from Thermo Scientific (Waltham, Mass.). Cathepsins K, B, and L were provided.

Link-N Peptide

Link N, DHLSDNYTLDHDRAIH (SEQ ID NO: 15); reverse Link N, HIARDHDLTYNDSLHD (R-Link N) (SEQ ID NO: 16), scrambled Link N, DLNRAHLHIDYHTDSD (S-Link N) (SEQ ID NO:17), Link-N first 8 peptide residues, DHLSDNYT (Link N 1-8) (SEQ ID NO: 2), and second 8 peptide residues, LDHDRAIH (Link N 9-16) (SEQ ID NO: 18), were synthesized by CanPeptide (Pointe Claire, QC, Canada). The scrambled 16 amino acid peptide sequence was designed using a bioinformatics tool from Institut Pasteur, Paris, France (http://mobyle.pasteur.fr). The sequence was selected to mimic the overall properties of Link N, such as isoelectric point and solubility of the original peptide. Stock solutions (10 mg/mL) of the peptides were prepared in DMEM, supplemented with HEPES and pH was adjusted to 7.4 before use.

Source of Tissues

Human thoracolumbar spines were retrieved through the Transplant Quebec organ donation program. Discs were obtained from 7 donors, 1 male and 6 female, with a mean age of 29.6 years and an age range of 16 to 47 years (Table 1). Donors having had recent chemotherapy, radiation therapies to the spine, or significant long-standing paralysis were excluded from the study. Spine retrieval was performed within 8 h of death. Discs with calcification and loss of disc height were not included in the study. All procedures were approved by the institutional review board of the Montreal General Hospital.

Bovine tails from 18-27 months old steers were obtained from a local abattoir within 6 h of slaughter.

Isolation of Human and Bovine IVD Cells

Human and bovine IVDs were separated from the adjoining vertebral body and divided into NP and AF for bovine IVDs and NP and inner annulus fibrosus (iAF) for human IVDs. Tissue from the human outer annulus fibrosus (oAF) was not used for cell isolation in this study. Cells were enzymatically isolated from each region as previously described (63). Briefly, NP and AF tissues were dissected into approximately 2-mm thick pieces, washed twice in PBS containing 50 µg/mL gentamicin, 100 ug/mL penicillin, 100 U streptomycin and 0.25 µg/mL fungizone, then digested with 0.2% pronase for 1 h, followed by collagenase type IA at 0.01% for NP and 0.04% for AF tissue for 4 h in serum free DMEM.

Monolayer Cultures of Human IVD Cells

To evaluate the stability of Link N, freshly isolated human cells from NP and AF regions were plated in 6 well culture plates at a density of 250,000 cells per well. Cells were cultured at 37° C., 5% $CO_2$ in 3 mL DMEM, containing 4.5 g/L glucose and supplemented with 10% FCS, 25 mmol/L HEPES, 50 µg/mL gentamicin sulphate, 0.25 µg/mL fungizone, 50 µg/mL L-ascorbate, and 2 mmol/L GlutaMAX. The wells were left for 2 days before exposure to Link-N (1 µg/mL). 200 µL medium was collected at fixed time points (0 h, 6 h, 12 h, 24 h, 36 h, and 48 h). Stability of the peptide was also studied at the same time points in the absence of cells.

Proteinase Treatment of Link N

300 µg Link N 1-16 was incubated for 30 minutes, 2 and 24 hours in the presence of 10 different proteinases. The buffer used for MMPs 3, 7, 12, 13, ADAMTS 4,5, HTRA1 was composed of 50 mM Tris-HCl, 200 mM NaCl, 5 mM $CaCl_2$, 0.01% Rapigest. For cathepsins K, B, and L, the digest buffer was composed of 2.5 mM DTT, 0.15% chondroitin sulfate A, 0.1 M sodium acetate, pH 5.5.

Mass Spectrometry

25 µL medium samples, collected from the monolayer cultures described above or peptide digests were purified on C18 spin columns according to standard protocols (Harvard Apparatus, Holliston, Mass.). Eluted peptides were reconstituted in 20 µL, 2% acetonitrile and 0.2% formic acid (FA). Samples were injected and quantified using a triple quadropole mass spectrometer TSQ Vantage™ (Thermo Scientific, Waltham, Mass.) equipped with an easy nano-LC system (Thermo Scientific). The mass spectrometer was operated in SRM mode, with both Q1 and Q3 settings at unit resolution (FWHM 0.7 Da). A spray voltage of +1,700 V was used with a heated ion transfer setting of 270° C. for desolvation. Data were acquired using the Xcalibur software (version 2.1). Mobile phases used were A (0.1% FA in water) and B (100% acetonitrile in 0.1% FA). Separation was performed on 10 µm tip, 75 µm×15 cm capillary columns (PicoTip™ emitter, New Objective, Woburn, Mass.) packed with Reprosil-Pur C18-AQ resin (3 µm, Dr. Maich GmbH, Switzerland). 1 µL sample was injected and separation was performed at a flow rate of 300 nL/min using a gradient of 97% mobile phase A for 5 min, 85% A for 8 min, 65% A for 42 min, and 19% A for 45-50 min.

A multiple reaction monitoring method (MRM) for the Link N peptides was developed, optimized and used with the sum peak area from transitions, Link 1-16 transitions: 641.30 (3+)→863.41 (y7), 641.30→748.38 (y6), 641.30→611.33 (y5) and 641.30→682.28 (b6), Link 1-8 transitions: 964.40 (1+)→845.43 (b7)→682.87 (b6)→682.23 (b5)→453.20 (b4)→712.31 (y6)→849.37 (y7), Link 9-16 transitions: 488.75 (2+)→821.43 (b7)→708.34 (b6)→496.30 ((y4)→611.32 (y5)→748.38 (y6). The MRM data was analysed using the Skyline 1.4 software (MacCoss Lab Software, University of Washington, Seattle, Wash.).

Discovery experiments were also run in order to identify any fragmentation of the peptide by injection of 8 µL sample onto a reversed phase liquid chromatography system on-line with electrospray-ion trap mass spectrometry (LC ESI MS), as previously described (64).

Culture of IVD Cells in 3D Scaffolds

To compare the metabolic response to the various Link N peptides, freshly isolated human and bovine cells from NP and AF regions were embedded in 1.2% alginate beads, as previously described (65). Cells in alginate beads were cultured at 37° C., 5% $CO_2$ in DMEM, containing 4.5 g/L glucose and supplemented with 10% FCS, 25 mmol/L HEPES, 50 µg/mL gentamicin sulphate, 0.25 µg/mL fungizone, 50 µg/mL L-ascorbate, and 2 mmol/L GlutaMAX. The beads were stabilized for 7 days and cell viability was assessed by Live/Dead® assay prior to further treatment. 5 beads per well were then cultured in 48 well plates in the presence of equimolar concentrations of either Link N (1 µg/mL), R-Link N (1 µg/mL), S-Link N (1 µg/mL), Link N 1-8 (0.5 µg/mL) or Link N 9-16 (0.5 µg/mL) in 0.5 mL DMEM. 25 µCi/mL $^{35}SO_4$ was added to the medium to allow assessment of proteoglycan synthesis (66). In addition, beads were exposed for 48 h to IL-1β (10 ng/mL) alone, or to a combination of peptides and IL-1β (51). At the end of the culture period, medium was collected and dialyzed exhaustively against miliQ water at 18.2Ω (Spectra/Por® 3), followed by cold chase with 1M $MgSO_4$ for 2 h to remove any remaining unincorporated $^{35}SO_4$. The $^{35}SO_4$ incorporation was measured using a beta scintillation counter (Beckman Coulter LS6500, Beckman Coulter, Mississauga, Canada).

Statistical Analysis

One tailed paired t-test was performed and values 0.05 were taken as significant.

Results

The 16 amino acid Link N peptide is known to induce proteoglycan synthesis in isolated disc cells and intact human discs, and also to increase disc height in a rabbit disc puncture degeneration model (34, 31, 29). It is however not clear if the effect is strictly sequence dependent or if it is attributed to the overall properties of the peptide. Three variants of the peptide were synthesized to address this, native (Link N), reversed (R-Link N) and scrambled (S-Link N), and $^{35}SO_4$ incorporation was used to assess proteoglycan synthesis in response to the peptides. Bovine and human NP and AF cells were exposed to 1 µg/mL of the peptides for 48 h. Bovine cells showed a statistically significant increase in proteoglycan synthesis in response to Link N (NP p=0.03, AF p=0.03), but no effect was observed when the cells were exposed to the reversed or scrambled peptides (FIG. 1a). Human cells showed a similar trend, with a significant increase in response to native Link N (NP p=0.008, AF p=0.02) and no response to scrambled or reversed peptides, indicating a sequence specific response (FIG. 1b). Both bovine and human AF cells showed a trend towards a stronger response compared to NP cells.

Peptide stability or maintained activity is important in order to ensure a sustained effect of treatment. Therefore, mass spectrometric analysis was performed to evaluate the stability of Link N in solution. Native Link N with a molecular mass of 1922 Da was incubated at 37° C. for 48 h in culture medium and the intensity of the peptide was quantified up to 48 h using targeted mass spectrometry. No loss of the 1922 Da Link N peptide was found during this time period (FIG. 2), indicating that the peptide is stable in solution at 37° C.

Metabolically active cells have the potential to process short peptides and thereby possibly alter their biological effect (67-69). To determine if disc cells can proteolytically process Link N, human disc cells in monolayer were exposed to native Link N over a 48 h period and the peak area intensity of the 1922 Da peptide was quantified in order to assess its fate. The peptide was found to be stable for at least 48 h in the presence of NP cells (FIG. 3a). However, a decrease in Link N was detected by 6 h in the presence of AF cells, and only trace amounts were present after 48 h (FIG. 3b), demonstrating that AF cells have the ability to process the Link N peptide.

To identify the processed products of Link N, the presence of shorter peptides in a mass spectrum ranging from 0-1930 Da were analyzed. It was apparent when comparing Link N containing medium from NP and AF cells that a peptide with a mass of 964.4 Da was accumulated in the AF cell culture medium (FIG. 4a). The same peptide was present only in very low levels in the NP cell culture medium (FIG. 4a). The 964.4 peptide eluted from the column at 2 different retention times. This phenomenon is sometimes observed and is most likely due to peptide precipitation on the column resulting from the high concentration. Two separate parts of the native 16 amino acid Link N, representing amino acid 1-8 or 4-11, could potentially generate a peptide of this mass (FIG. 4b). Tandem mass spectrometry analysis confirmed that a peptide spanning residues 1 to 8 was generated in the presence of AF cells, but no trace of the peptide 9-16 was found (FIG. 4c).

Maintained activity of peptides designed for biological treatment is of great importance and the processing of Link N by AF cells could potentially alter its biological effect. To evaluate this, two peptides corresponding to amino acid sequence 1-8 (Link N 1-8) and 9-16 (Link N 9-16) were synthesized and their effect on proteoglycan synthesis was compared to that of native human Link N. Proteoglycan synthesis was evaluated using $^{35}SO_4$ incorporation and bovine and human NP and AF cells were exposed to equimolar concentrations of the peptides for 48 h. A statistically significant increase in $^{35}SO_4$ incorporation of the same magnitude as the native peptide was observed (NP p=0.006 and AF p=0.007) when the bovine cells were exposed to Link N 1-8 alone, however no effect was seen with Link N 9-16 (FIG. 5a). Human cells showed a similar trend, with a significant increase in response to Link 1-8 (NP p=0.004 and AF p=0.01), but no response to Link N 9-16, indicating that the biological effect is specific to a sequence maintained in the first 8 amino acids of the peptide (FIG. 5b). Both bovine and human AF cells showed a stronger response compared to NP cells.

To determine the proteinase responsible for cleaving Link 1-16, digests with 10 different proteinases were carried out for 30 minutes, 2 and 24 hours. The proteinases tested were MMPs 3, 7, 12, 13, ADAMTS 4,5, HTRA1, and cathepsins K, B, and L. The peak area intensity of the 1922 Da, Link 1-16 peptide was quantified using mass spectrometry. The intensity of the peak was significantly diminished already after 30 minutes and was hardly detectable at 2 and 24 hours incubation with cathepsin K, while it was un-affected by MMPs 3, 7, 12, 13, ADAMTS 4,5, HTRA1, and cathepsins B, and L (the 2 hour time point is shown in FIG. 6A). A MRM method was set up to evaluate if the m/z 964.4 Da (+1) Link 1-8 appeared as the intensity of 1922 Da peptide disappeared. The method confirmed that Link 1-8 was generated after 2 hours by cathepsin K (FIG. 6B). To evaluate if cathepsin K generate a cleavage between amino acids 8 and 9 or if Link 1-16 is processed at several sites within the residue 8-16 region, a MRM method was set up also for the m/z 488.75 Da (2+) Link 9-16 peptide. The analysis showed the presence of Link 9-16 after 2 hours, confirming that Link N is processed by a single cleavage between amino acids 8 and 9 (FIG. 6C).

Figure 7:
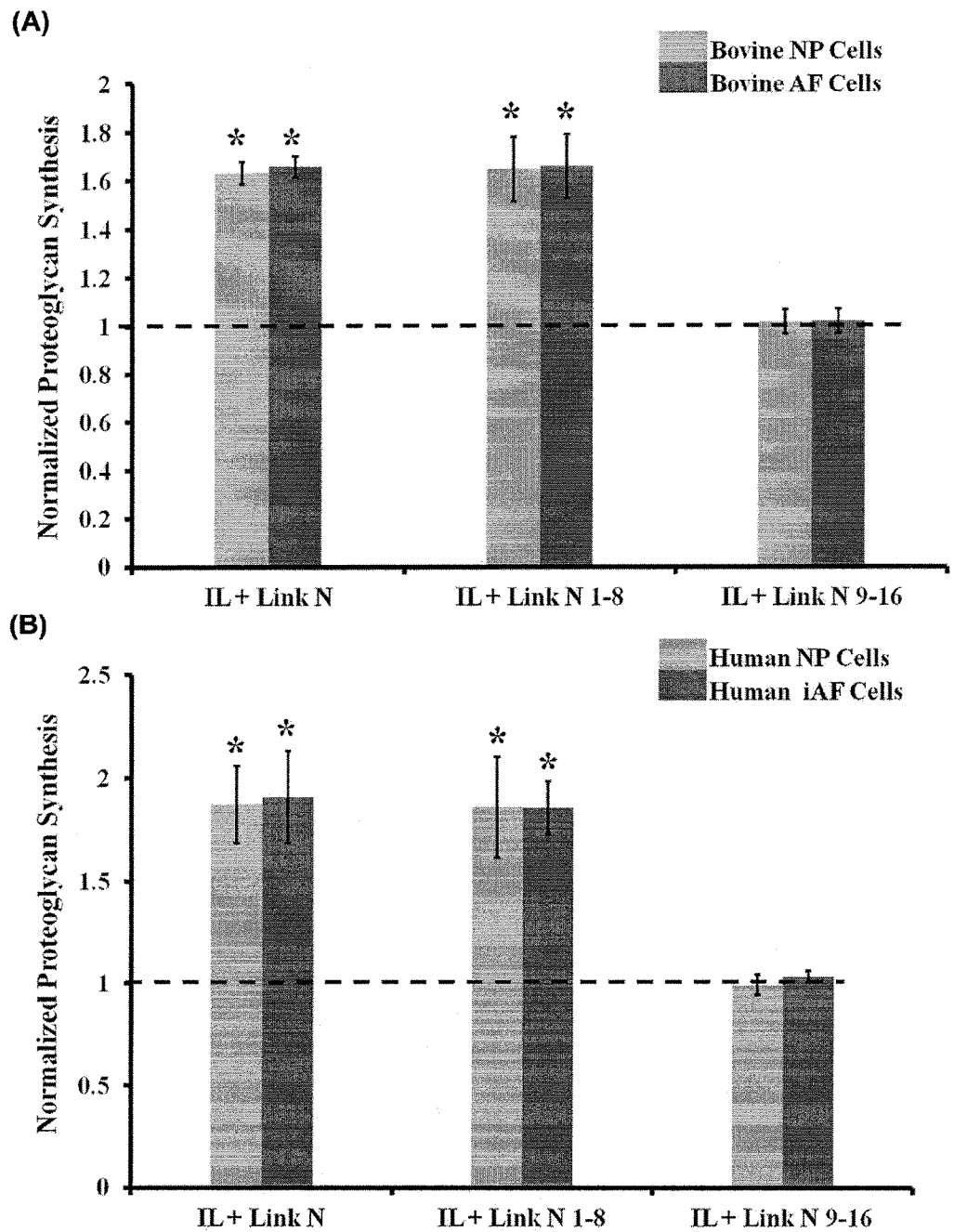
FIG. 7: Proteoglycan synthesis by bovine and human cells in response to Link N fragments in an inflammatory environment. Synthesis was estimated by evaluating $^{35}SO_4$ incorporation after 48 h in IL-1-containing medium, supplemented with Link N (1 µg/mL), Link N 1-8 (0.5 µg/mL), Link N 9-16 (0.5 µg/mL) or medium without peptide supplementation. Relative proteoglycan expression is shown in bovine nucleus pulposus (NP) and annulus fibrosus (AF) (A), and human nucleus pulposus (NP) and inner annulus fibrosus (iAF) cells (B). Data are expressed as mean±SD, of the ratio relative to proteoglycan produced by cells exposed to IL-1-containing medium (n=3). Values where $p \leq 0.05$ (*) were taken as significant.

As disc degeneration is closely linked to the presence of inflammatory cytokines in vivo (51), and native Link N is known to work equally well in an inflammatory environment (34) a response to the peptides was evaluated in the presence of IL-1β to determine whether their beneficial effect is maintained in an inflammatory milieu. Proteoglycan synthesis was evaluated using $^{35}SO_4$ incorporation. Link N 1-8 significantly induced proteoglycan production to the same extent as native Link N in the presence of IL-1β, in bovine NP and AF cells (NP p=0.006 and AF p=0.013) (FIG. 7A). The same trend was found in human cells, with a significantly increased response to Link N 1-8 (NP p=0.002 and AF p=0.004) and no response to Link N 9-16 (FIG. 7B), confirming that the biological effect is maintained in the first 8 amino acids of the peptide and indicating that the effect is sustained in an inflammatory environment.

Discussion

It has previously been reported that Link N can stimulate collagen and proteoglycan synthesis in chondrocytes (70), in IVD cells in vitro and in intact human IVDs ex vivo (19,20), as well as increase disc height in a rabbit model of disc degeneration (31). It is however not known how stable native Link N is in a biological system. The present study demonstrates that AF cells have the ability to proteolytically process the Link N peptide resulting in a fragment spanning amino acid residues 1-8. The data also indicates that the biologically active sequence is preserved within this fragment and that the peptide is able to increase proteoglycan synthesis in both NP and AF cells, even in an inflammatory milieu. AF cells demonstrated a stronger proteoglycan increase over baseline than NP cells. However the absolute concentration produced cannot be evaluated with the method used. It is possible that NP cells have a higher baseline production resulting in a higher total concentration of proteoglycan both with and without Link N exposure. A reversed or scrambled Link N peptide, as well as residues 9-16 of the Link N, had no biological effect.

Wang et al. have previously reported that the stimulatory effect of Link N was lost when they evaluated a number of shorter Link N-derived peptides (33) including a peptide spanning amino acid residues 1-12. In contrast, it was found here that a peptide spanning residues 1-8 of Link N was active. In agreement with the present results they found that a reversed or scrambled peptide had no effect. It is unclear why the residue 1-12 peptide was inactive in their system, but could relate to the different conditions that were used. Wang et al. used 100 ng/mL of the different peptides independent of size.

It was determined that there is an optimal concentration of 1 µg/mL of the 16 amino acid native Link N, therefore used this concentration was used and to maintain equimolar concentrations 0.5 µg/mL of the 8 residue shorter peptides was used. Wang et al measured cell-associated sulphated GAG in cell lysates whereas incorporation of radioactive sulphate in the GAG released into the culture medium was measured herein. The cell source used was also different, Wang et al. isolated cells from degenerated disc tissue extracted during surgery for spinal fusion, and expanded the cells in monolayer culture before transferring them into 3D cultures, a procedure that may have altered the phenotype and thereby the response of the cells.

It has been demonstrated by Abbott et al (71) that monolayer expanded cells from degenerate human discs respond less well to native Link N, with only a low upregulation of aggrecan message levels and a strong induction of MMP3 message levels (71, 18). The dose of Link-N used in the Wang et al study was again lower than the optimal dose that was determined, in this case it was 10 times less (71). The cells tested herein were isolated from organ donors with mild degeneration, and to preserve the phenotype the cells were not expanded in monolayer. This difference and the fact that evaluated cells were not from severely degenerated surgically removed discs may explain the different results]. Discs with severe degeneration may not have sufficient cells to provide a detectable therapeutic response. It is also difficult to separate the different regions of surgically removed degenerated discs due to loss of gross morphology, making it difficult to distinguish differences between NP and AF cells. In addition, the cell yield is low in severely degenerated discs and it is necessary to expand the cells to increase cell number, which may influence the phenotype of cells (72).

An early event and a hallmark of disc degeneration is the loss of aggrecan and any therapeutic agent used in the early stage of degeneration must increase its synthesis. Thus in the present aggrecan synthesis was focused on as the read out to evaluate the beneficial effect of the Link N fragment. However, disc degeneration in vivo is strongly associated with increased catabolism in the disc matrix. This process involves an up regulation of various cytokines and proteases likely to also be expressed early in the disease process (17, 53). It is essential for a bioactive agent with the ability to reverse or retard the degenerative process in the disc to exert its anabolic effect in this catabolic milieu. This data indicates that Link 1-8 has these properties.

It was also found that although Link N is processed by AF cells, a active sequence remains intact. Cathepsin K cleavage of Link N between residues 8-9 resulting in two peptides, Link 1-8 and Link 9-16, while MMPs 3, 7, 12, 13, ADAMTS 4,5, HTRA1, and cathepsins B, and L failed to process Link N. A role of cathepsin K in disc degeneration has been suggested (55, 73). It is not known if Link 1-8 is generated in the extracellular matrix of degenerating intervertebral discs.

It has been shown that Link N acts through the BMP type II receptor and that receptor activation leads to Smad1/5 signalling and an upregulation of BMP-4 and BMP-7 message levels (32). BMP type II receptor is the only receptor described as a partner for Link N. It is therefore likely that Link 1-8 interacts with the same receptor and as both peptides induce proteoglycan synthesis to a similar extent. If so then one would expect that Link N would also have the other metabolic properties of Link N, such as the ability to down-regulate metalloproteinase expression.

Link N 1-8 is a promising bioactive substance for the treatment of degenerative disc disease. Patients that could benefit from this treatment include for example those with early disc degeneration for example where the AF remains intact before major collagen degradation has occurred. Degeneration beyond Thompson grade 3 may require surgical treatment due to the low number of cells and the severally disrupted ECM remaining in the disc. However, Link N 1-8 might still be useful in individuals with these higher grades of degeneration, where it could be used to delay adjacent level disc disease after fusion (74-76). One advantage in using this shorter 8 amino acid peptide rather than the original 16 amino acid Link N in therapy could be the production cost The small size m also be more amenable to in vivo delivery.

TABLE 1

Identification of Human Intervertebral Disc (IVD) Donors.

| Donor | Age (yrs) | Sex | Cause of Death | Disc Levels |
|---|---|---|---|---|
| 1 | 19 | F | Cocaine Overdose | L1-L2, L2-L3, L5-S1 |
| 2 | 20 | F | MVA | T12-L1, L3-L4, L5-S1 |
| 3 | 16 | F | Cardiac Arrest | T12-L1, L1-L2, L5-S1 |
| 4 | 36 | F | MVA | T12-L1, L3-L4, L5-S1 |
| 5 | 25 | M | Suicide | T12-L1, L1-L2, L5-S1 |
| 6 | 47 | F | CVA | T12-L1, L3-L4, L5-S1 |
| 7 | 42 | F | ICH | T12-L1, L5-S1 |

ICH = Intracranial Hemorrhage,
MVA = Motor Vehicle Accident,
CVA = Cerebro-Vascular Accident.

Example 2

As demonstrated previously, Link N is released from Link protein by MMP cleavage. It is produced in both articular and intervertebral discs and promotes aggrecan/collagen synthesis by disc (NP and AF) and articular cartilage (chondrocyte) cells.

Link N stimulation of human discs in organ culture has been reported to increase proteoglycan synthesis compared to discs injected with medium alone by 1.15 to greater than 7 fold. Proteoglycan synthesis is detectable 9 days after Link N stimulation.

In a rabbit model of disc degeneration injection of Link N at a concentration of 100 micrograms of Link N in 10 microliters of saline 2 weeks after L2/3 annular puncture, significantly increased IVD disc height 14 weeks after Link N infections. Aggrecan mRNA was significantly increased in AF and NP cells (particularly in AF cells). As well MMP-3 and ADAMTS-4 proteinase expression was significantly reduced. It was demonstrated that Link N is retained in the human discus and is only lost slowly through the endplate and not AF. The specificity of Link N is sequence dependent as a scrambled Link N or reversed Link N had no effect in human NP cells or human iAF cells. See for example references 29 and 34.

Figure 3:
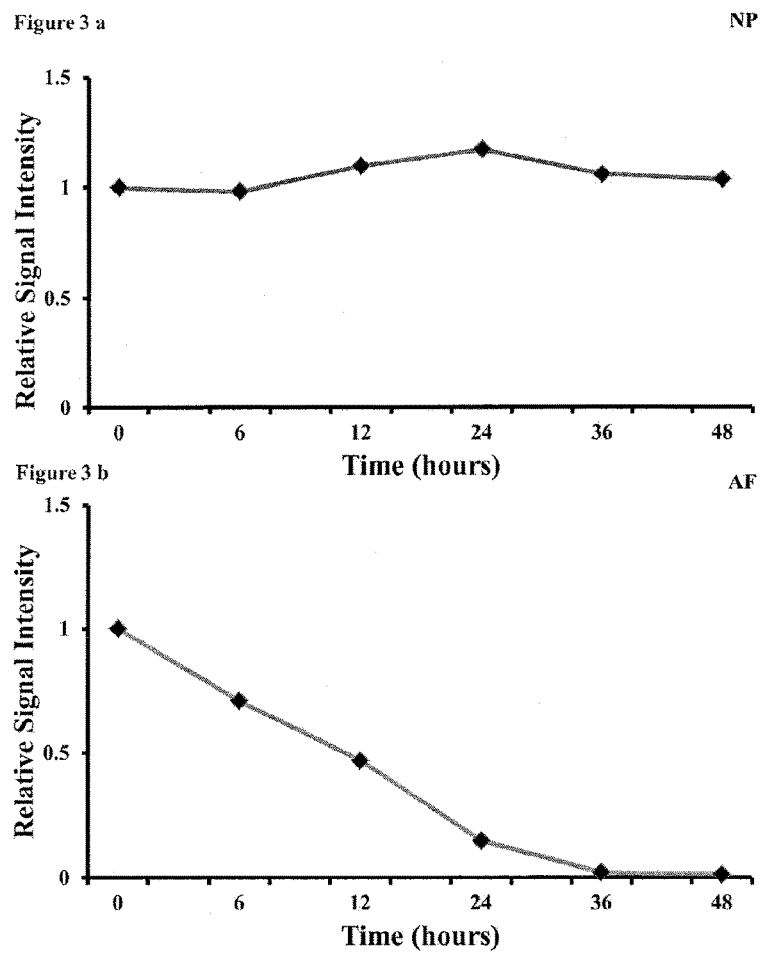
FIG. 3: Stability of Link-N in the presence of cells. Link N was incubated for 48 h at 37° C., 5% $CO_2$ in the presence of human NP (a) or AF (b) cells, and the peak intensity of the intact peptide was followed by mass spectrometry. Aliquots were analyzed at 6, 12, 24, 36 and 48 h. Data is plotted as ratio relative to signal intensity at time 0. The plot is one out of three representative experiments conducted with cells from three different donors.

The stability of Link N in culture in the presence of NP and AF was tested as shown in FIG. 3 and as described above. Link N is processed by AF cells but not by NP cells.

FIGS. 4b and 4c shows the possible Link N fragments identified by mass spectrometry. Multiple reaction monitoring of Link N peptide 1-16 after incubation with a variety of different proteinases found that the signal is lost only in the presence of cathepsin K incubation (FIG. 6A). This corresponds to the appearance of peaks as shown in FIGS. 6B and 6C. Link N 1-8 but not Link N 9-16 is active for inducing proteoglycan synthesis when contacted with human NP cells and human iAF cells (FIG. 7A). Link N 1-8 shows similar or better activity than full length Link N (FIG. 7B). Link N and Link N 1-8 but not Link N 9-16 can promote proteoglycan synthesis in an inflammatory environment.

These results show that aggrecan production is increased in both NF and AF cells, Link N is retained in the disc and only lost slowly through the endplate and not AF. Link N is processed in by AF cells and not NP cells. Link N is cleaved by cathepsin K generating the 1-8 fragment and the Link N fragment produced by AF cells is active. Line N and the fragment work in an inflammatory environment Example 3

Methodology:

Osteoarthritic (OA) cartilage was obtained from four donors undergoing total knee arthroplasty with informed consent, and OA cartilage-bone explants and OA chondrocytes were prepared from each donor. Normal human chondrocytes (PromoCell, Heidelberg, Germany) and bovine articular cartilage (12 months) were used as controls.

Explants Preparation and Treatments

Cartilage explants, approximately 1 cm$^2$, were prepared from the same donors and included cartilage with the cortical bone. Explants were cultured in DMEM supplemented with 10% heat-inactivated FBS. After 7 days under standard culture conditions, the explants were exposed to: IL-1β (5 ng/ml), Link N (1 µg/ml) and co-exposed to IL1β+Link N for 21 days with culture medium changed every three days.

Tissue Processing and Analysis

Cartilage plugs of 3 mm diameter were isolated from different areas from each explant. The expression of Col II, Agg, Col X and MMP-13 was evaluated by Western blotting. Briefly, cartilage plugs were extracted with 15 volumes (v/w) 4-M guanidinium chloride (GuCl), 100-mM sodium acetate, pH 7.4, containing proteinase inhibitors for 48 h at 4° C. An aliquot of 100 µl, used for Western blot analysis, was precipitated with 9 volumes of ethanol and incubated one hour at 37° C. with 50 mU keratanase I (Seikagaku) followed by an overnight incubation at 37° C. with 20 mU chondroitinase ABC (Seikagaku). Cartilage matrix components were resolved by SDS/PAGE on 4-20% gradient gels (Bio-Rad) under reducing conditions, and transferred to 0.2 um PVDF membranes for immunoblotting. Aggrecan was detected using a rabbit polyclonal antibody recognizing the amino-terminal G1 (anti-G1). Col II and MMP-13 were recognized with anti-Col II and anti-MMP13 rabbit polyclonal antibodies (Abcam), while type X collagen was recognized with an anti-Col X mouse monoclonal antibody (Sigma).

The total glycosaminoglycan (GAG, predominantly aggrecan) content in the tissue was quantified using the 1,9-dimethylmethylene blue (DMMB) dye-binding assay.

OA Chondrocyte Isolation and Culture

OA chondrocytes were recovered from the cartilage of each knee by sequential digestion with 0.125% Pronase followed by 0.2% Collagenase. After isolation, the cells were expanded in DMEM supplemented with 10% heat-inactivated FBS and 1% Streptomycin.

NFkB Signaling

OA and normal chondrocytes were transferred to 6-well plates and grown to 90% confluency. Cells were serum deprived overnight and incubated in culture medium containing IL-1β (5 ng/ml), Link N (1 µg/ml) or combination of the two for 10 minutes at 37° C. Cells were lysed in RIPA (radio immuno-precipitation assay) buffer and protease cocktail II (Sigma) and phosphatase (ThermoScientific) inhibitors. Lysate was electrophoresed on a 4-20% gradient gels (Bio-Rad) under reducing conditions, and transferred to 0.2 um PVDF membranes. Blots were probed with anti-phospho-NFkB antibody (Cell Signaling), and NFkB (Cell Signaling) and GAPDH (Sigma) for normalization.

Results:

Link N significantly induced proteoglycan production in the presence of IL-16, in OA explants and chondrocytes. In OA cartilage, a significant increase in proteoglycan synthesis was observed retained in the matrix in response to Link N. Similar results were obtained for Col II. Link N also suppressed MMP-13 activation and Col X expression. Interestingly, in OA and normal chondrocytes, IL-1β-induced activation of NF-κB was dose-dependently suppressed by Link N.

Figure 8:
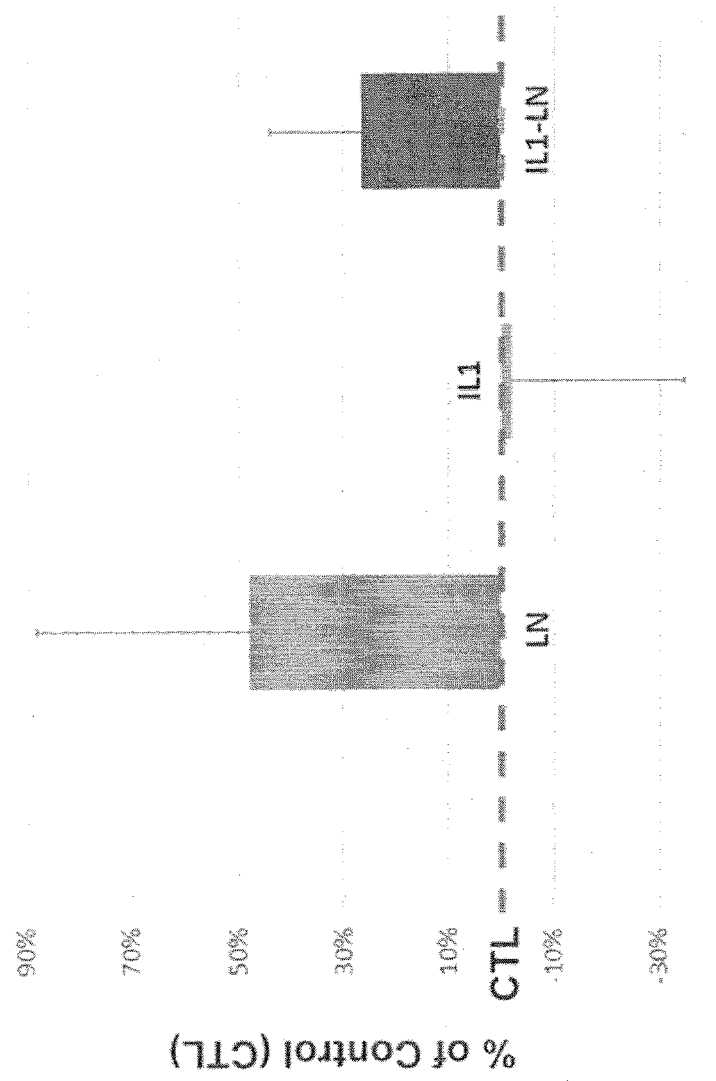
FIG. 8: Proteoglycan (GAG) concentration in human osteoarthritic (OA) cartilage in response to Link N in an inflammatory environment. Proteoglycan concentrations were determined in OA cartilage explants incubated for 21 days with Link N (1 µg/ml), IL-1-containing medium (5 ng/ml), co-exposed to Link N and IL-1, or medium without peptide supplementation (control). The results are presented as the percentage of GAG retained in cartilage, normalized to control. Values where $p \leq 0.05$ (*) were taken as significant.

FIG. 8 demonstrates that GAG is retained in OA explants treated with Link N. GAG retention was calculated as a % retention of control (CTL) explants.

FIG. 8 demonstrates that Link N significantly induced proteoglycan production in the presence of IL-1β, in OA explants and chondrocytes.

Figure 9:
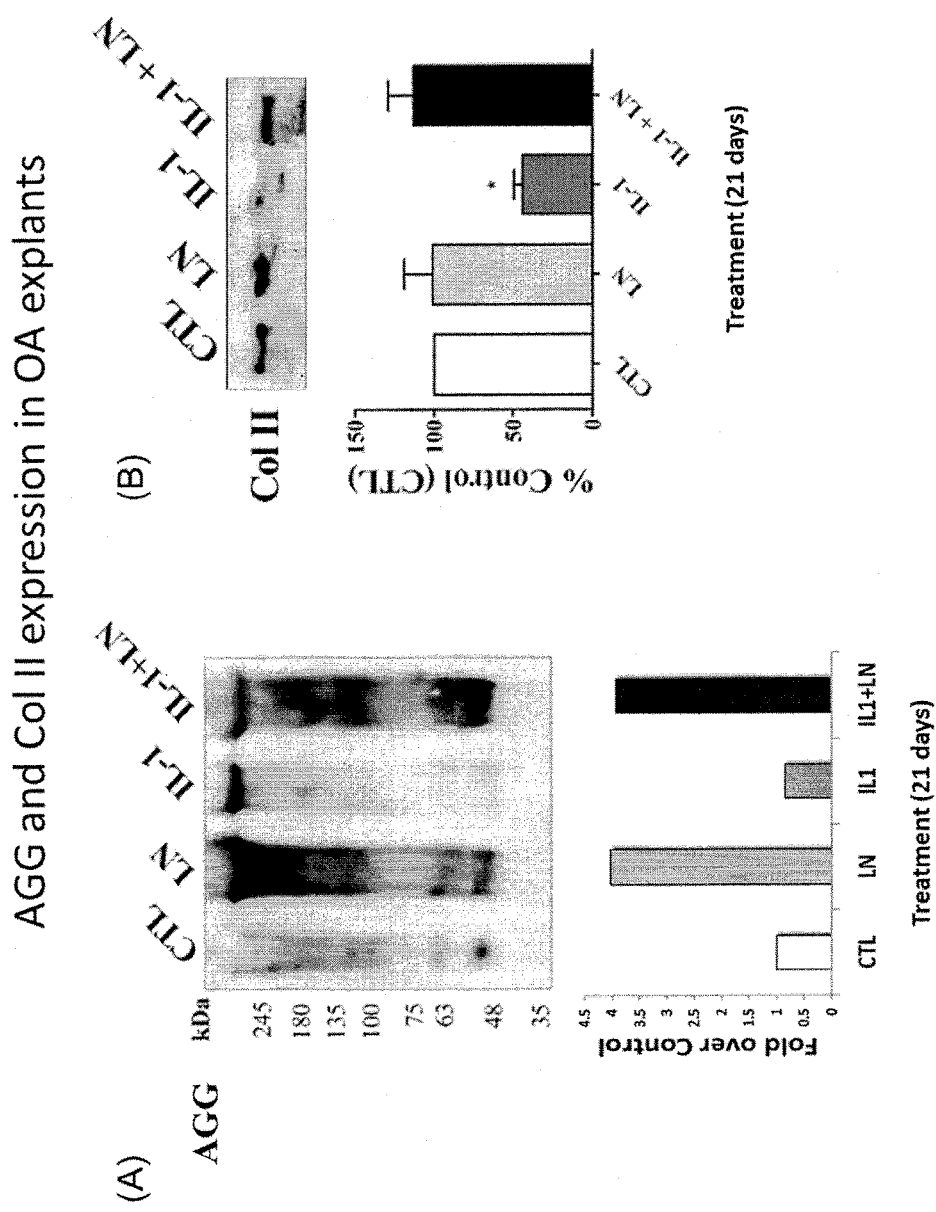
FIG. 9: Analysis of aggrecan core protein and newly synthesized type II collagen in human osteoarthritic cartilage. (A) The immunoblotting of aggrecan (AGG) core protein in control, Link N, IL-1 and both Link N and IL-1 treated cartilage and the semi-quantitative analysis of intact aggrecan core protein with a molecular weight of about 320 kDa. (B) The immunoblotting of type II collagen (Col II) in control, Link N, IL-1 and both Link N and IL-1 treated cartilage and the semi-quantitative analysis of collagen with a molecular weight of 360 kDa. The results are represented as mean±SD of four cartilage samples from different donors (*p<0.05).

FIG. 9 demonstrates that in OA cartilage, a significant increase in aggrecan synthesis is observed and retained in the matrix in response to Link N. Similar results are obtained for Col II.

Figure 10:
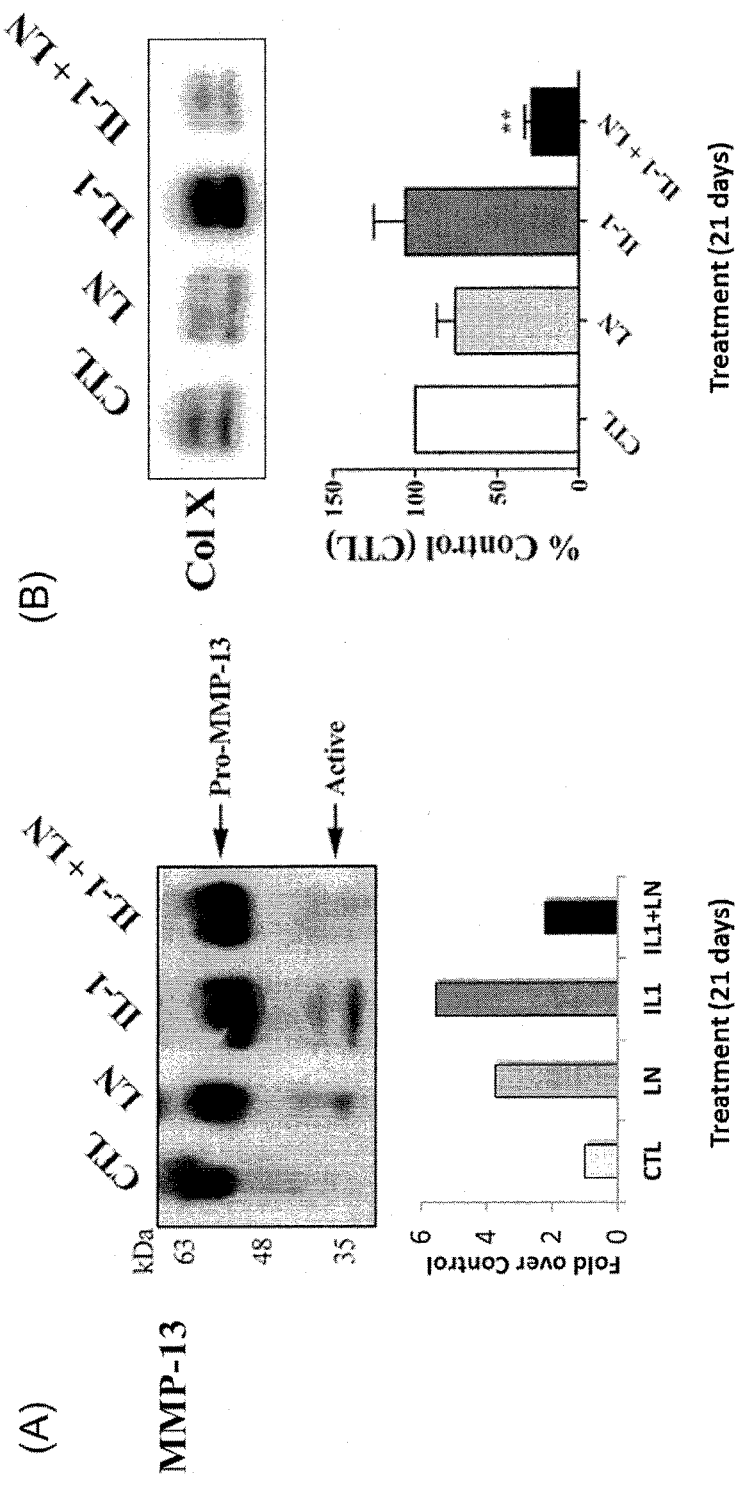
FIG. 10: Analysis of MMP-13 and type X collagen (Col X) expression in human osteoarthritic cartilage. (A) The immunoblotting of MMP-13 in control, Link N, IL-1 and both Link N and IL-1 treated cartilage and the semi-quantitative analysis of MMP-13 protein with a molecular weight of 55 kDa. (B) The immunoblotting of type X collagen in control, Link N, IL-1 and both Link N and IL-1 treated cartilage and the semi-quantitative analysis of collagen alpha chains with a molecular weight of 60 kDa. The results are represented as mean±SD of four cartilage samples from different donors (*p<0.05).
Figure 11:
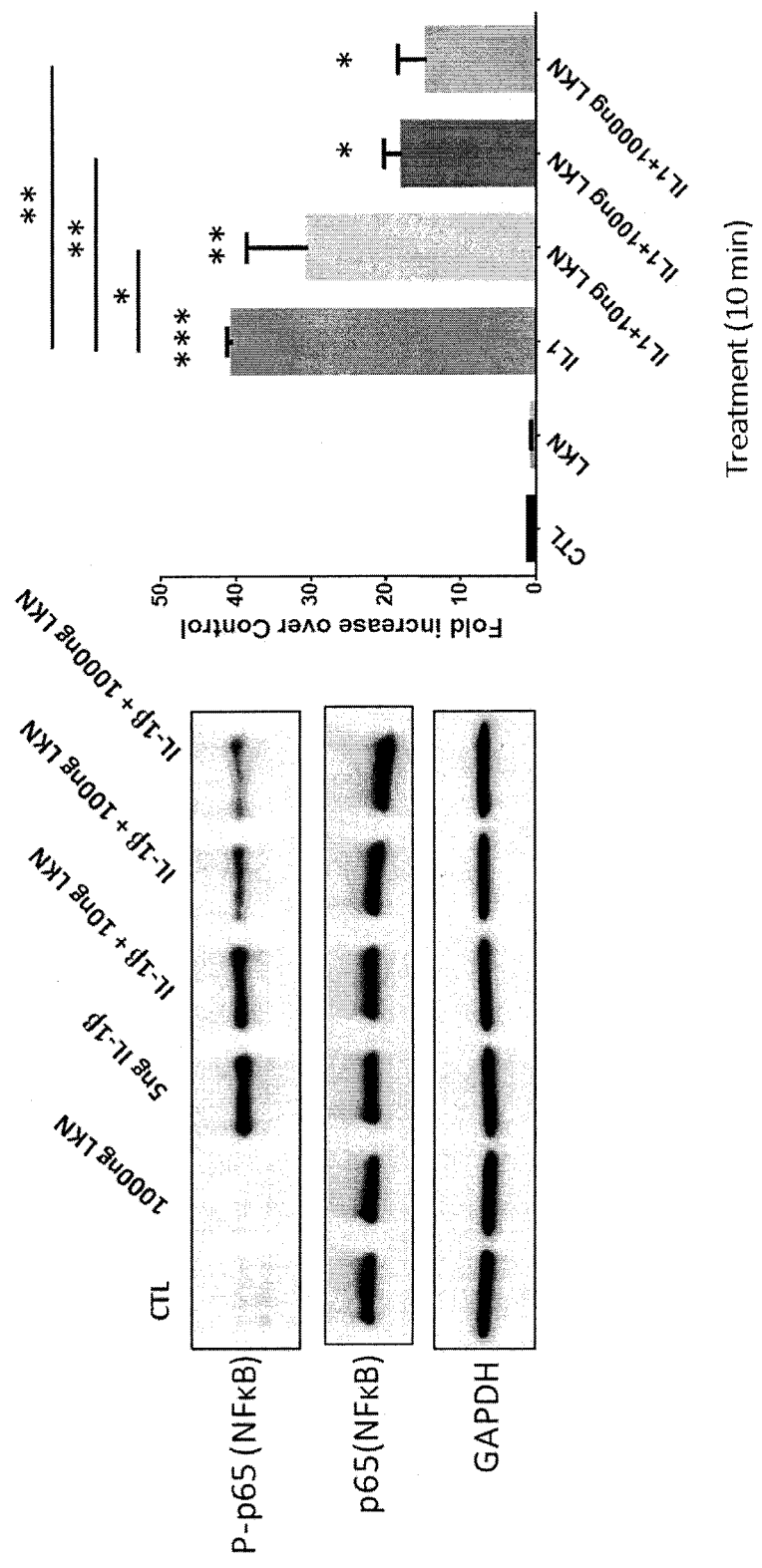
FIG. 11: Analysis of NFkB in chondrocytes from OA and normal donors supplemented with Link N in an inflammatory environment. Western blot analysis of NFkB in chondrocytes control, Link N treated, IL-1 treated, Link N (10 ng/ml)+IL-1, Link N (100 ng/ml)+IL-1 and Link N (1000 ng/ml)+IL-1. The results are represented as mean±SD of three experiments from different donors (*p<0.05). The results demonstrate that IL-1 induced activation of NF-kB is dose dependently suppressed by Link N in normal human chondrocytes (A) and OA chondrocytes (B).
Figure 11:
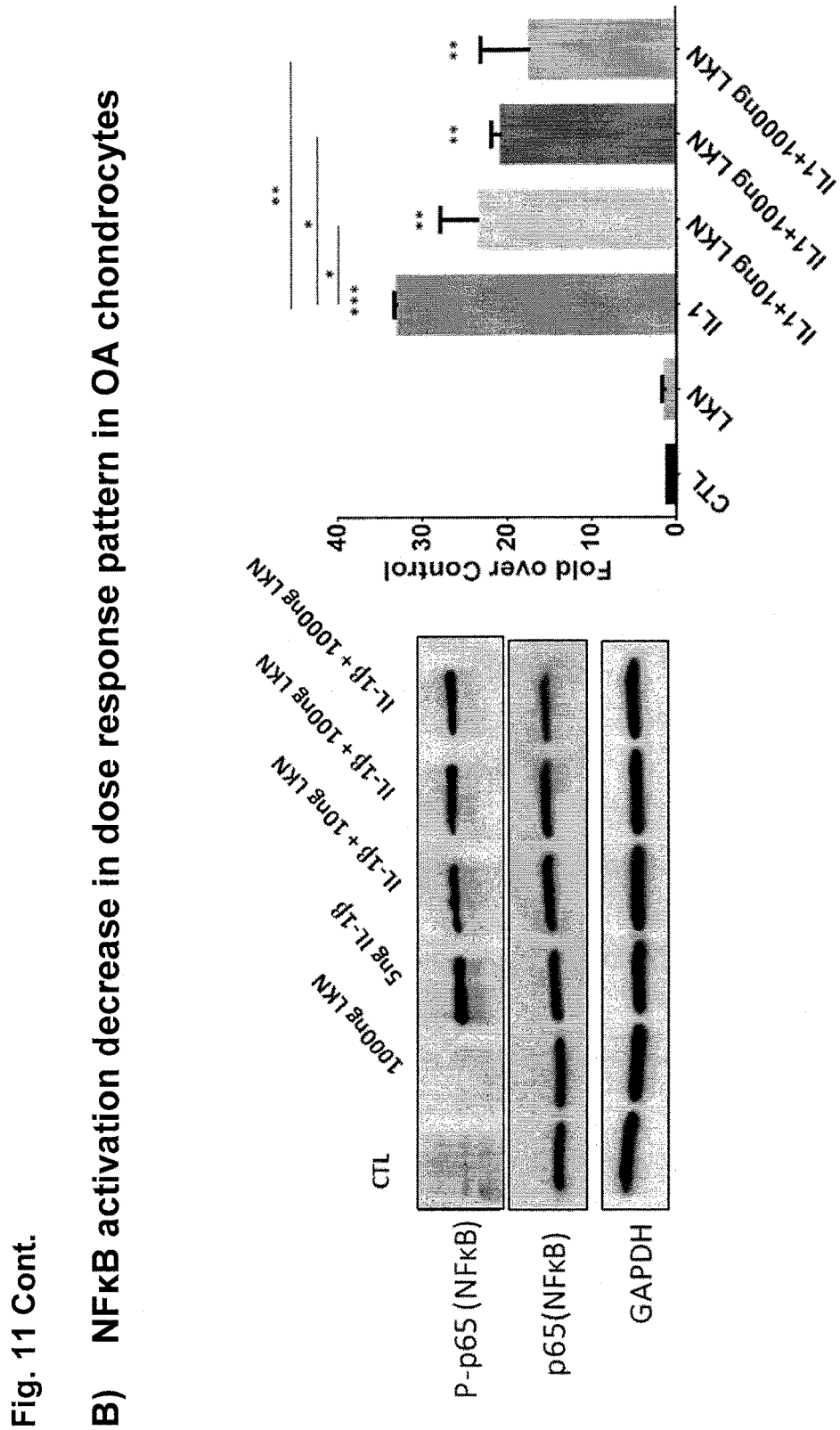

FIG. 10 demonstrates that Link N suppresses IL-1β induced MMP-13 activation (A) and Col X expression (B) and FIG. 11 demonstrates that IL-1β induced activation of NF-kB is dose dependently suppressed by Link N in normal human chondrocytes (A) and OA chondrocytes (B).

Accordingly Link N stimulates the retention of proteoglycan in osteoarthritic cartilage and can stimulate proteoglycan and collagen in an inflammatory environment. Link N can suppress the active form of MMP-13 in osteoarthritic cartilage and Link N suppresses IL-1 beta induced protease expression, and without wishing to be bound by theory for example through downregulation of NFkB.

OA is closely linked to the presence of inflammatory cytokines in vivo. It is demonstrated that Link N can induce proteoglycan synthesis in an inflammatory environment in the intervertebral disc. It is however, not known if Link N can restore proteoglycan content in osteoarthritic cartilage in an inflammatory milieu. To test this, human explants from osteoarthritic cartilage were cultured for 21 days with Link N, in the presence of IL-1β, with a combination of Link N and IL-1β, or medium alone. The concentration of extractable proteoglycans was quantified by the DMMB assay. Link N increased the GAG content of the explants to about 50% when normalized to the control. IL-1β decreased the proteoglycan concentrations when compared to the control. However, Link N increased the GAG content of the explants to about 30% in the presence of IL-1β when normalized to the control. This indicates that during cartilage degeneration Link N has the potential to restore proteoglycan and that the effect is sustained in an inflammatory environment.

The effect of Link N on the synthesis and retention of aggrecan in the tissue using an antibody against the G1 domain was next analyzed. After culturing the explants for 21 days in the absence of supplements, explants show weak aggrecan G1 containing fragments. With Link N supplementation, the content of aggrecan G1 containing fragments is increased significantly ($P<0.0001$). When explants were treated with IL-1 alone the intensity of the staining of aggrecan G1 containing fragments was similar compared to that of the control although few of the lower molecular weight fragments were observed whereas the supplementation of Link N and IL-1 significantly increased the quantity to a level comparable to the Link N alone treated explants.

Since the G1 domain bands are produced by aggrecanases and MMP activity in cartilage in vivo as a result of ongoing metabolism of the matrix, the effect of Link N on MMP-13 expression in an inflammatory milieu was next tested. MMP-13 expression was analyzed by western blotting after culturing explants in the absence or presence of Link N alone, Il-1 alone or together with Link N. After culturing the explants for 21 days in the absence of supplements, explants show weak active MMP-13. Link N significantly induced active MMP-13 when compared to controls. With Il-1 supplementation, active MMP-13 is increased more than that stimulated by Link N. In contrast, adding Link-N in the presence of IL-1β led to a decrease in the quantities of the active form of MMP-13 when compared to IL-1β alone. Thus Link N suppresses the active form of MMP-13, in an inflammatory milieu.

Cartilage repair also requires collagen production to generate a stable matrix. Therefore, the levels of recently produced extractable type II collagen were assessed. The quantity of type II collagen extracted from the osteoarthritic control explants was lower than in Link N supplemented explants although not significant. When the explants were treated with Il-1 alone, the quantities of type II collagen were decreased significantly when compared to control explants. In contrast, adding Link-N in the presence of IL-1β led to an increase in the quantities of type II collagen when compared to IL-1β alone. Thus Link N not only stimulated aggrecan production, in an inflammatory milieu but also that of type II collagen.

Several studies have shown that many genes encoding pro-inflammatory cytokines and matrix degrading enzymes are regulated by the transcription factor, nuclear factor-kappa B (NF-κ B). Suppression of the NF-κ B activating cascade using Link N could down-regulate the expression of pro-inflammatory mediators.

The effect of Link N on NF-κ B activation by IL-1 in normal chondrocytes was next assessed. Normal chondrocytes from were stimulated with IL-1β in the presence or absence of varying concentrations of Link N. Stimulation of phosphorylated NF-kappaB RelA (p65) was determined by western blotting using antibodies specific to P-P65(NF-kB). After culturing chondrocytes cells in the absence of IL-1β, chondrocytes show no P-P65(NF-kB) protein. With Link N supplementation, no effect on P-P65(NF-kB) protein was observed. As expected, P-P65(NF-kB) is prominent after stimulation with IL-1β. Link N significantly inhibited IL-1β stimulated P-P65(NF-kB) in a dose-dependent manner—100 ng of Link N was very similar to 1000 ng Link N. Similar results were observed when chondrocytes from OA patients were used. This data demonstrates that Link N suppresses IL-1beta mediated NF-kB activation and may suppress IL-1β stimulated MMP-13 and inflammatory cytokines by inhibiting NF-κB signaling.

Discussion

Articular cartilage architecture is kept intact and functional through anabolic and catabolic factors, which act on the chondrocytes that in turn maintain tissue homeostasis by balancing synthesis and degradation. Degradation and loss of collagen and aggrecan, subchondral bone remodeling, and inflammation of the synovial membrane characterize osteoarthritis, as the balance shifts to catabolism. It has previously been reported that Link N can stimulate collagen and proteoglycan synthesis in chondrocytes. It is however, not known if Link N can restore proteoglycan and collagen content in osteoarthritic cartilage in an inflammatory milieu. The results herein demonstrates that in early OA, Link N has the potential to restore proteoglycan and collagen content. The data also indicate that Link N can also suppress proteolysis, increase proteoglycan and collagen synthesis by inhibiting NF-κB signaling even in an inflammatory milieu.

Link N, a bioactive factor, has been demonstrated to have the potential to stimulate disc repair. It has been identified using isolated IVD cells in vitro, to induce collagen and proteoglycan message levels and has been reported to increase incorporation of radioactive $^{35}SO_4$ into newly synthesized proteoglycans (6,16,18). Indeed, Link N injection into intact human IVDs ex vivo resulted in increased incorporation of radioactive $^{35}SO_4$ in newly synthesized proteoglycans, and led to partial restoration of disc height when injected into rabbit discs in a stab model of disc degeneration. The results indicate that Link N can stimulate proteoglycan and collagen expression in chondrocytes from OA patients, consistent with a functional role in restoring the functional properties of cartilage.

Link N suppressed the activation of P-P65(NF-kB) in chondrocytes. NF-kB signaling pathways play active roles in the development and progression of arthritis in vivo (19,20). Indeed, our studies showed the activation of NF-kB in articular chondrocytes following stimulation with IL-1b, which plays an important role in the catabolism of the articular cartilage. NF-kB expression correlated with collagenase-3 (metalloproteinase (MMP)-13) and stromelysin 1 (MMP-3) levels. Also, a shift to nuclear NF-kB localization was shown in chondrocytes during cartilage destruction in the early stage of arthritis in DBA/1 mice immunized with type II collagen. The present results show that stimulation with IL-1b causes stimulation of NF-kB activation in articular chondrocytes In order to have a functional matrix newly laid down matrix has to be remodeled. This involves upregulation of various proteases. In this study Link N significantly suppressed active MMP-13 when compared to controls. Thus in order to remodel the newly synthesised ECM for its new function within the cartilage, upregulation of the proteases is required. Human disc cells supplemented with Link N upregulate proteases in vitro and in a rabbit in vivo model of disc degeneration. Thus, Link N appears to be effective at stimulating repair of the cartilage, involving remodelling of the disc ECM to restore the function of cartilage.

The potential use of inhibitors of NF-kB to reduce articular cartilage degradation by MMPs in arthritis has been described. Favorable results using nonsteroidal anti-inflammatory drugs (NSAIDs), glucocorticoids, and different agents demonstrate decreased NF-kB activation. However, the use of NSAIDs can result in gastrointestinal side effects and the lack of specificity in antisense and transcription factor decoy strategies present a big challenge when targeting gene expression is to be inhibited in only a single organ.

Furthermore, the problems of protein delivery, immunogenicity, and cost of treatment have limited the realistic prospect of whole proteins for therapy.

Example 4

An organ culture model of early disc degeneration, involving proteoglycan depletion but no substantial collagen disruption is used to study the effect of molecular and cell-based therapies, using Link. N as an economic growth factor analog and mesenchymal stem cells (MSCs) as a cell supplement.

Materials and Methods

Mesenchymal Stem Cell Culture

Human MSCs harvested from bone marrow were obtained from Lonza (Basel, Switzerland). According to the supplier, the cells were positive for CD105, CD166, CD29, and CD44 and negative for CD14, CD34, and CD45. In addition, the cells were confirmed to be able to differentiate into osteogenic, chondrogenic, and adipogenic lineages. All cells were expanded in Dulbecco's modified Eagle's medium (DMEM) supplemented with 10% fetal bovine serum (FBS), 100 U/mL penicillin, and 100 µg/mL streptomycin and were used within four passages (19,20). All culture reagents were from Wisent Inc. (St-Bruno, Canada).

Mesenchymal Stem Cell Labeling and Tracking

MSCs were labeled with PKH67 (Sigma-Aldrich, Oakville, Canada) following the instructions of the supplier. Briefly, $2 \times 10^6$ MSCs were washed with DMEM without FBS and collected as a loose pellet by centrifugation at 400 g for 5 min. The pellet was re-suspended in Diluent C and quickly mixed with the dye solution. The cell/dye suspension was then incubated for 5 min, whereafter the reaction was stopped by adding an equal volume of FBS. Viability of the cells was measured by staining with trypan blue. An aliquot was cultured in monolayer (Sarstedt, Saint-Léonard, Canada) for two days to track the labeling efficiency. The remainder of the cells were re-suspended in either phosphate-buffered saline (PBS) (Wisent), or in PBS supplemented with 1 mg/mL Link N (CanPeptide, Montreal, Canada). The cell suspension was then injected into bovine discs pretreated with trypsin to induce degeneration (21).

Disc Isolation and Culture

The largest first 3-4 caudal discs were isolated from the tails of 24- to 30-month-old steers, as described previously (21,22). Briefly, the tails were dissected free of skin, muscles and ligaments, and pedicles for each segment were removed. The bone and the adjacent calcified part of the cartilaginous endplate were removed, so that the surface of the disc was soft and flexible without detectable calcified tissue. After the discs were rinsed in PBS supplemented with 1,000 U/mL penicillin, 1,000 µg/mL streptomycin and 0.25 µg/mL fungizone (GIBCO, Burlington, Canada), they were preconditioned for 3 days in sterile 80 mL specimen containers (STARPLEX Scientific, Etobicoke, Canada) containing 50 mL culture medium. (DMEM with 2 mM Glutamax and 25 mM Hepes, supplemented with 5% FBS, 100 U/mL penicillin, 100 µg/mL streptomycin, 50 µg/mL L-ascorbate). Degeneration was induced by a single injection of 100 µg trypsin (Sigma-Aldrich) dissolved in 75 µL PBS into the center of the disc using a 28 G½ needle (21) The needle was placed on top of the disc to measure the distance needed to reach the center and was then inserted to the same depth. Once in the center, the trypsin solution was slowly injected and the needle was then gradually pulled out to avoid back flow. The discs were then cultured for another 4 days, before injection of MSCs ($10^5$ cells), Link N (75 µg), or a combination of MSCs ($10^5$ cells) and Link N (75 µg) in a final volume of 75 µL PBS. The Link N concentration was based on the optimal dose for isolated bovine disc cells (1 µg/ml) assuming an average volume of the bovine discs to be 7.5 mL. The number of MSCs used was based on a study by Liebscher et al (23), which measured the cell density of healthy human discs. About half the number of cells found in a healthy adult human disc were used in this study, in order to avoid a potential detrimental effect on cell survival due to nutrient deprivation as the bovine discs already have a high cell density. For all experimental conditions, seven discs were injected. Seven of the trypsin-treated discs were injected with PBS alone to serve as degeneration controls and to verify that the trypsin was active in degrading the proteoglycan content of the NP. Seven discs were cultured without any injection to serve as non-degeneration controls. The discs were then cultured for 14 days and the media were changed every 3 days.

Analysis of Discs by Microscopy and Histology

At termination of culture two sections were taken through the center of the discs using an in-house designed cutting tool consisting of two microtome blades (21). This gives two 750 µm thick slices about 3 cm wide (disc diameter) and 1 cm high (disc height). One slice was fixed in formalin-free fixative (Accustain, Sigma-Aldrich) for histology analysis. Fixed samples were embedded in paraffin wax and 5-µm-thick sections were cut and stained with hematoxylin and Safranin 0-fast green (24). The other slice was used fresh to study the distribution of MSCs in the disc tissue. The labeled stem cells populating the discs were visualized using an inverted confocal laser scanning microscope (CLSM, Zeiss LSM 510). Twenty consecutive 6 µm sections were imaged, and CLSM stacks were split into single images.

Extraction of Extracellular ECM Proteins and Proteoglycans

The remaining nucleus pulposus (NP) tissue was collected and the wet weight was recorded (21). The tissue was cut into small pieces and suspended in 14 volumes of extraction buffer [4 M guanidinium chloride, 50 mM sodium acetate, pH 5.8, 10 mM EDTA, COMPLETE® (Roche, Laval, Canada) for protein and proteoglycan extraction. The tissue was extracted with continuous stirring at 4° C. for 48 hours, and the extracts were cleared by centrifugation at 12,000 g for 30 min at 4° C. The supernatants were collected and stored at −80° C. for further analysis.

GAG Analysis

Sulfated glycosaminoglycans (GAGs) were quantified in tissue extracts by a modified dimethyl methylene blue (DMMB) dye-binding assay (25,26). Samples were diluted to fall within the middle of the linear range of the standard curve. Extraction buffer of an equal volume as the tissue extracts was added to the standard curve to compensate for possible interference.

Proteoglycan Analysis by Agarose Gel Electrophoresis

Proteoglycan composition was analyzed by agarose gel electrophoresis (27). Proteoglycans in 10 µL aliquots of disc extracts were precipitated with anhydrous ethanol and dissolved in distilled water. The samples were mixed with sample buffer (0.1 M Tris-HCl, 0.768 M glycine, 0.01% Bromophenol blue, 1.2% glycerol, 0.05% SDS, pH 8.3) and boiled for 10 min. The proteoglycans were separated by electrophoresis in 1.2% agarose gels. The gel was stained with 0.02% (w/v) Toluidine blue in 3% acetic acid with 0.5% (w/v) Triton X 100, and destained with 3% acetic acid then distilled water.

Aggrecan and Type II Collagen Analysis by Western Blot

Proteins and proteoglycan in 10 µL aliquots of disc extracts were precipitated by the addition of 9 volumes of anhydrous ethanol, washed twice in 95% ethanol, and finally lyophilized. Samples for analysis of type II collagen were dissolved in distilled water. Samples for analysis of aggrecan were dissolved in buffer (0.05 M Tris-HCl, with 0.03M Sodium acetate, pH 7.4, COMPLETE®), and digested by keratanase I and chondroitinase ABC (Amsbio, Lake Forest, Calif., US). The samples from the same treatment group were pooled, mixed with SDS sample buffer, and boiled for 10 minutes. Then the proteins were separated by SDS-PAGE (4-12% Bio-Rad® gels) under reducing conditions. Separated proteins were transferred to nitrocellulose membranes which were blocked with 1% BSA in PBS with 0.2% Tween 20 (blocking buffer). Then they were incubated with the primary antibodies at a 1:2,000 dilution in blocking buffer at 4° C. overnight, followed by incubation with the secondary antibody conjugated with horseradish peroxidase (1:5,000 dilution, Sigma-Aldrich) in blocking buffer. The primary antibody recognizing collagen type II was from Abcam (Toronto, Canada); the primary antibody recognizing the aggrecan G1 domain was prepared as described previously (28). The bound antibody was visualized by chemiluminescence (GE Healthcare Baie d'Urfe Canada) and analyzed using a Bio-Rad VersaDoc image analysis system (Bio-Rad, Mississauga, Canada).

Statistical Analysis

Statistical analysis was performed by using analysis of variance followed by Fisher protected least significant difference post hoc test by using GraphPad Prism (GraphPad Software, Inc. La Jolla, Calif. USA). Results are presented as the mean±standard deviation (SD) of seven independent experiments with discs from different bovine tails. Differences were considered statistically significant where $p<0.05$.

Results

Figure 12:
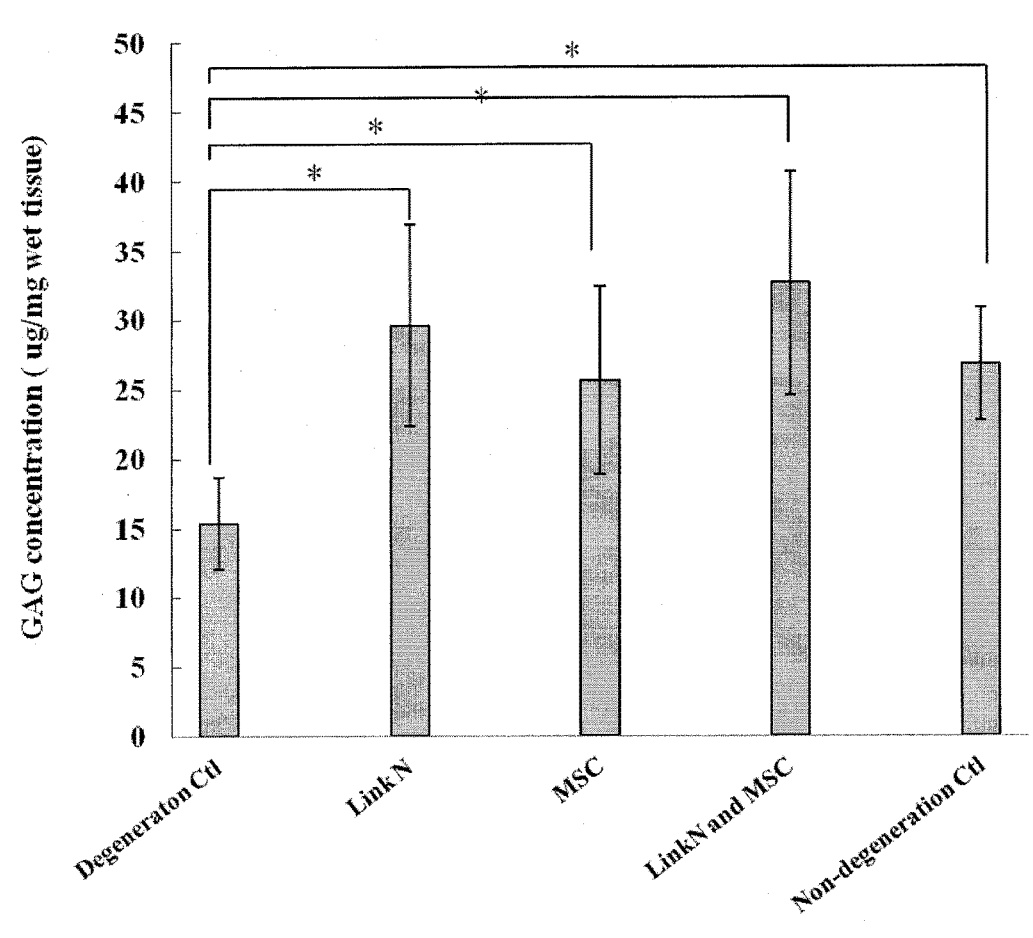
FIG. 12: Proteoglycan concentration in the discs. Proteoglycan concentrations were determined in discs with induced degeneration, discs treated with Link N, MSCs, both Link N and MSCs, and non-degeneration control discs. The results are represented as mean±SD of seven discs from different bovine tails. (*p<0.05)

Link N is known to induce proteoglycan synthesis by isolated disc cells and in degenerate rabbit discs, and to enhance chondrogenesis of MSCs in vitro (20,29-32). It is however, not known if Link N or MSCs alone can restore the proteoglycan content in larger discs with early degeneration. It is also not known if a combination of Link N and MSCs would have an additive effect. To test this, bovine discs with proteolytically induced aggrecan depletion were treated with Link N or MSCs alone or with a combination of Link N and MSCs. The discs were cultured for a 2 week period after treatment and the concentration of extractable proteoglycans was quantified by the DMMB assay (FIG. 12). Without intervention the GAG content in degenerate discs dropped to about 50% of that in non-degenerate controls. In contrast, Link N and MSCs alone, or in combination, significantly increased the GAG content of the discs compared to the GAG content in degeneration control discs ($p<0.05$). The proteoglycan concentrations in treated discs were similar to that in non-degenerated discs. However, no statistical significance was observed amongst the treated groups ($p>0.05$). This indicates that in early degeneration either Link N or MSCs alone have the potential to restore proteoglycan to its original level and no additional benefit is achieved by a combination therapy.

Figure 13:
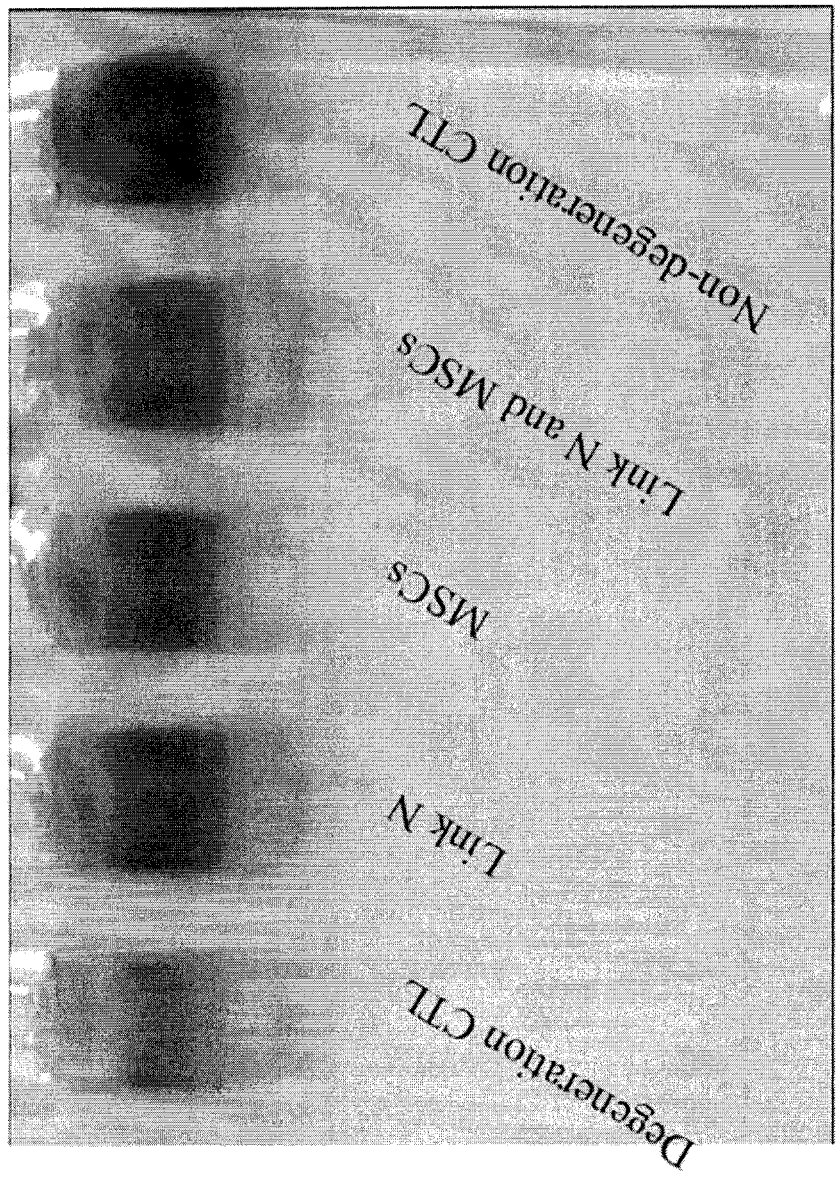
FIG. 13: Size distribution of proteoglycans in the discs. The proteoglycan isolated from seven discs with different treatments was pooled and analyzed by agarose gel electrophoresis. Proteoglycan was visualized by Toluidine blue staining.

Having equal proteoglycan content does not necessarily imply that the structure is the same as that in the normal disc. To address this, extracted proteoglycans were analyzed by agarose gel electrophoresis. The size distribution and intensity of staining in the treated discs is equivalent to that of non-degenerated control discs, whereas the intensity of the staining was lower in degeneration control discs (FIG. 13). The data demonstrates that the newly synthesized proteoglycans produced in the treated discs are of the same size range as those of the non-degenerate discs.

In addition, the presence and abundance of intact aggrecan core protein was evaluated by SDS-PAGE. Intact aggrecan core protein with a mass larger than 250 kDa was significantly lower in degeneration control discs compared to non-degenerated control discs ($p<0.05$), whereas the injection of Link N and/or MSCs significantly increased the quantity to a level comparable to the non-degenerate control discs (FIG. 14).

Figure 15:
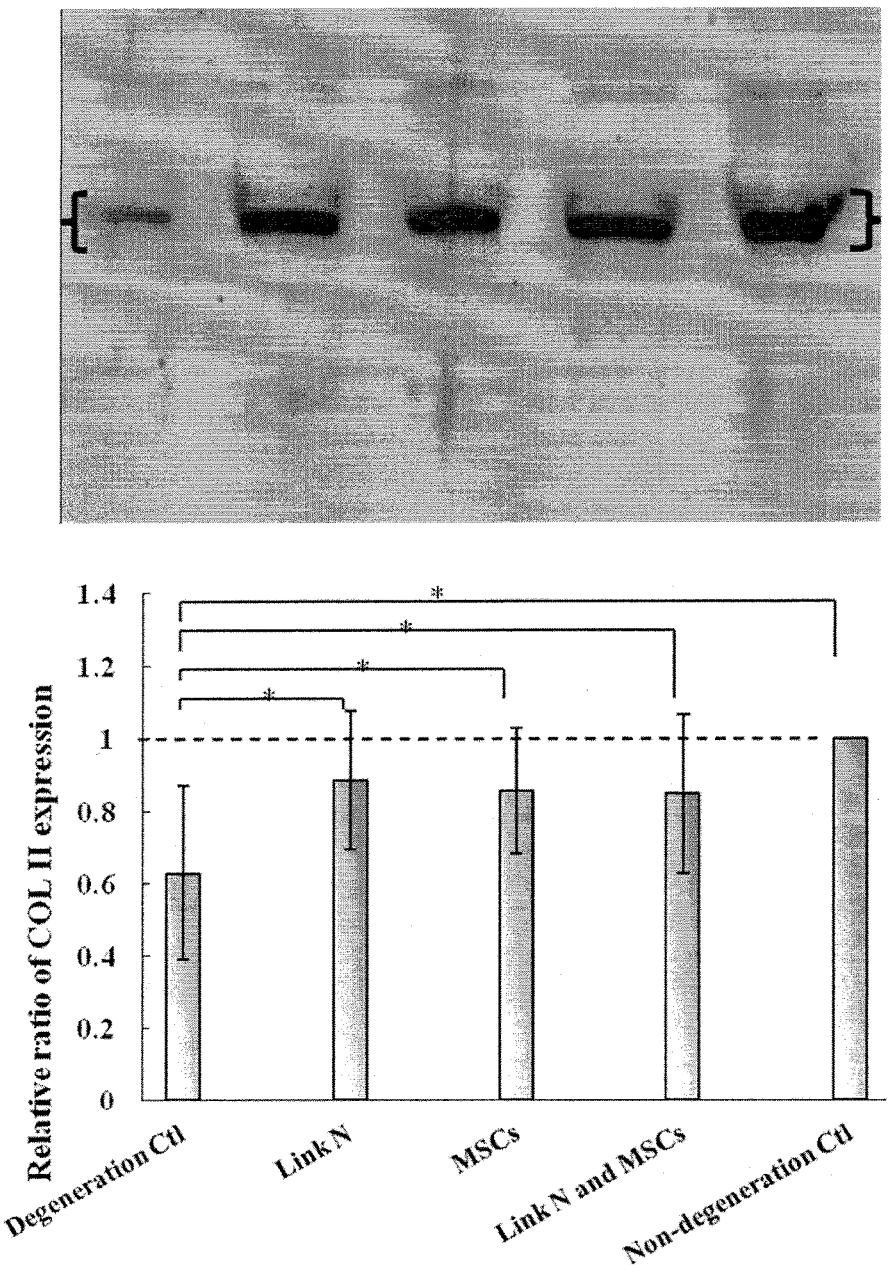
FIG. 15. Analysis of newly synthesized type II collagen in the discs. Immunoblotting and semi-quantitative analysis of type II collagen alpha chains with a molecular weight of 120 kDa in degeneration control, Link N treated, MSCs treated, both Link N and MSCs treated, and no degeneration control discs. The results are represented as mean±SD of seven discs from different bovine tails. (*p<0.05)

Disc repair also requires collagen production to generate a stable matrix. Therefore, the levels of recently produced extractable type II collagen were assessed (FIG. 15). The quantity of type II collagen extracted from the degeneration control discs was significantly lower than in non-degenerated control discs. When the discs were injected with MSCs and/or Link N, the quantities of type II collagen were increased to a similar level to that detected in non-degenerate control discs. Thus both Link N and MSCs not only stimulate aggrecan production, but also that of type II collagen.

Figure 16:
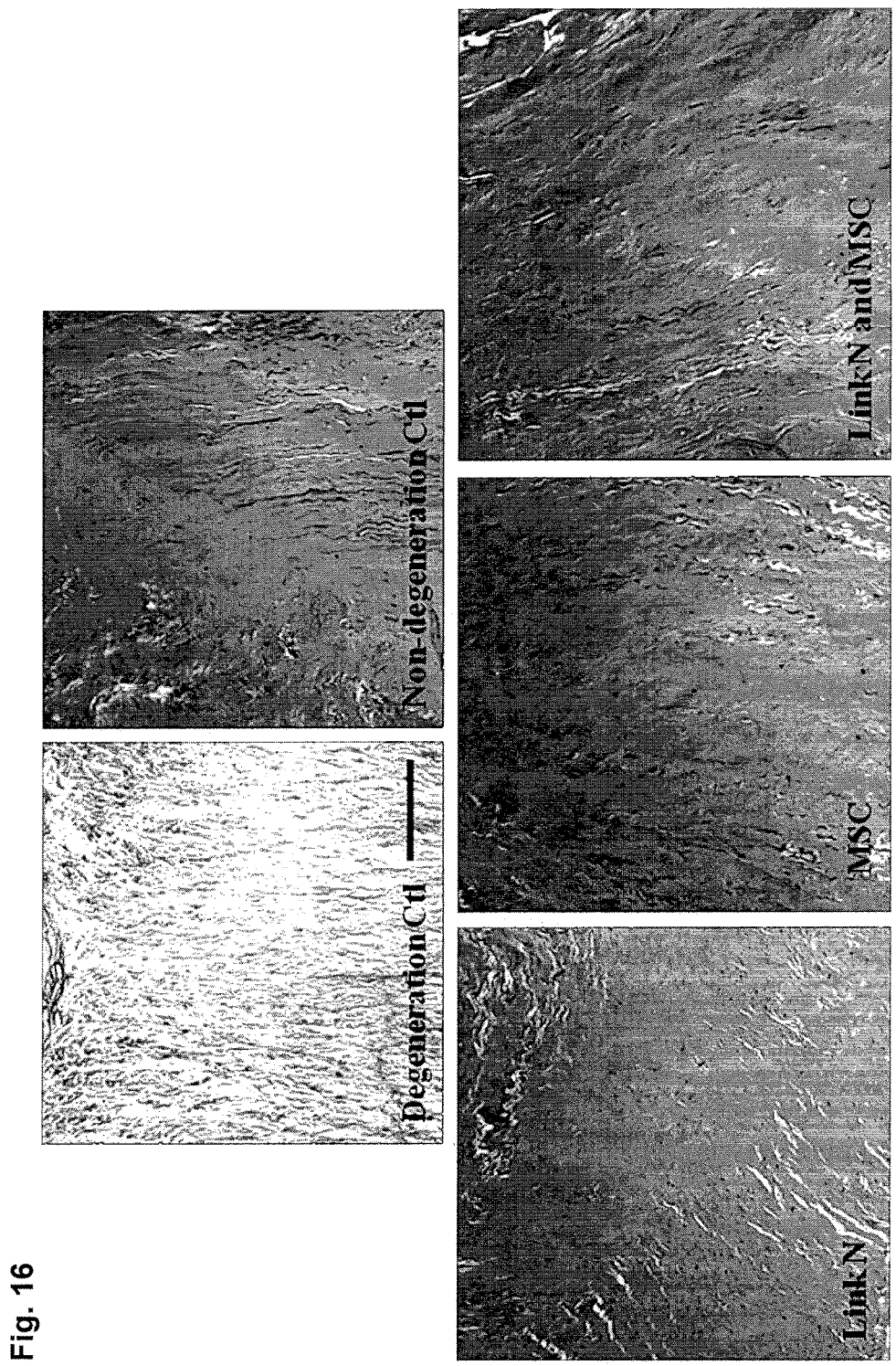
FIG. 16: Proteoglycan distribution in the nucleus pulposus region of the discs. Discs with trypsin-induced degeneration were cultured for 14 days following injection with: Link N, MSC or Link N and MSCs. These were compared with degeneration control and non-degeneration control discs. The discs were evaluated by histology using Safranin O staining (scale bar, 100 µm).

Histological analysis was used to evaluate proteoglycan distribution within the repair tissue. Safranin O and fast green staining of tissue sections confirmed a uniform loss of proteoglycans in the degeneration control discs, where little Safranin O (red) staining was found (FIG. 16). The results further confirmed that the proteoglycan content in degeneration control discs was depleted throughout the NP region. In the discs treated with MSCs or Link N alone or together, the intensity and distribution of the Safranin O staining showed an even distribution throughout the NP region, similar to that of non-degeneration control discs. Thus the newly synthesized proteoglycan was able to diffuse throughout the ECM and restore tissue content even in areas remote from the cells.

Figure 17:
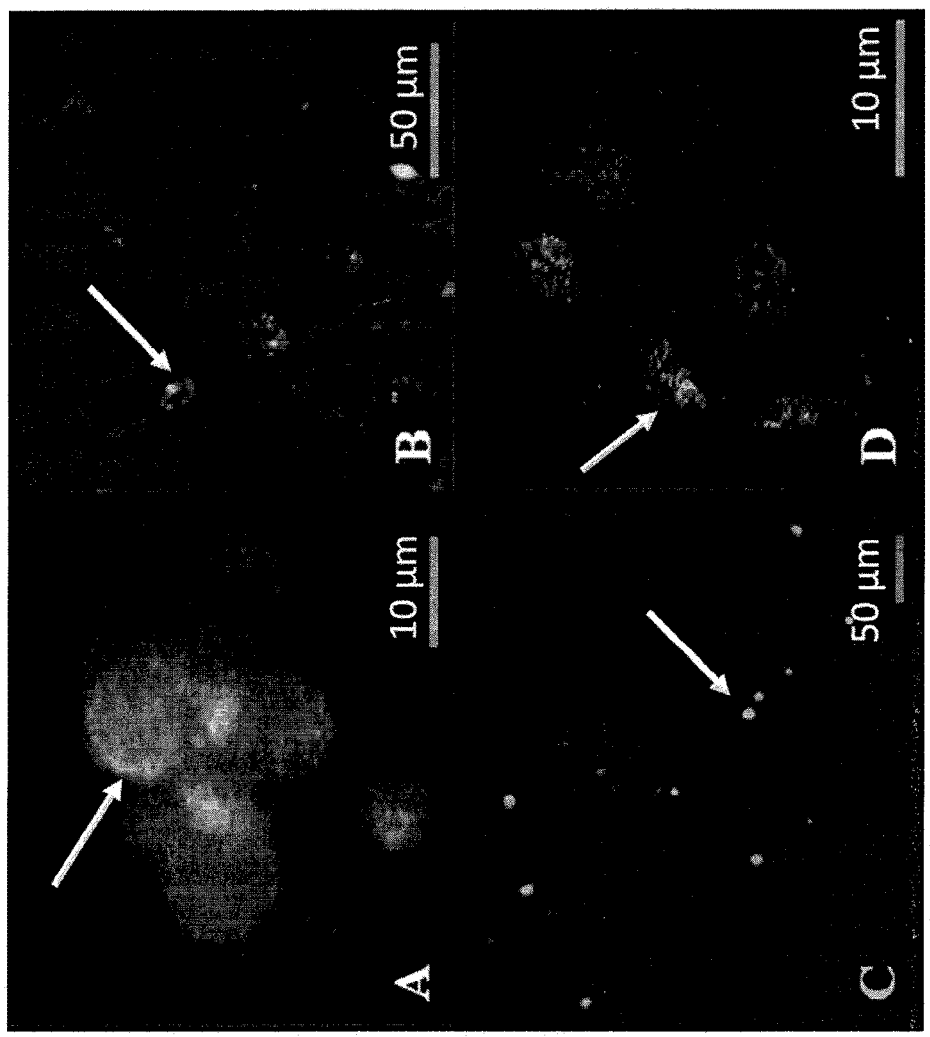
FIG. 17: Labeling and tracking of the MSCs. A. MSC cell membranes were labeled using the PKH67 kit (green fluorescence, arrow) and the labeling efficiency was evaluated using fluorescence microscopy. B. Labeled MSCs were cultured in expansion medium for two days and maintained labeling was verified using fluorescence microscopy. C. The presence of labeled MSCs was determined in the NP region after 14 days in organ culture. D. Magnification of C.

For MSC induced repair processes to be sustained the injected stem cells need to remain viable and distributed throughout the repair tissue. To address this, MSCs were labeled with PKH67 (FIG. 17A,B) and cultured for two days in monolayer to evaluate labeling efficiency and dye sustainability. MSC viability was higher than 90% when the cells were labeled and suspended in PBS or Link N/PBS solution prior to injecting into the trypsin-treated discs. To evaluate if the injected MSCs survived and integrated in the ECM of the discs, cells were traced by confocal microscopy. Labeled MSCs were found distributed throughout the NP region after the two week organ culture period, (FIG. 17C,D) indicating the feasibility of a sustainable repair process.

Discussion

In the present study an organ culture model of early disc degeneration was used to study the potential of molecular and cell-based therapies to restore IVD proteoglycan content. Link N was used as a molecular agent and MSCs as a cell supplement. The degenerate discs were treated with either therapy separately or in combination, and the results revealed that Link N or MSCs alone have the ability to restore tissue proteoglycan and that no additional effect was observed by a combination of the two.

Previous work has demonstrated the potential of Link N to stimulate disc repair (20,29,31-35). Although, Link N is cleaved by AF cells as shown herein, the resulting N-terminal 8 amino acid peptide appears to be proteolytically stable and retains biological activity. Studies utilizing isolated IVD cells in vitro, showed that Link N could induce collagen and proteoglycan message levels and result in increased incorporation of radioactive $^{35}SO_4$ into newly synthesized proteoglycans (34,35). In addition, Link N injection into intact human IVDs ex vivo (34) resulted in increased incorporation of radioactive $^{35}SO_4$ in newly synthesized proteoglycans, and Link N led to partial restoration of disc height when injected into rabbit discs in a stab model of disc degeneration (31). The model used in the present study mimics early stage degeneration in a young adult, where the tissue has sufficient numbers of cells that can respond to Link N stimulation. In contrast, diminishing cell numbers, cell senescence and possibly an inflammatory environment on the other hand often characterize human disc degeneration. Previous work from our group has shown that Link N is equally potent in an inflammatory environment (34) At this stage it might be necessary to also supply additional cells capable of synthesizing disc ECM.

There is no benign site where autologous IVD cells can be harvested and used as a cell source for IVD repair, leaving MSCs as an attractive option. The potential use of MSCs for IVD repair has been described in small animals (36-38). Favorable results in rabbits demonstrate increased disc height, as well as ECM deposition and hydration. However, other studies in the rabbit report osteophyte formation, especially when MSCs were administered without a scaffold or without sealing of the AF (39). As Link N is known to promote chondrogenesis and reduce osteogenesis of human MSCs in vitro, it may be an ideal candidate for a combination therapy (20). In addition to animal studies, a small-scale human clinical trial has reported improved pain and disability score (40). No increase in disc height was found in the clinical trials, but an increase in hydration measured by MRI could be detected. The present results indicate that MSC supplementation could be a viable option in early degeneration. However, as endplate calcification is associated with degeneration (41), it remains to be seen whether the resulting compromised nutritional pathway in degenerate discs would support the metabolic activity of additional cells (42,43).

The current model does not result in the generation of fissures only molecular depletion, whereas natural disc degeneration often involves the creation of fissures. To repair such lesions, it may require injecting Link N and stem cells in a polymerizable scaffold that will fill the lesions and allow uniform distribution of the therapeutic agents.

TABLE 2

Randomization of discs

| Animal | Degeneration control | Non-degeneration control | Link N | MSCs | Link N + MSCs |
|---|---|---|---|---|---|
| 1 | X | x | x | x | |
| 2 | | x | x | x | x |
| 3 | X | | x | x | x |
| 4 | X | x | | x | x |
| 5 | X | x | x | | x |
| 6 | X | x | x | x | |
| 7 | | x | x | x | x |
| 8 | X | | x | x | x |
| 9 | X | x | | | x |

Example 5

Figure 18:
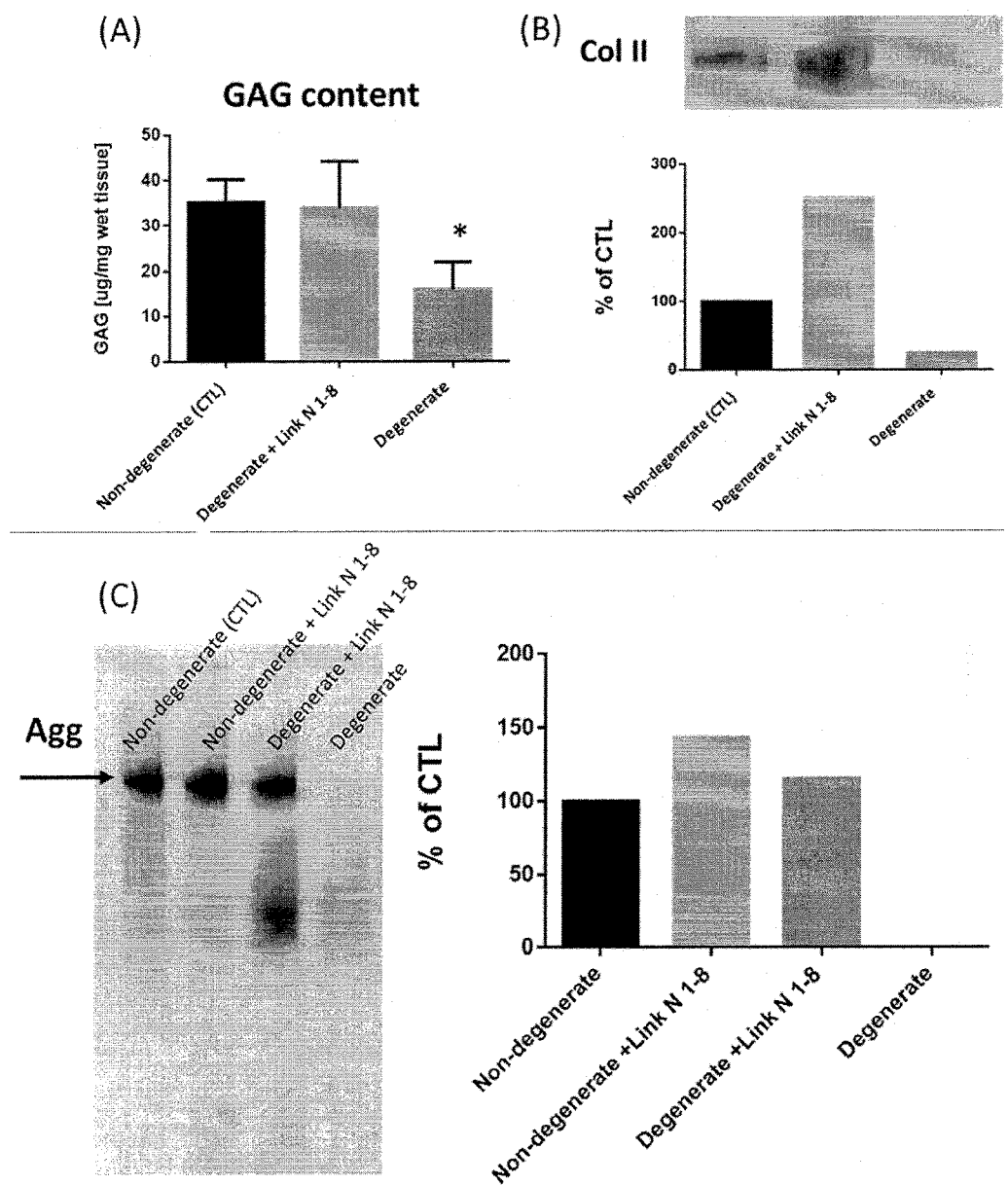
FIG. 18: Effect of Link N 1-8 on proteoglycan synthesis, aggrecan and type II collagen expression in bovine disc organ culture at 2 weeks after trypsin-induced degeneration. (A) Proteoglycan concentration in the discs were determined at 2 weeks after treatment in discs with induced degeneration, discs with induced degeneration and treated with Link N 1-8, and non-degenerate control discs. The results are represented as mean±SD of three discs from different bovine tails. (*p<0.05). (B) Immunoblotting and semi-quantitative analysis of newly synthesized type II collagen with a molecular weight of about 360 kDa at 2 weeks after treatment in discs with induced degeneration, discs with induced degeneration and treated with Link N 1-8, non-degenerate control discs and non-degenerate discs treated with Link N 1-8. The results are represented as mean±SD of seven discs from different bovine tails. (*p<0.05). (C) Immunoblotting and semi-quantitative analysis of intact aggrecan core protein with a molecular weight of about 320 kDa at 2 weeks after treatment in discs with induced degeneration, discs with induced degeneration and treated with Link N 1-8, non-degenerate control discs and non-degenerate discs treated with Link N 1-8. The results are represented as mean±SD of seven discs from different bovine tails. (*p<0.05).

Additional tests were conducted using a bovine disc organ culture. FIG. 18 demonstrates that Link N 1-8 induces statistically significant increase in on proteoglycan synthesis, aggrecan and type II collagen expression in degenerated bovine discs at 2 weeks post Link N 1-8 treatment.

It is demonstrated that Link N and the fragment comprising amino acids 1-8 can restore aggrecan levels in the degenerate disc.

Example 6

Human Link N [DHLSDNYTLDHDRAIH] (SEQ ID NO: 15) can stimulate extracellular matrix biosynthesis by intervertebral disc (IVD) cells, both in vitro and in vivo. To date, there have been no reports on the effect of bovine Link N [DHHSDNYTVDHDRVIH] (SEQ ID NO: 5) on disc cells. The purpose of this study is to compare the effect of bovine Link N (BLN) to that of human Link N (HLN) on bovine annulus fibrosus (AF) and nucleus pulposus (NP) cells.

Methods: Cells isolated from NP and AF regions of coccygeal discs from healthy 22-24 months old steers were either immediately embedded in 1.2% alginate beads for proteoglycan synthesis and gene expression or culture in monolayer for protein extraction. The beads were incubated for 18 days in media supplemented with 1 μg/ml of either HLN or BLN. The sulfated glycosaminoglycan (GAG) release was analyzed. After 7 and 14 days of culture, quantitative PCR was performed for aggrecan (AGG), ADAMTS-4 and ADAMTS-5. Smad activation was analyzed by immunoblotting using specific antibodies directed against P-Smad1/5 and P-Smad2.

Results: In both NP and AF cells, incubation with BLN and HLN resulted in increased GAG release into the culture media. GAG release was significantly higher in AF cells incubated with either BLN or HLN compared to control media. However, NP cells had a significant and consistent increase in GAG release when incubated with HLN. In AF cells, both Link-N supplementations induced a fast activation (<10 minutes) of Smad1/5 that decreased below control levels over the course of 6 hours. In NP cells, Smad1/5 appeared delayed, beginning after 30 minutes and continued to increase with time.

BLN is capable of stimulating GAG release in bovine IVD cells through the activation of Smad1/5. The fast activation of Smad1/5 by BLN in AF cells may explain our findings that AF cells respond better than NP cells to BLN supplementation in promoting GAG synthesis; Both peptides have features needed for any agent designed to stimulate disc repair.

Further details are found in Example 7.

Example 7

Intervertebral discs (IVDs) are composite structures comprised of the peripheral collagen-rich annulus fibrosus (AF) surrounding the proteoglycan-rich central nucleus pulposus (NP) [77]. They resist compression as they have a high content of the proteoglycan aggrecan, which interacts with hyaluronate to produce large proteoglycan aggregates. These interactions are stabilized by the further interaction of a link protein (FIG. 19) [78,79]. The disc cells residing in the AF and NP regulate homeostasis of IVDs through metabolic processes, maintaining a balance between anabolic and catabolic factors and controlling the expression of matrix molecules and degradative enzymes. An imbalance of this steady state metabolism leads to biochemical alterations in the composition and structure of IVD matrix due to both depleted synthesis and increased degradation, with aggrecan being particularly susceptible to proteolytic damage and loss. The progressive breakdown of the extracellular matrix (ECM) is closely associated with disc degeneration [80].

IVD degeneration plays a major role in the etiology of low back pain, which can significantly affect more than half of the population [53, 81-82]. Thus, for low back pain therapy, reversing the degeneration process and repairing (restoring the structure or function of) the degenerated IVDs is crucial. Lately, cell or growth factor therapies have been proposed to induce IVD repair [83-86]. Several studies have suggested using growth factors to stimulate cellular metabolism and change tissue homeostasis to anabolic status (matrix synthesis), thereby reversing the degeneration process.

Figure 19:
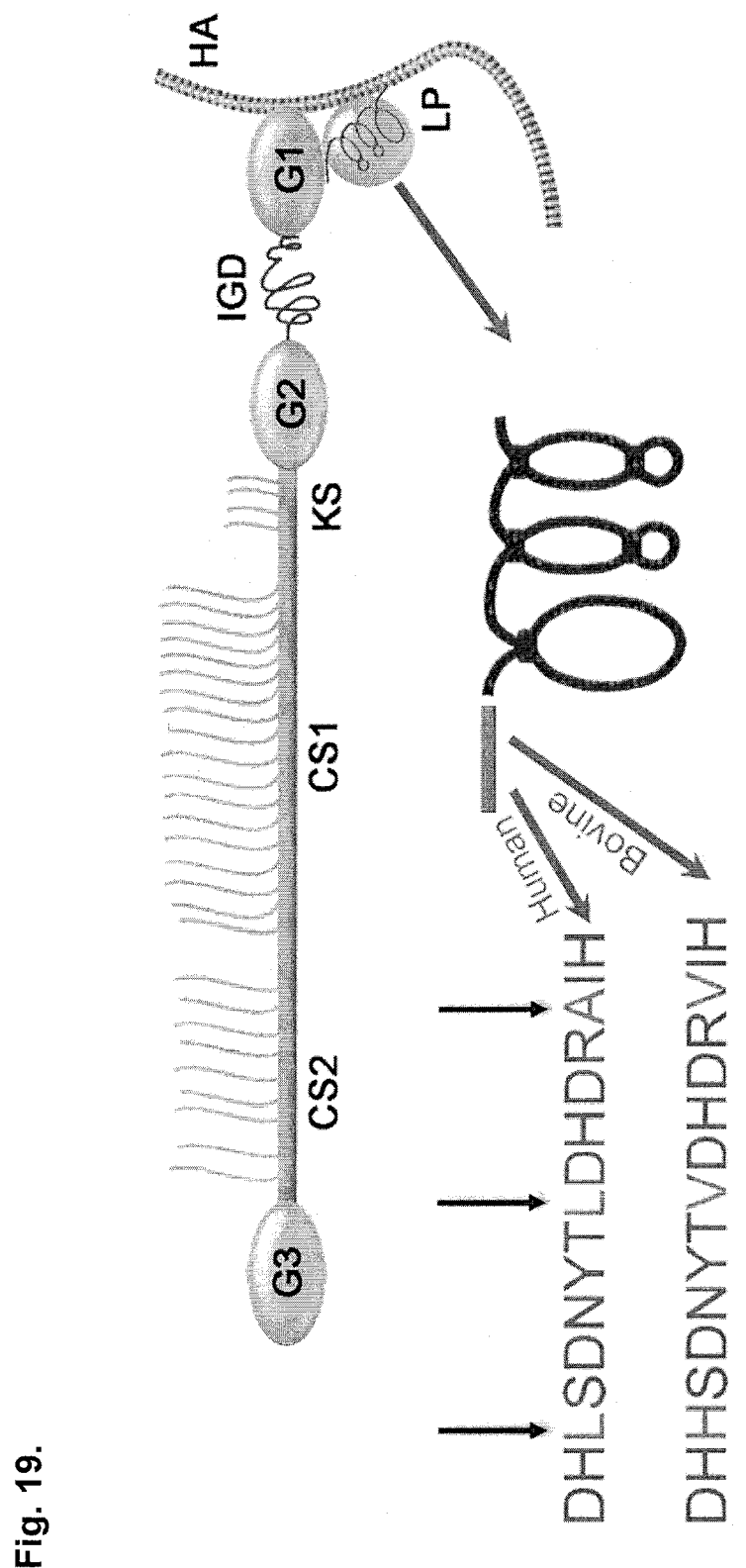
FIG. 19: Schematic illustration of link protein stabilizing the interaction between aggrecan G1 domain and hyaluronate. Link protein (LP) is stabilizing the interaction between aggrecan G1 domain and hyaluronate (HA). The figure also depicts human Link N [DHLSDNYTLDLDRAIH (SEQ ID NO: 32)] and bovine Link N [DHHSDNYTVDHDRVIH (SEQ ID NO: 5)], the N-terminal parts of link protein, and highlights the substitution of residues (marked in bold), as occurs in the bovine sequence.

Disc repair may be enhanced by growth factor supplementation such as bone morphogenetic proteins (BMPs) and transforming growth factor-β(TGF β). These growth factors can be applied directly to maximize extracellular matrix production and to promote tissue regeneration. As an economical alternative to growth factors, it may be possible to use Link N for tissue regeneration. Human Link N peptide [DHLSDNYTLDHDRAIH] (SEQ ID NO: 15) is the N-terminal peptide of link protein, a glycoprotein that stabilizes the non-covalent interaction between the aggrecan G1 domain and hyaluronate (FIG. 19). Human Link N can stimulate collagen and proteoglycan synthesis in human articular cartilage and bovine IVD cells in vitro [87-88, 35], and can increase disc height in a rabbit model of disc degeneration in vivo [31]. Previous studies have shown that Link N can also decrease the expression of type X collagen, a marker of chondrocyte hypertrophy [89], and stimulate the expression of type II collagen, a marker of cartilage and disc ECM formation [90]. Therefore, Link N has the potential to be used together with stem cells to promote the formation of the ECM necessary for IVD repair.

To date, there have been no reports on the effect of bovine Link N [DHHSDNYTVDHDRVIH] (SEQ ID NO: 5) on disc cells. The purpose of this study is to compare the effects of bovine Link N (BLN) and human Link N (HLN) on bovine IVD cells in order to determine whether substitution of residues (marked in bold), as occurs in the BLN sequence, alter Link N function.

Materials and Methods
Bovine Disc Cell Isolation

Coccygeal IVDs from healthy 20-24 month old steers were obtained from a local abattoir at 2-3 hours after slaughter. The IVDs were separated from their adjacent vertebral bodies, and the cells were isolated from the NP and AF regions by sequential digestion with 0.2% Pronase followed by 0.125% Collagenase digestion as previously described [88]. After isolation, the NP and AF cells were either immediately embedded in alginate beads or were plated in 6 well plates for protein extraction.

Alginate Embedding

After isolation the NP and AF cells were resuspended in 1.2% alginate (dissolved in 0.15 M NaCl) at a concentration of 2 million cells per ml. Alginate was chosen to assess the effect on matrix production in the absence of extensive cell proliferation [91-92]. Droplets of cell suspension were released through an 18-gauge needle into 102 mM calcium chloride solution and were let to polymerize for 10 minutes. Alginate beads were subsequently stabilized for 7 days in culture media (Dulbecco's Modified Eagle Medium high glucose supplemented with 10% fetal bovine serum and antibiotics).

Culture and Treatment of Alginate Beads

After stabilization, the alginate beads were placed in 24 well plates at a density of 9 beads/well and were incubated for 18 days in media supplemented with 1 μg/ml of either HLN or BLN (CanPeptide, Montreal). Beads cultured in media alone for the same period of time were used as the control (CTL). The concentration of BLN and HLN supplementation was chosen based on the finding that 1 μg/ml Link N induces the maximal response at stimulating proteoglycan synthesis in disc cells [93]. Culture medium was changed every third day for 18 days in order to allow sufficient time for any phenotypic changes to occur under the different Link N supplementation.

Culture and Treatment of Disc Cells

AF and NP cells were expanded in culture medium (Dulbecco's Modified Eagle Medium high glucose supplemented with 10% fetal bovine serum and antibiotics) into 6 well plates ($7.5 \times 10^5$ cells/well) until reaching 80-90% confluence. The cells were pre-incubated overnight in serum-free medium, then were incubated in 1 μg/ml HLN or BLN for different time points up to 6 hours. Cells incubated in medium alone were use as the control (CTL).

Cell Viability

Cell viability was assessed at day 18 on the alginate beads using a live/dead fluorescence assay (Live/Dead®, Invitrogen) and visualized by fluorescent microscopy.

Proteoglycan Content

The culture media of the alginate beads, with or without Link N, was changed every third day, and the sulfated glycosaminoglycan (GAG, predominantly aggrecan) released into the media was analyzed using the 1,9-dimethylmethylene blue (DMMB) dye-binding assay [94]. GAG retention in the alginate was not measured since alginate is a polyanion that reacts with DMMB and therefore interferes with the assay.

Total RNA Isolation and Gene Expression

At day 7 and day 14 the alginate beads were resuspended in citrate buffer and the cells were recovered for gene expression. Total RNA was extracted from disc cells using Trizol (Invitrogen, Burlington, ON, Canada), following the manufacturer's instructions. One microgram total RNA was reverse transcribed into cDNA using the Superscript™ First Strand cDNA synthesis kit (Invitrogen, Carlsbad, Calif., USA). Following reverse transcription, real time PCR was applied to quantitatively analyze message levels of aggrecan (AGG), ADAMTS-4 and ADAMTS-5. One microliter of cDNA was amplified using gene-specific primers (Table 3). Initially, the expression of the target gene was normalized to 18S rRNA expression levels, and then the expression of the Link N-incubated beads was normalized to the control beads.

Protein Expression

The incubated AF and NP cells were then lysed in a buffer (pH 7.4) containing 10 mM HEPES, 50 mM $Na_4P_2O_7$, 50 mM NaF, 50 mM NaCl, 5 mM EDTA, 5 mM EGTA, 2 mM $Na_3VO_4$, 1% Triton X-100 (all from Sigma-Aldrich), and a protease and phosphatase inhibitor cocktail (Roche Diagnostics, Laval, QC, Canada). Proteins were separated on 10% acrylamide gels and transferred to PVDF membranes for western blot to measure protein expression using specific antibodies directed against P-Smad1/5, P-Smad2, Smad1 and Smad2 (Cell Signaling Technology, Danvers, Mass.). The membranes were incubated in ESL Chemiluminescent reagent (GE Healthcare, Piscataway, N.J.) and scanned using the Molecular Imager VersaDoc™ MP 4000 System (Bio-Rad Canada, Mississauga, ON, Canada). The band intensities were quantified by densitometry using the ImageJ software program. The phosphorylation of Smad1/5 and Smad2 were normalized to the corresponding Smad1 and Smad2 total forms.

Statistical Analysis

All experiments were performed in triplicate and were repeated with three independent cultures. The effect of treatment and culture period as well as the significance of differences among the experimental groups (CTL, BLN and HLN) at each time point were assessed by repeated measures ANOVA followed by Tukey's Multiple Comparison Test. P value less than 0.05 was considered statistically significant.

Results

Alginate Bead Viability

Figure 20:
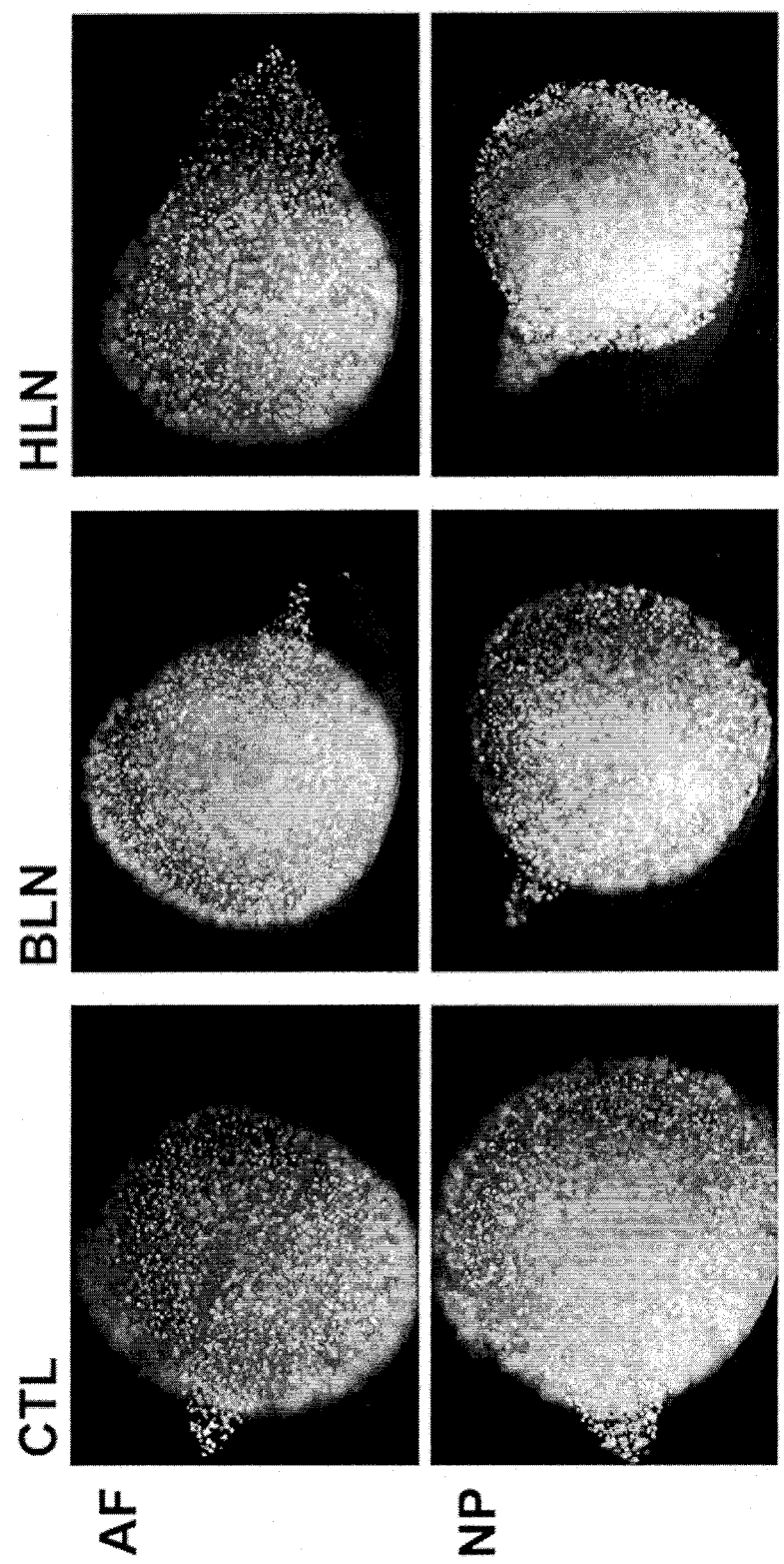
FIG. 20: Cell viability of bovine intervertebral disc cells cultured in alginate supplemented with either human or bovine Link N. Cell viability was measured using the LIVE/DEAD® Viability/Cytotoxicity Assay. Bovine intervertebral disc (IVD) cells embedded in alginate were incubated for 18 days in media supplemented with either 1 ug/ml bovine (BLN) or human (HLN) Link N. Beads cultured in media alone for the same period of time were used as the control (CTL). After 18 days, the beads were harvested and cell viability assessed. Cell viability for all beads was assessed at >98% (white bright dots).

The cell-seeded alginate scaffolds were maintained in culture for a period of 18 days in order to verify that supplementation of 1 μg/ml HLN or BLN was not detrimental to the viability of AF and NP cells. For scaffolds supplemented with either HLN or BLN, cellular viability was maintained at >98% (FIG. 20).

Effect of Bovine and Human Link N on Proteoglycan Synthesis

Figure 21:
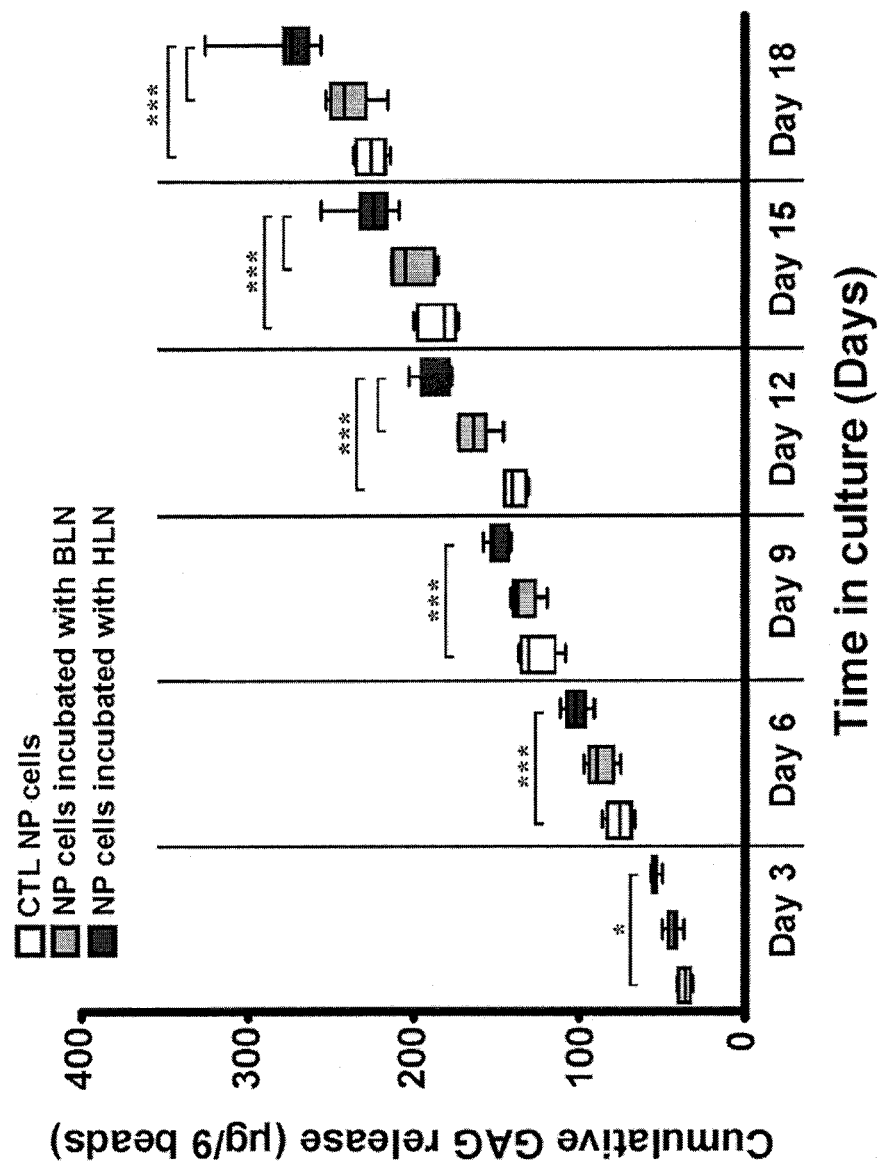
FIG. 21: Cumulative glycosaminoglycan release into the culture media by nucleus pulposus bovine cells beaded in 1.2% alginate. Nucleus pulposus (NP) bovine cells beaded in 1.2% alginate were cultured in medium supplemented with either bovine (BLN) or human (HLN) Link N (1 µg/ml) or exposed to medium alone (CTL). For each condition, the media were collected at 3, 6, 9, 12, 15, and 18 days of culture. The sulfate glycosaminoglycan (GAG) release into the media was measured by 1,9-dimethylmethylene blue (DMMB) dye-binding assay. Results are presented as box plot in which the box represents the middle 50% (25%-75% percentile) of the combined data of three independent experiments performed in triplicates ($*p<0.05$ or $***p<0.0001$).
Figure 22:
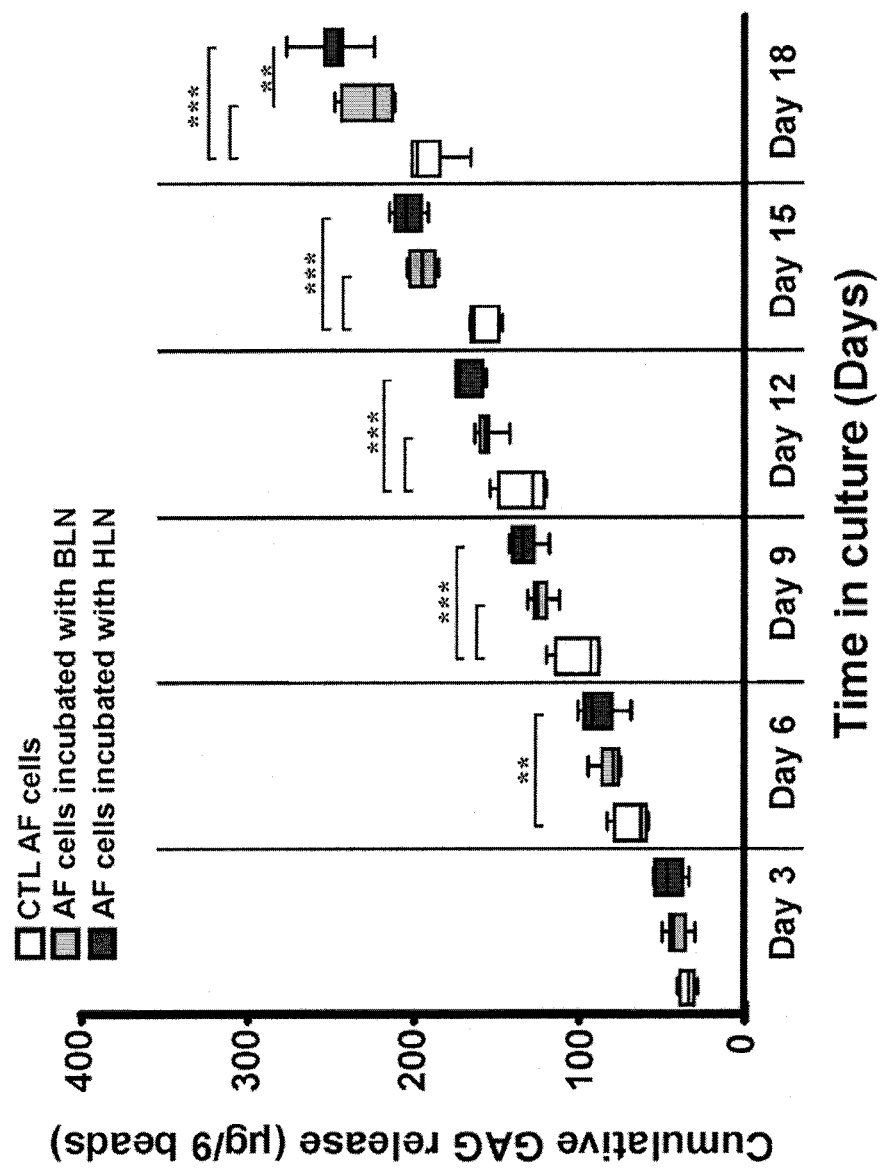
FIG. 22: Cumulative glycosaminoglycan release into the culture media by annulus fibrosus bovine cells beaded in 1.2% alginate. Annulus fibrosus (AF) bovine cells beaded in 1.2% alginate were cultured in medium supplemented with either bovine (BLN) or human (HLN) Link N (1 µg/ml) or exposed to medium alone (CTL). For each condition, the media were collected at 3, 6, 9, 12, 15, and 18 days of culture. The sulfate glycosaminoglycan (GAG) release into the media was measured by 1,9-dimethylmethylene blue (DMMB) dye-binding assay. Results are presented as box plot in which the box represents the middle 50% (25%-75% percentile) of the combined data of three independent experiments performed in triplicates ($p<0.005$ or $*p<0.0001$).

For both NP and AF cells incubated with or without Link N, the rate of GAG release into the culture medium increased with time (FIGS. 21 and 22). NP cells tended to exhibit a similar total GAG release to that of AF cells.

The GAG release by NP cells supplemented with 1 μg/ml HLN was significantly higher than the control at all-time points (p<0.05 for day 3 and p<0.0001 for days 6, 9, 12, 15, 18). When compared with the GAG release by NP cells supplemented with BLN, this difference was only significant (p<0.05) starting at day 12. In contrast, no statistical significance was observed between the GAG release by NP cells supplemented with BLN compared with the control, although a tendency towards an increase was observed (FIG. 21).

For AF cells supplemented with 1 μg/ml HLN the GAG release was significantly higher than the control starting from day 6 (p<0.005 for day 6 and p<0.0001 for days 9, 12, 15, 18) while for those supplemented with 1 μg/ml BLN, the GAG release was significantly higher than the control starting from day 9 (p<0.001) (FIG. 22). Finally, although GAG release tended to be higher in AF cells supplemented with HLN than that of BLN at all-time points, it was only at day 18 that this difference was significant.

Similarly to the results of our previous experiments [95], most of the GAG synthesis was found released in the culture medium with minimal retention in the alginate beads. GAG release is therefore a measure of proteoglycan synthesis, and it appears that BLN is also capable of stimulating GAG release.

The Effect of Bovine or Human Link N on Matrix Metabolism

Figure 23:
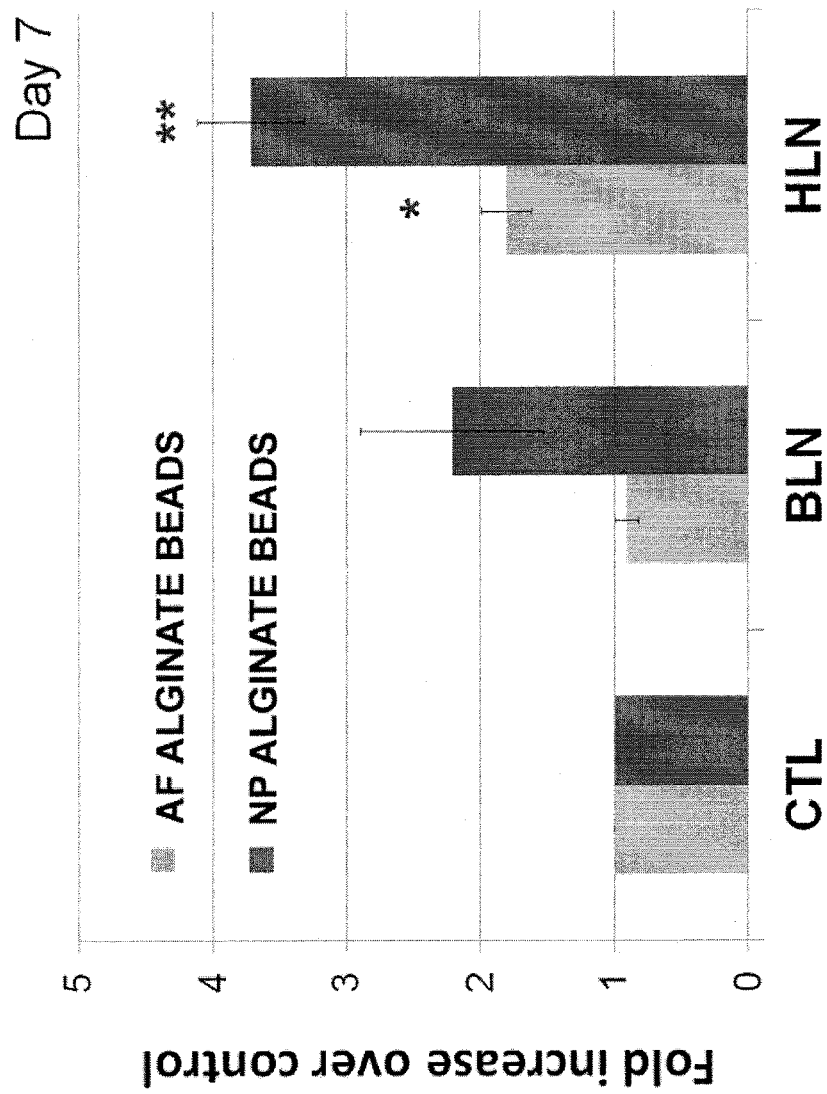
FIG. 23: Changes in aggrecan gene expression. Changes in aggrecan (AGG) gene expression of the annulus fibrosus (AF) and nucleus pulposus (NP) bovine cells beaded in 1.2% alginate at 1 week after incubation in medium supplemented with either 1 µg/ml bovine (BLN) or human Link N (HLN). Gene expression was measured by RT-PCR. 18S rRNA was used as a housekeeping gene and served to normalize the results. The values are expressed as a ratio of the gene expression of cells exposed to Link N relative to that of cells exposed to medium alone (CTL). ($*p<0.05$, $**p<0.001$).

To investigate the effect of BLN or HLN on proteoglycan and proteinase expression, bovine cell-seeded alginate scaffolds were exposed to 1 μg/mL Link N and relative gene expression was evaluated for AGG, ADAMTS-4 and ADAMTS-5. Results are expressed relative to cells unexposed to Link N (CTL). Both Link N treatments led to an increase in AGG gene expression in NP cells, when compared to the control, however, with HLN incubation, this increase was larger and statistically significant (p=0.0107) (FIG. 23). In AF cells, the AGG expression was upregulated in response to HLN incubation compared to controls (p=0.0257), but no significant effect was observed between BLN compared to controls (p>0.1).

Although at day 7, no important change in ADAMTS-4 expression of NP cells was observed, at day 14, the expression indicated a non-significant decreasing tendency (FIG. 24B). In contrast, for the AF cells, an increase in mRNA ADAMTS-4 expression was observed with both BLN and HLN incubations, although the differences were not significant compared to the controls (FIG. 24A).

At day 7, in response to HLN incubation, ADAMTS-5 expression was upregulated for both AF and NP cells. However, this increase was only significant for AF cells (p=0.0149). In response to BLN incubation, ADAMTS-5 expression was down-regulated in AF cells (p=0.0329) and upregulated in NP cells when compared to controls (p=0.0058) (FIGS. 24C and 24D).

Canonical Smad-Mediated Signaling as a Regulator of Human and Bovine Link N Function in Bovine Disc Cells To explain the molecular mechanisms by which BLN and HLN induce anabolic responses in bovine NP and AF cells, we investigated whether BLN and HLN activate Smad1/5 proteins as principal transducers of the Smad canonical signaling pathways.

Figure 25:
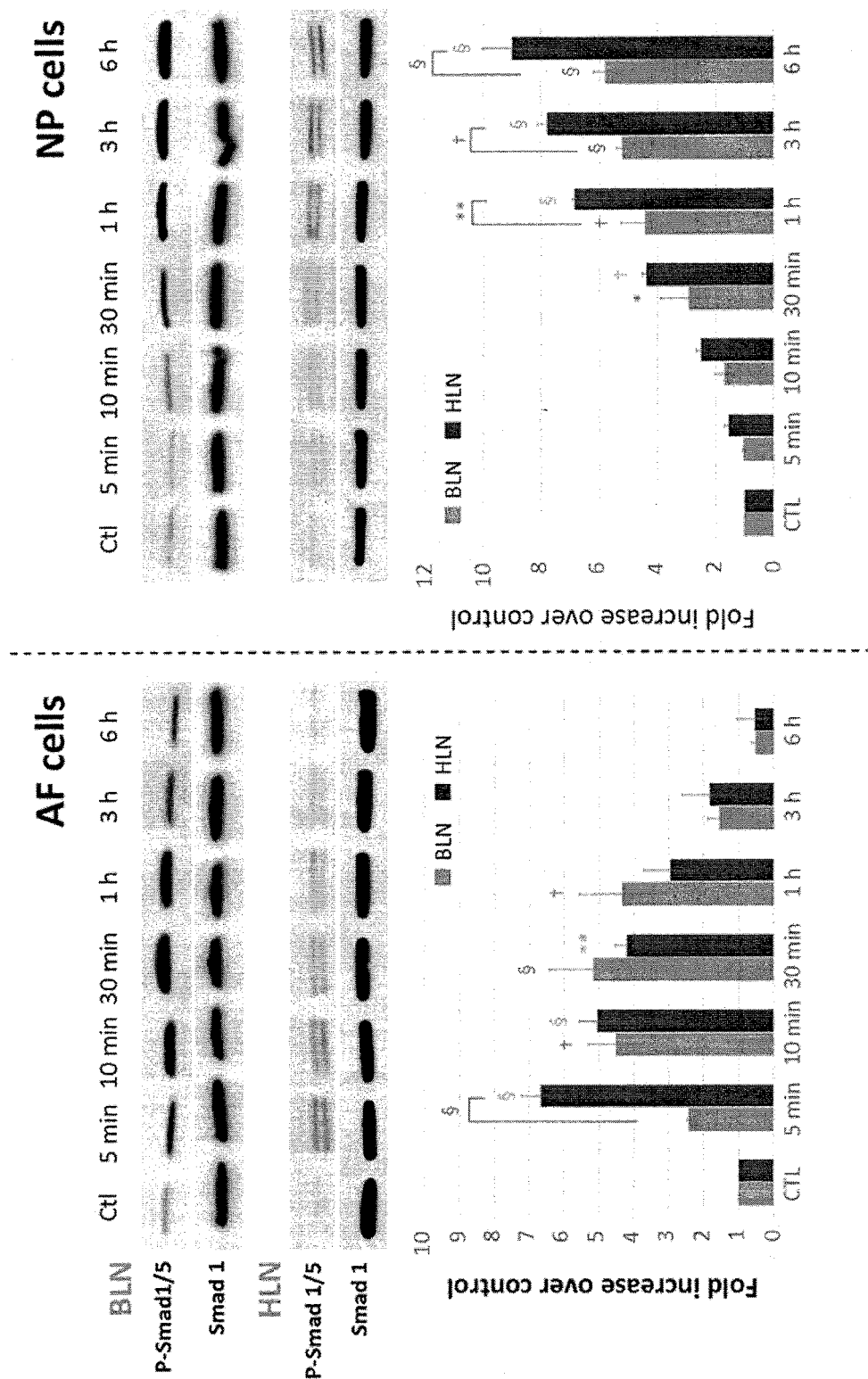
FIG. 25: The effect of bovine or human Link N on Smad1/5 activation in annulus fibrosus and nucleus pulposus bovine cells. Annulus fibrosus (AF) and nucleus pulposus (NP) bovine cells were cultured for 6 h in medium supplemented with either 1 µg/ml of bovine (BLN) or human Link N (HLN). Protein expression was analysed by immunoblotting using specific antibodies against total Smad1 and phospho-Smad1/5. Quantitative results depicting the combined data for three independent experiments performed in triplicates are presented as mean±standard deviation ($*p<0.05$; $**p<0.01$; $^\dagger p<0.001$; $^\S p<0.0001$). Bands on gels are shown for one representative experiment.

Western blot results revealed that HLN activates the Smad1/5 in bovine AF cells within 5 minutes, while the activation with BLN occurred within 10 minutes, achieving maximum activation at 30 minutes (FIG. 25). For both Link N supplementations, Smad1/5 levels in AF cells decreased to below the control levels after 6 hours. In NP cells, BLN and HLN supplementation significantly stimulated Smad1/5 after 30 minutes and continued to increase with time. However, for both IVD cells, HLN appeared to be more effective at Smad1/5 activation than BLN.

Figure 26:
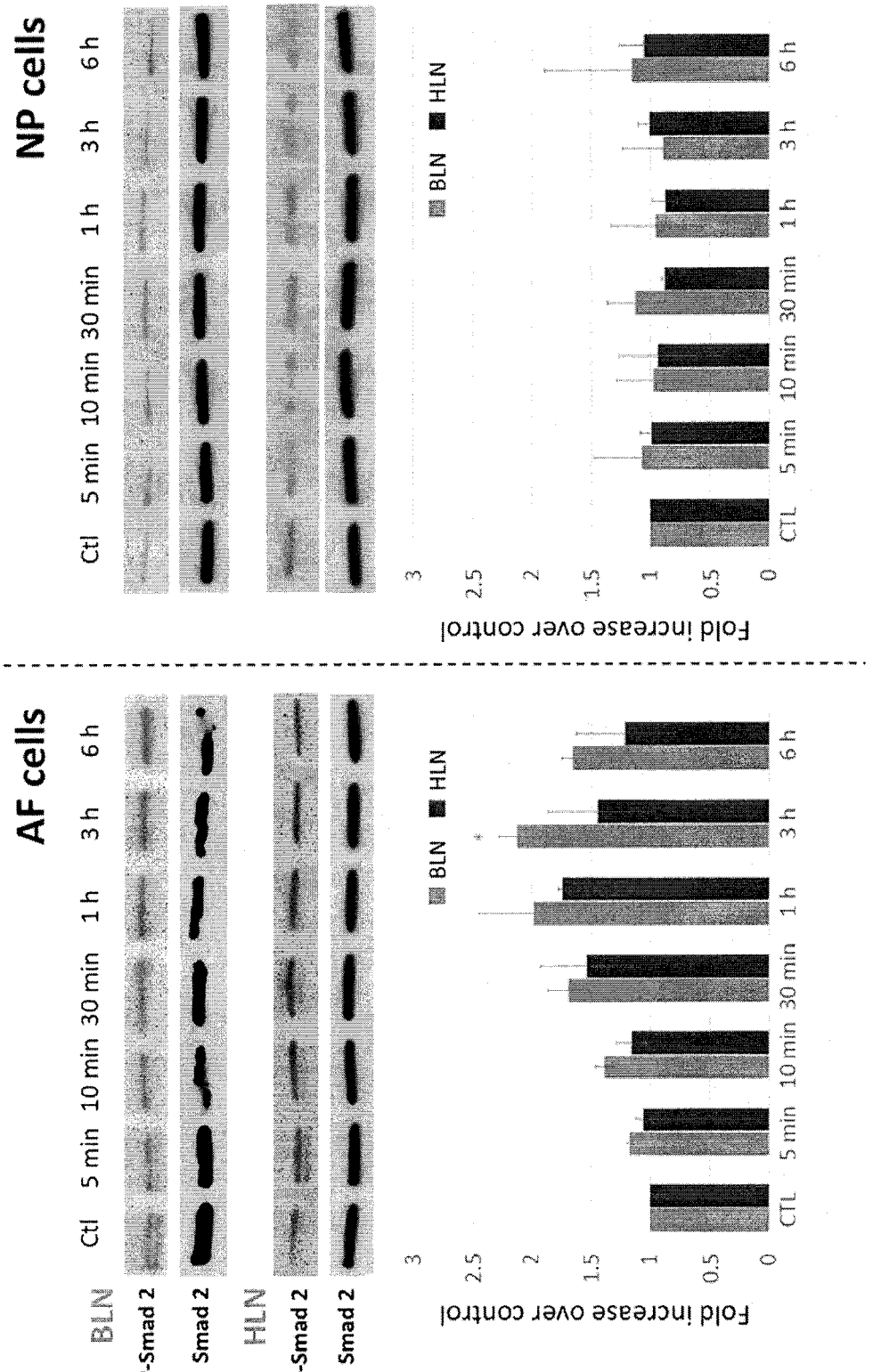
FIG. 26: The effect of bovine or human Link N on Smad2 activation in annulus fibrosus and nucleus pulposus bovine cells. Annulus fibrosus (AF) and nucleus pulposus (NP) bovine cells were cultured for 6 h in medium supplemented with either 1 µg/ml of bovine (BLN) or human Link N (HLN). Protein expression was analysed by immunoblotting using specific antibodies against total and phospho-Smad2. Quantitative results depicting the combined data for three independent experiments performed in triplicates are presented as mean±standard deviation ($*p<0.05$). Bands on gels are shown for one representative experiment.

In AF cells, incubation in either HLN or BLN seemed to induce a slightly increased Smad2 activation up to three hours. In contrast, no Smad2 activation was detected in NP cells incubated in Link N (FIG. 26).

Discussion

Previous studies have shown that Link N can act as a growth factor and stimulate the synthesis of proteoglycans and collagens in vitro in bovine IVD cells [88, 35] and can increase disc height in a rabbit model of disc degeneration in vivo [31]. Link N can also stimulate proteoglycan synthesis by human disc cells in 3-D scaffolds as well as in intact human discs [93]. The present data indicates that HLN significantly stimulated proteoglycan synthesis at all-time points in NP cells and from day 6 in AF cells. NP cells supplemented with BLN showed a tendency towards an increase in proteoglycan synthesis that was not significant. Interestingly, the GAG release of AF cells supplemented with BLN was significantly higher than the control from day 9 onwards, suggesting that BLN is more effective in stimulating proteoglycan synthesis in AF cells than in NP cells. In addition, HLN is able to down-regulate ADAMTS-4 expression after 14 days in bovine NP cells but does not significantly affect ADAMTS-4 expression in AF cells. BLN had no significant effect on ADAMTS-4 expression after 14 days in NP cells, although a tendency towards an increase was observed in AF cells. BLN was able to downregulate ADAMTS-5 in the AF cells while upregulating ADAMTS-5 in NP cells after 14 days. Finally, BLN and HLN stimulate proteoglycan synthesis by NP and AF cells, through Smad1/5 signaling pathways.

Previously, we found that although cell proliferation was not expected to be extensive in alginate, [91-92] it may have contributed to changes in GAG production. In this study we analyzed the message level of aggrecan and the cumulative proteoglycan release, and found that the GAG release for both AF and NP cells incubated with Link N increased compared with the control, as did the mRNA expression of aggrecan. The similarity in GAG synthesis by NP and AF cells that we found and the increased presence and survival of AF cells during proteolytic isolation may mean that AF cells could serve as a functional substitute for NP cells, which would be beneficial for tissue engineering.

The fact that BLN stimulated ADAMTS-5 in the NP while downregulating it in the AF may be explained by the facts that repair involves remodeling of the disc ECM, and that remodeling involves proteolysis. Hence, there is no need for a complete absence of proteolysis during repair, as long as the matrix synthesis exceeds turnover. HLN and BLN can stimulate proteoglycan production to help restore disc function. The fact that HLN activated Smad1/5 in bovine AF cells immediately, within 5 minutes, while the activation with BLN occurred gradually within 30 minutes, suggests that HLN activation may be direct while that of BLN may be indirect. The indirect activation may also be the case with NP cells, where supplementation with BLN and HLN significantly stimulated Smad1/5 after 30 minutes and continued to increase for the duration of the testing period (6 hours). Thus, BLN in the AF and NP as well as HLN in the NP may activate other molecules that in turn stimulate proteoglycan synthesis.

The fast activation within 10 minutes of Smad1/5 by BLN in AF cells may explain our finding that AF cells respond better than NP cells to BLN supplementation in promoting proteoglycan synthesis. Previous, studies have shown that AF cells from bovine discs produced more proteoglycan than NP cells when stimulated with TGF-β [96]. However, this is not always the case, as NP and AF cells were capable of responding in a similar manner [97]. The ability of Link N to directly stimulate Smad1/5 may vary due to differences in age. In young discs the NP is the main source of proteoglycan. However, increased proteoglycan content in the AF is observed with age and degeneration [96, 98], probably through direct activation of Smad1/5 signaling.

Although, both peptides have features needed for any agent designed to stimulate disc repair, HLN supplementation could be a better option for treating disc degeneration during its early stages, while the AF is still intact. This axiom posits an intact AF for optimal repair in order to prevent the protrusion of the NP due to the increased swelling potentially associated with proteoglycan accumulation.

BLN can stimulate proteoglycan production in vitro in both the NP and AF cells by indirect activation of Smad1/5 signaling. Therefore in principle, BLN supplementation could also be an option for treating disc degeneration. HLN at the concentration of 1 ug/ml is effective at stimulating proteoglycan synthesis and can directly activate Smad1/5 signaling in the AF, which is the main source of proteoglycan synthesis with age and degeneration.

LIST OF ABBREVIATIONS 18S rRNA: 18S ribosomal RNA; ADAMTS: a disintegrin and metalloprotease with thrombospondin-like repeats; AGG: aggrecan; AF: annulus fibrosus; BLN: bovine Link N; BMPs: bone morphogenetic proteins; DMMB: 1,9-dimethylmethylene blue; ECM: extracellular matrix; GAG: sulfated glycosaminoglycan; HA: hyaluronate; HLN: human Link N; IVD: intervertebral disc; LP: link protein; NP: nucleus pulposus; PCR: polymerase chain reaction; RT: reverse transcription; TGF β: transforming growth factor-β.

TABLE 3

Oligonucleotide primers used to assess gene expression

| Gene | Sequence | Size |
|---|---|---|
| AGG | Forward (6499-6518):(SEQ ID NO: 22)<br>AATGCCCAGGACTACCAGTG<br>Reverse (6636-6665):(SEQ ID NO: 23)<br>CCCTTCTCATGCCAGATCAT | 167 bp |
| ADAMTS-4 | Forward (1528-1547):(SEQ ID NO: 24)<br>CAATGCACTGGTCTGAATGG<br>Reverse (1659-1678):(SEQ ID NO: 25)<br>CTAGGAGACAGTGCCCGAAG | 151 bp |
| ADAMTS-5 | Forward (1165-1184):(SEQ ID NO: 26)<br>GGGACCATATGCTCTCCTGA<br>Reverse (1331-1350):(SEQ ID NO: 27)<br>AATGCTGGTGAGGATGGAAG | 186 bp |
| 18S rRNA | Forward (1351-1370):(SEQ ID NO: 28)<br>GGAGCGATTTGTCTGGGTTA<br>Reverse (1532-1551):(SEQ ID NO: 29)<br>CGCTGAGCCAGTCAGTGTAG | 201 bp |

Example 8

Figure 27:
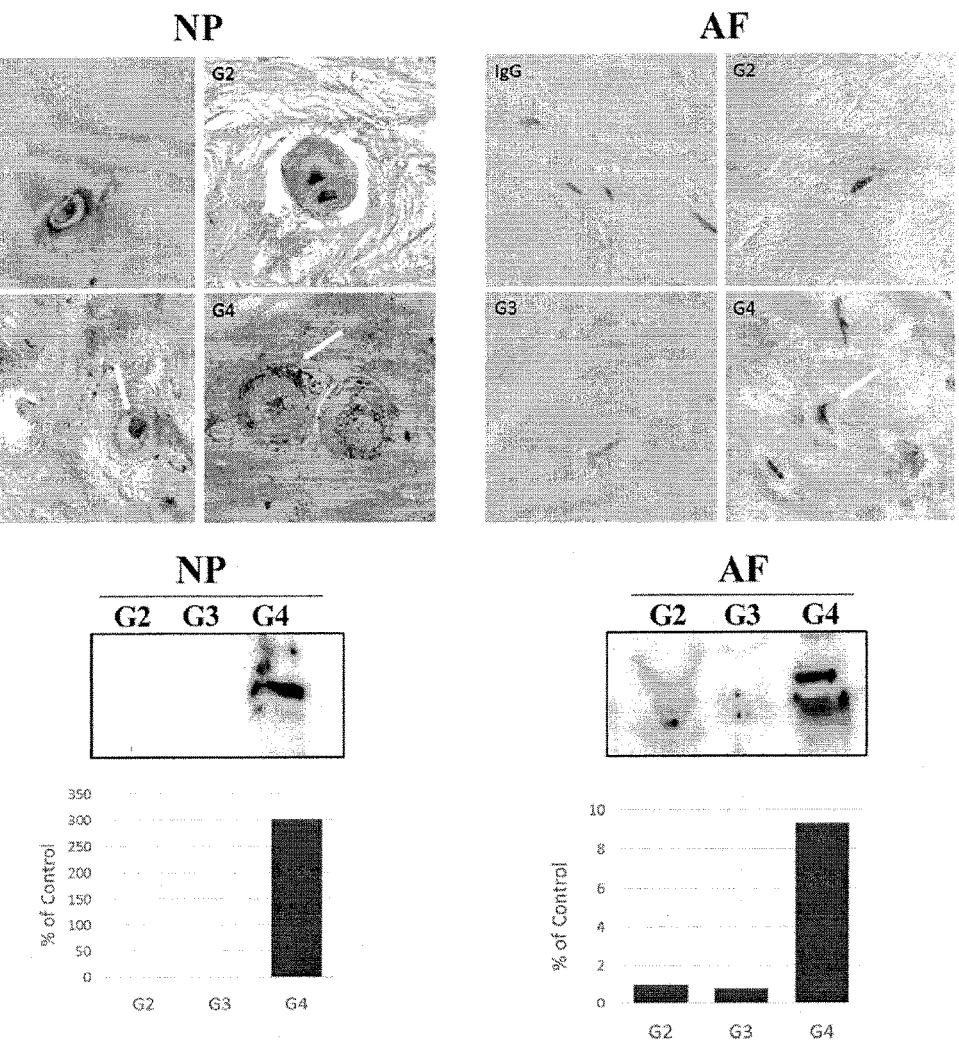
FIG. 27: NGF expression in human discs from grades 2 to 4 (AF and NP regions) with degeneration. The figure is a series of tissue stains and an immunoblot showing that NGF expression in human IVD increases with degeneration.
Figure 30:
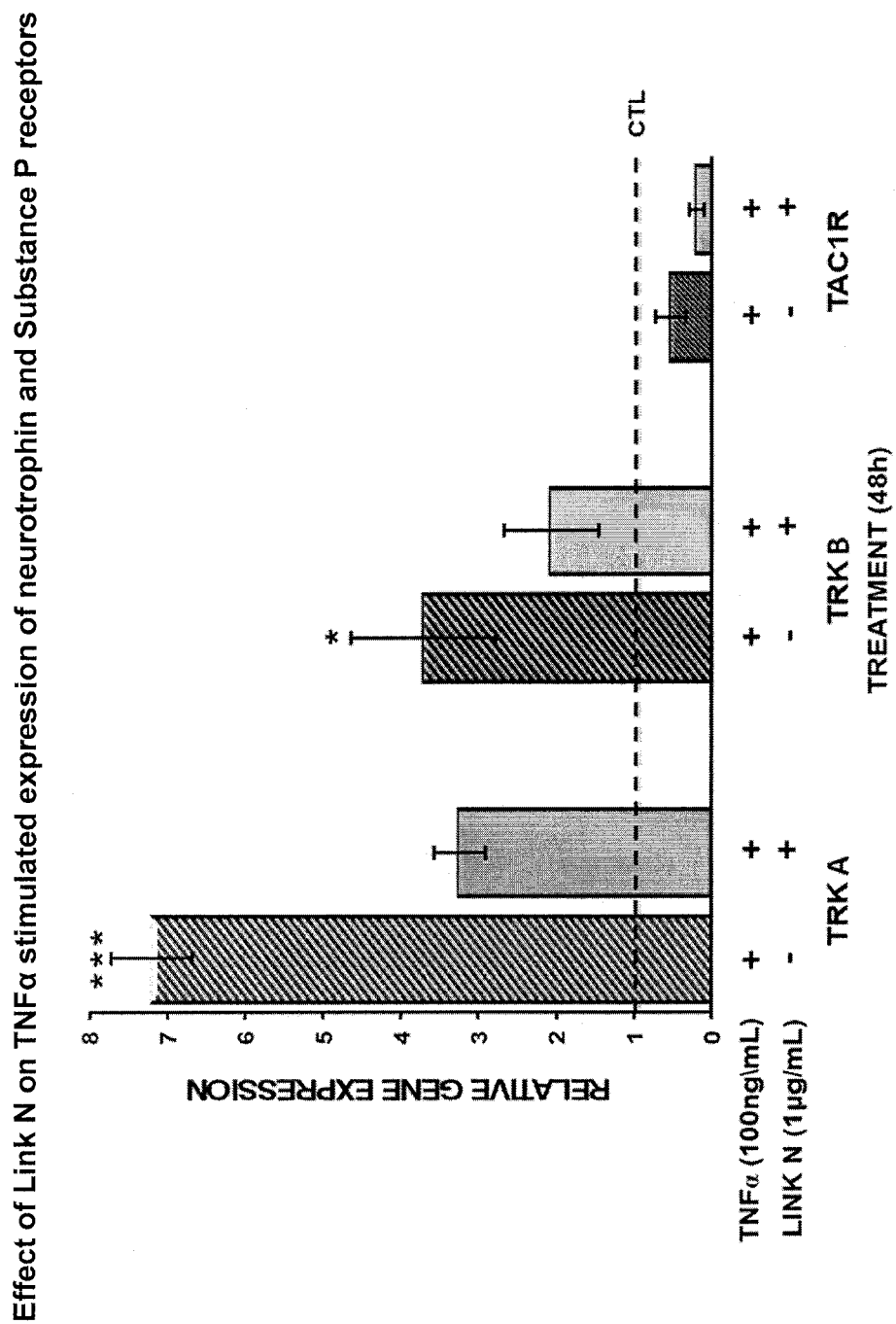
FIG. 30: Link N suppresses TNFα stimulated expression of neurotrophin (TRKA and TRKB) and Substance P (TAC1R) receptors. Changes in neutrophin and Substance P gene expression by annulus fibrosus (AF) from grade 2 human discs 24 hrs stimulated after Link N (1 µg/ml)+TNFα (100 ng/ml) or TNFα (100 ng/ml) alone supplementation. The results are shown as means±S.D. of four independent experiments with four different donors. $*p<0.05$ vs. control.
Figure 31:
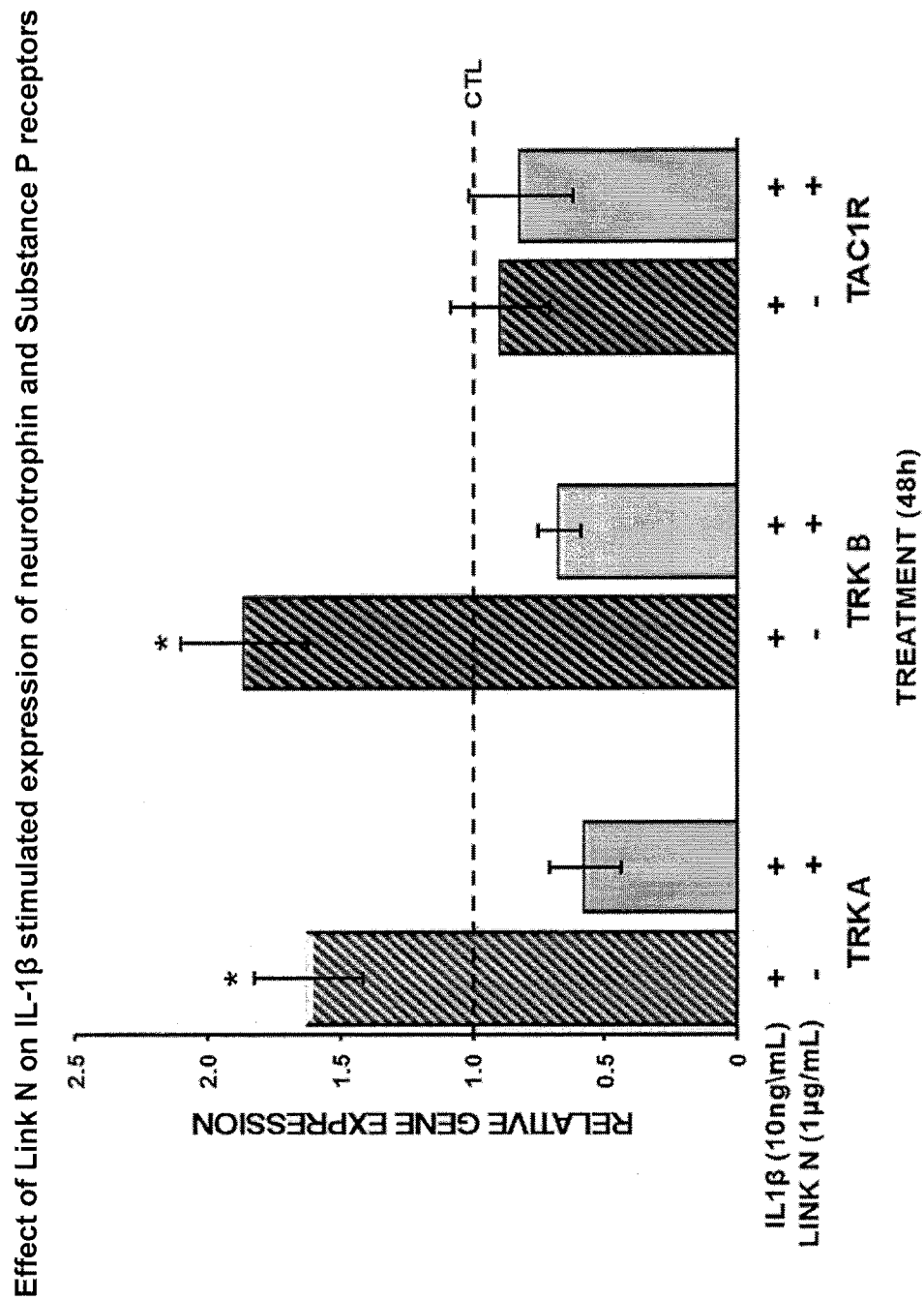
FIG. 31: Link N suppresses Il-1beta stimulated expression of neurotrophin (TRKA and TRKB) and Substance P (TAC1R) receptors. Changes in neutrophin and Substance P gene expression by annulus fibrosus (AF) from grade 2 human discs 24 hrs stimulated after Link N (1 µg/ml)+IL-1β (10 ng/ml) or IL-1β (10 ng/ml) alone supplementation. The results are shown as means±S.D. of four independent experiments with four different donors. $*p<0.05$ vs. control.

FIG. 27 is a series of cell stainings and an immunoblot showing that NGF expression in IVD increases with degeneration in both NP and AF cells. FIG. 28 demonstrates that Link N suppresses TNF alpha induced gene expression of neurotrophins (NGF, BDNF) and Substance P (TAC1) in AF cells. FIG. 29 demonstrates that Link N suppresses IL-1beta induced expression of neurotrophins (NGF, BDNF) and substance P (TAC1) in AF cells. FIGS. 30 and 31 demonstrate that the effect of Link N is mediated by reducing the level of neurotrophin and SP receptors.

Figure 32:
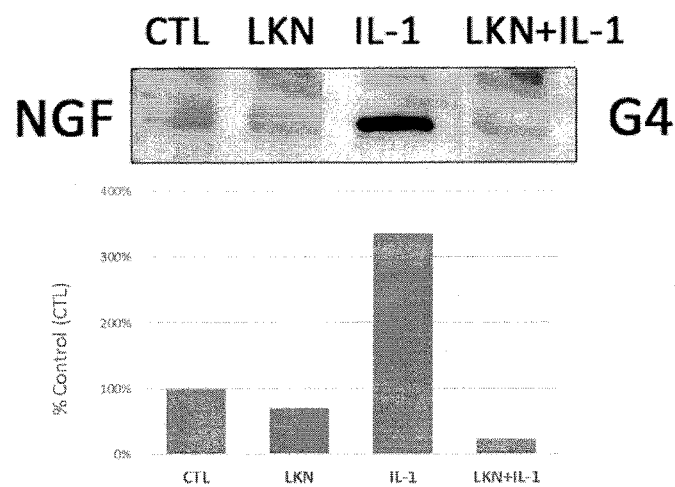
FIG. 32: Analysis of NGF gene expression and released in the media of AF cells incubated with Link N. Western blots and semi-quantitative analysis of NGF protein with a molecular weight of about 27 kDa in grade 4 AF cells treated with Link N, IL-1β, or Link N and IL-1β treated. The results are represented as mean±SD of 4 discs from different donors ($*p<0.05$).
Figure 33:
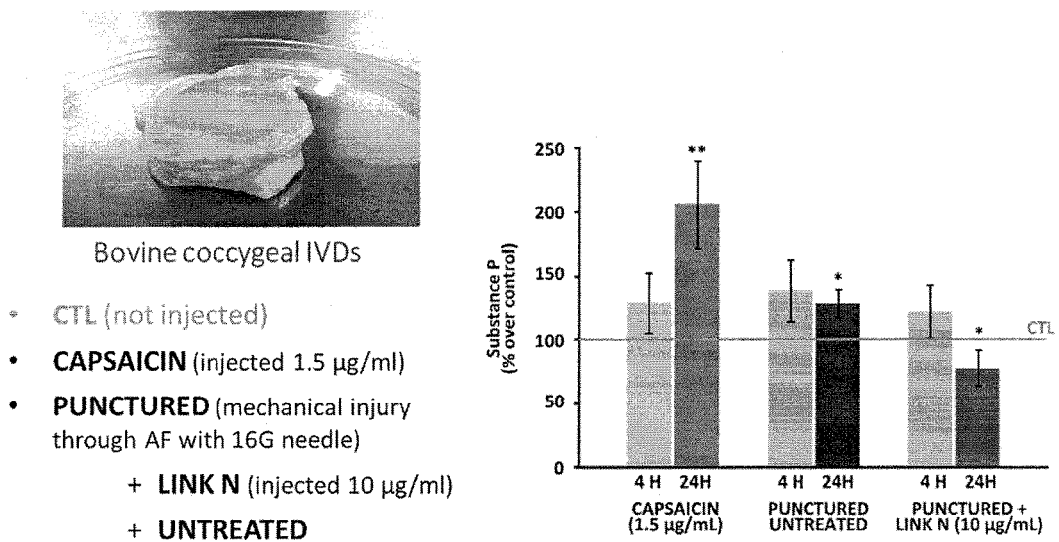
FIG. 33: is a photograph of a bovine coccygeal IVD and a graph demonstrating that Link N reduced substance P release from injured bovine IVD. Changes in substance P release by bovine discs 4 or 24 hours after being treated with capsaicin, punctured only or punctured+Link N (10 µg/ml) supplementation. The results are shown as means±S.D. of four independent experiments. *$p<0.05$ vs. control.

FIG. 32 shows that Link N is capable to inhibit suppresses IL-1 beta induced NGF release in grade 4 human AF cells. FIG. 33 demonstrates that Link N (10 µg/ml) supplementation reduces the Substance P release from injured bovine discs 24 hours after puncture.

It is demonstrated that NGF expression human IVD increases with degeneration. Link N decreases Substance P release from mechanically injured IVDs. Link N significantly suppresses TNFalpha and IL-1 beta induced neurotrophin gene expression and neurotrophin receptors in AF cells.

Example 9

Smaller fragments are tested for activity. Fragments of amino acids 1-4, 4-8 and 3-6 of SEQ ID NO: 1 are tested. Smaller and smaller fragments e.g. consisting of amino acids 1-7, 1-6, 1-5 etc are tested until activity is lost. Similarly smaller fragments missing amino acids from the NH2 end are tested, e.g. consisting of amino acids 2-8, 3-8, 4-8, 5-8 etc are tested. PCR analysis and/or 35S as described in other embodiments could be used as a readout.

Example 10

Link N fragments can include one or more amino acid changes found in one of the species in the table below.

Table of sequences for different species of Link N.

| | 1 | 2 | 3 | 4 | 5 | 6 | 7 | 8 | – | 9 | 10 | 11 | 12 | 13 | 14 | 15 | 16 | SEQ ID NO: |
|---|---|---|---|---|---|---|---|---|---|---|---|---|---|---|---|---|---|---|
| Human | D | H | L | S | D | N | Y | T | – | L | D | H | D | R | A | I | H | 4 |
| Bovine | D | H | H | S | D | N | Y | T | – | V | D | H | D | R | V | I | H | 5 |
| Horse | D | H | R | S | D | N | Y | T | – | L | D | H | D | R | V | I | H | 11 |
| Rabbit | D | H | Q | S | N | N | Y | T | – | L | G | H | D | R | V | I | H | 12 |
| Dog | D | H | H | S | D | N | Y | T | – | L | N | Y | D | R | V | I | H | 13 |
| Mouse | D | H | H | L | S | D | S | Y | – | T | P | P | D | Q | D | R | V | 14 |
| | D | H | X1 | X2 | X3 | X4 | X5 | X6 | | X7 | X8 | X9 | D | X10 | X11 | X12 | X13 | |

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

CITATIONS FOR REFERENCES REFERRED TO IN THE SPECIFICATION

1. Mwale, F. (2013) Collagen and other proteins of the nucleus pulposus, annulus fibrosus, and cartilage endplates. I. M. Shapiro, M. V. Risbud (eds.), *The Intervertebral discs* 5, 79-92
2. Ishihara, H., McNally, D. S., Urban, J. P., and Hall, A. C. (1996) Effects of hydrostatic pressure on matrix synthesis in different regions of the intervertebral disk. *J Appl Physiol* (1985) 80, 839-846
3. Handa, T., Ishihara, H., Ohshima, H., Osada, R., Tsuji, H., and Obata, K. (1997) Effects of hydrostatic pressure on matrix synthesis and matrix metalloproteinase production in the human lumbar intervertebral disc. *Spine* (Phila Pa. 1976) 22, 1085-1091
4. Hutton, W. C., Elmer, W. A., Boden, S. D., Hyon, S., Toribatake, Y., Tomita, K., and Hair, G. A. (1999) The effect of hydrostatic pressure on intervertebral disc metabolism. *Spine* (Phila Pa. 1976) 24, 1507-1515
5. Hsieh, A. H., and Lotz, J. C. (2003) Prolonged spinal loading induces matrix metalloproteinase-2 activation in intervertebral discs. *Spine* (Phila Pa. 1976) 28, 1781-1788
6. Kang, J. D., Stefanovic-Racic, M., McIntyre, L. A., Georgescu, H. I., and Evans, C. H. (1997) Toward a biochemical understanding of human intervertebral disc degeneration and herniation. Contributions of nitric oxide, interleukins, prostaglandin E2, and matrix metalloproteinases. *Spine* (Phila Pa. 1976) 22, 1065-1073
7. Goupille, P., Jayson, M. I., Valat, J. P., and Freemont, A. J. (1998) Matrix metalloproteinases: the clue to intervertebral disc degeneration? *Spine* (Phila Pa. 1976) 23, 1612-1626
8. Oegema, T. R., Jr., Johnson, S. L., Aguiar, D. J., and Ogilvie, J. W. (2000) Fibronectin and its fragments increase with degeneration in the human intervertebral disc. *Spine* 25, 2742-2747.
9. Roberts, S., Caterson, B., Menage, J., Evans, E. H., Jaffray, D. C., and Eisenstein, S. M. (2000) Matrix metalloproteinases and aggrecanase: their role in disorders of the human intervertebral disc. *Spine* (Phila Pa. 1976) 25, 3005-3013
10. Akhatib, B., Onnerfjord, P., Gawri, R., Ouellet, J., Jarzem, P., Heinegard, D., Mort, J., Roughley, P., and Haglund, L. (2013) Chondroadherin Fragmentation Mediated by the Protease HTRA1 Distinguishes Human Intervertebral Disc Degeneration from Normal Aging. *J Biol Chem* 288, 19280-19287
11. Annunen, S., Paassilta, P., Lohiniva, J., Perala, M., Pihlajamaa, T., Karppinen, J., Tervonen, O., Kroger, H., Lande, S., Vanharanta, H., Ryhanen, L., Goring, H. H., Ott, J., Prockop, D. J., and Ala-Kokko, L. (1999) An allele of COL9A2 associated with intervertebral disc disease. *Science* 285, 409-412.
12. Kawaguchi, Y., Osada, R., Kanamori, M., Ishihara, H., Ohmori, K., Matsui, H., and Kimura, T. (1999) Association between an aggrecan gene polymorphism and lumbar disc degeneration. *Spine* 24, 2456-2460.
13. Ala-Kokko, L. (2002) Genetic risk factors for lumbar disc disease. *Ann Med* 34, 42-47
14. Roughley, P., Martens, D., Rantakokko, J., Alini, M., Mwale, F., and Antoniou, J. (2006) The involvement of aggrecan polymorphism in degeneration of human intervertebral disc and articular cartilage. *Eur Cell Mater* 11, 1-7; discussion 7
15. Thompson, J. P., Pearce, R. H., Schechter, M. T., Adams, M. E., Tsang, I. K., and Bishop, P. B. (1990) Preliminary evaluation of a scheme for grading the gross morphology of the human intervertebral disc. *Spine* 15, 411-415.
16. Mwale, F., Roughley, P., and Antoniou, J. (2004) Distinction between the extracellular matrix of the nucleus pulposus and hyaline cartilage: a requisite for tissue engineering of intervertebral disc. *Eur Cell Mater* 8, 58-64
17. Wuertz, K., and Haglund, L. (2013) Inflammatory Mediators in Intervertebral Disk Degeneration and Discogenic Pain. *Global Spine J* 3, 175-184

18. Abbaszade, I., Liu, R. Q., Yang, F., Rosenfeld, S. A., Ross, O. H., Link, J. R., Ellis, D. M., Tortorella, M. D., Pratta, M. A., Hollis, J. M., Wynn, R., Duke, J. L., George, H. J., Hillman, M. C., Jr., Murphy, K., Wiswall, B. H., Copeland, R. A., Decicco, C. P., Bruckner, R., Nagase, H., Itoh, Y., Newton, R. C., Magolda, R. L., Trzaskos, J. M., and Burn, T. C. (1999) Cloning and characterization of ADAMTS11, an aggrecanase from the ADAMTS family. *J Biol. Chem.* 274, 23443-23450

19. Almaawi, A., Wang, H. T., Ciobanu, O., Rowas, S. A., Rampersad, S., Antoniou, J., and Mwale, F. (2013) Effect of acetaminophen and nonsteroidal anti-inflammatory drugs on gene expression of mesenchymal stem cells. *Tissue Eng Part A* 19, 1039-1046

20. Antoniou, J., Wang, H. T., Alaseem, A. M., Haglund, L., Roughley, P. J., and Mwale, F. (2012) The effect of Link N on differentiation of human bone marrow-derived mesenchymal stem cells. *Arthritis research & therapy* 14, R267

21. Jim, B., Steffen, T., Moir, J., Roughley, P., and Haglund, L. (2011) Development of an intact intervertebral disc organ culture system in which degeneration can be induced as a prelude to studying repair potential. *Eur Spine J* 20, 1244-1254

22. Demers, C. N., Antoniou, J., and Mwale, F. (2004) Value and limitations of using the bovine tail as a model for the human lumbar spine. *Spine (Phila Pa. 1976)* 29, 2793-2799

23. Liebscher, T., Haefeli, M., Wuertz, K., Nerlich, A. G., and Boos, N. (2011) Age-related variation in cell density of human lumbar intervertebral disc. *Spine (Phila Pa. 1976)* 36, 153-159

24. Rosenberg, L. (1971) Chemical basis for the histological use of safranin O in the study of articular cartilage. *J Bone Joint Surg Am* 53, 69-82

25. Barbosa, I., Garcia, S., Barbier-Chassefiere, V., Caruelle, J. P., Martelly, I., and Papy-Garcia, D. (2003) Improved and simple micro assay for sulfated glycosaminoglycans quantification in biological extracts and its use in skin and muscle tissue studies. *Glycobiology* 13, 647-653

26. Mort, J. S., and Roughley, P. J. (2007) Measurement of glycosaminoglycan release from cartilage explants. *Methods Mol Med* 135, 201-209

27. Bjornsson, S. (1993) Size-dependent separation of proteoglycans by electrophoresis in gels of pure agarose. *Anal Biochem* 210, 292-298

28. Sztrolovics, R., White, R. J., Roughley, P. J., and Mort, J. S. (2002) The mechanism of aggrecan release from cartilage differs with tissue origin and the agent used to stimulate catabolism. *Biochem. J.* 362, 465-472

29. Mwale, F., Demers, C. N., Petit, A., Roughley, P., Poole, A. R., Steffen, T., Aebi, M., and Antoniou, J. (2003) A synthetic peptide of link protein stimulates the biosynthesis of collagens II, IX and proteoglycan by cells of the intervertebral disc. *J Cell Biochem* 88, 1202-1213.31. Mwale, F., Masuda, K., Pichika, R., Epure, L. M., Yoshikawa, T., Hemmad, A., Roughley, P. J., and Antoniou, J. (2011) The efficacy of Link N as a mediator of repair in a rabbit model of intervertebral disc degeneration. *Arthritis Res Ther* 13, R120

32. Wang, Z., Weitzmann, M. N., Sangadala, S., Hutton, W. C., and Yoon, S. T. (2013) Link Protein N-terminal Peptide Binds to Bone Morphogenetic Protein (BMP) Type II Receptor and Drives Matrix Protein Expression in Rabbit Intervertebral Disc Cells. *J Biol Chem* 288, 28243-28253

33. Wang, Z., Hutton, W. C., and Yoon, S. T. (2013) ISSLS Prize winner: Effect of link protein peptide on human intervertebral disc cells. *Spine (Phila Pa. 1976)* 38, 1501-1507

34. Gawri, R., Antoniou, J., Ouellet, J., Awwad, W., Steffen, T., Roughley, P., Haglund, L., and Mwale, F. (2013) Best Paper NASS 2013: Link-N can stimulate proteoglycan synthesis in the degenerated human intervertebral discs. *European cells & materials* 26, 107-119

35. Petit, A., Yao, G., Rowas, S. A., Gawri, R., Epure, L., Antoniou, J., and Mwale, F. (2011) Effect of synthetic link N peptide on the expression of type I and type II collagens in human intervertebral disc cells. *Tissue Eng Part A* 17, 899-904

36. Yang, H., Wu, J., Liu, J., Ebraheim, M., Castillo, S., Liu, X., Tang, T., and Ebraheim, N. A. (2010) Transplanted mesenchymal stem cells with pure fibrinous gelatin-transforming growth factor-beta1 decrease rabbit intervertebral disc degeneration. *Spine J* 10, 802-810

37. Hiyama, A., Mochida, J., Iwashina, T., Omi, H., Watanabe, T., Serigano, K., Tamura, F., and Sakai, D. (2008) Transplantation of mesenchymal stem cells in a canine disc degeneration model. *J Orthop Res* 26, 589-600

38. Sakai, D., Mochida, J., Yamamoto, Y., Nomura, T., Okuma, M., Nishimura, K., Nakai, T., Ando, K., and Hotta, T. (2003) Transplantation of mesenchymal stem cells embedded in Atelocollagen gel to the intervertebral disc: a potential therapeutic model for disc degeneration. *Biomaterials* 24, 3531-3541

39. Vadala, G., Sowa, G., Hubert, M., Gilbertson, L. G., Denaro, V., and Kang, J. D. (2012) Mesenchymal stem cells injection in degenerated intervertebral disc: cell leakage may induce osteophyte formation. *J Tissue Eng Regen Med* 6, 348-355

40. Orozco, L., Soler, R., Morera, C., Alberca, M., Sanchez, A., and Garcia-Sancho, J. (2011) Intervertebral disc repair by autologous mesenchymal bone marrow cells: a pilot study. *Transplantation* 92, 822-828

41. Hristova, G. I., Jarzem, P., Ouellet, J. A., Roughley, P. J., Epure, L. M., Antoniou, J., and Mwale, F. (2011) Calcification in human intervertebral disc degeneration and scoliosis. *J Orthop Res* 29, 1888-1895

42. Nachemson, A., Lewin, T., Maroudas, A., and Freeman, M. A. (1970) In vitro diffusion of dye through the end-plates and the annulus fibrosus of human lumbar intervertebral discs. *Acta Orthop Scand* 41, 589-607

43. Urban, J. P., and Roberts, S. (2003) Degeneration of the intervertebral disc. *Arthritis Res Ther* 5, 120-130

45. Antoniou, J., Epure, L. M., Michalek, A. J., Grant, M. P., Iatridis, J. C., and Mwale, F. (2013) Analysis of quantitative magnetic resonance imaging and biomechanical parameters on human discs with different grades of degeneration. *J Magn Reson Imaging*

46. Majumdar, S., Link, T. M., Steinbach, L. S., Hu, S., and Kurhanewicz, J. (2011) Diagnostic tools and imaging methods in intervertebral disk degeneration. *Orthop Clin North Am* 42, 501-511, viii 47. Borthakur, A., Maurer, P. M., Fenty, M., Wang, C., Berger, R., Yoder, J., Balderston, R. A., and Elliott, D. M. (2011) T1rho magnetic resonance imaging and discography pressure as novel biomarkers for disc degeneration and low back pain. *Spine (Phila Pa. 1976)* 36, 2190-2196

48. Roughley, P. J. (2004) Biology of intervertebral disc aging and degeneration: involvement of the extracellular matrix. *Spine* 29, 2691-2699

49. Antoniou, J., Steffen, T., Nelson, F., Winterbottom, N., Hollander, A. P., Poole, R. A., Aebi, M., and Alini, M. (1996) The human lumbar intervertebral disc: evidence for changes in the biosynthesis and denaturation of the extracellular matrix with growth, maturation, ageing, and degeneration. *J. Clin. Invest.* 98, 996-1003

50. Roberts, S., Evans, E. H., Kletsas, D., Jaffray, D. C., and Eisenstein, S. M. (2006) Senescence in human intervertebral discs. *Eur. Spine J.* 15 Suppl 3, S312-S316

51. Le Maitre, C. L., Freemont, A. J., and Hoyland, J. A. (2005) The role of interleukin-1 in the pathogenesis of human intervertebral disc degeneration. *Arthritis Res. Ther* 7, R732-R745

52. Shamji, M. F., Setton, L. A., Jarvis, W., So, S., Chen, J., Jing, L., Bullock, R., Isaacs, R. E., Brown, C., and Richardson, W. J. (2010) Proinflammatory cytokine expression profile in degenerated and herniated human intervertebral disc tissues. *Arthritis Rheum* 62, 1974-1982

53. Freemont, A. J. (2009) The cellular pathobiology of the degenerate intervertebral disc and discogenic back pain. *Rheumatology.* (Oxford) 48, 5-10

54. Struglics, A., and Hansson, M. (2012) MMP proteolysis of the human extracellular matrix protein aggrecan is mainly a process of normal turnover. *Biochem J* 446, 213-223

55. Gruber, H. E., Ingram, J. A., Hoelscher, G. L., Zinchenko, N., Norton, H. J., and Hanley, E. N., Jr. (2011) Constitutive expression of cathepsin K in the human intervertebral disc: new insight into disc extracellular matrix remodeling via cathepsin K and receptor activator of nuclear factor-kappaB ligand. *Arthritis research & therapy* 13, R140

56. Bachmeier, B. E., Nerlich, A., Mittermaier, N., Weiler, C., Lumenta, C., Wuertz, K., and Boos, N. (2009) Matrix metalloproteinase expression levels suggest distinct enzyme roles during lumbar disc herniation and degeneration. *European spine journal: official publication of the European Spine Society, the European Spinal Deformity Society, and the European Section of the Cervical Spine Research Society* 18, 1573-1586

57. Tiaden, A. N., Klawitter, M., Lux, V., Mirsaidi, A., Bahrenberg, G., Glanz, S., Quero, L., Liebscher, T., Wuertz, K., Ehrmann, M., and Richards, P. J. (2012) Detrimental role for human high temperature requirement serine protease A1 (HTRA1) in the pathogenesis of intervertebral disc (IVD) degeneration. *J Biol Chem* 287, 21335-21345

58. Gruber, H. E., Fisher, E. C., Jr., Desai, B., Stasky, A. A., Hoelscher, G., and Hanley, E. N., Jr. (1997) Human intervertebral disc cells from the annulus: three-dimensional culture in agarose or alginate and responsiveness to TGF-beta1. *Experimental cell research* 235, 13-21

59. Chen, W. H., Lo, W. C., Lee, J. J., Su, C. H., Lin, C. T., Liu, H. Y., Lin, T. W., Lin, W. C., Huang, T. Y., and Deng, W. P. (2006) Tissue-engineered intervertebral disc and chondrogenesis using human nucleus pulposus regulated through TGF-beta1 in platelet-rich plasma. *Journal of cellular physiology* 209, 744-754

60. Hiyama, A., Gogate, S. S., Gajghate, S., Mochida, J., Shapiro, I. M., and Risbud, M. V. (2010) BMP-2 and TGF-beta stimulate expression of beta1,3-glucuronosyl transferase 1 (GlcAT-1) in nucleus pulposus cells through AP1, TonEBP, and Sp1: role of MAPKs. *Journal of bone and mineral research: the official journal of the American Society for Bone and Mineral Research* 25, 1179-1190

61. Jin, H., Shen, J., Wang, B., Wang, M., Shu, B., and Chen, D. (2011) TGF-beta signaling plays an essential role in the growth and maintenance of intervertebral disc tissue. *FEBS letters* 585, 1209-1215

62. Billington, C. J., Mason, P., Magny, M. C., and Mort, J. S. (2000) The slow-binding inhibition of cathepsin K by its propeptide. *Biochem Biophys Res Commun* 276, 924-929

63. Roughley, P., Hoemann, C., DesRosiers, E., Mwale, F., Antoniou, J., and Alini, M. (2006) The potential of chitosan-based gels containing intervertebral disc cells for nucleus pulposus supplementation. *Biomaterials* 27, 388-396

64. Danfelter, M., Onnerfjord, P., and Heinegard, D. (2007) Fragmentation of proteins in cartilage treated with interleukin-1: specific cleavage of type IX collagen by matrix metalloproteinase 13 releases the NC4 domain. *The Journal of biological chemistry* 282, 36933-36941

65. Maldonado, B. A., and Oegema, T. R., Jr. (1992) Initial characterization of the metabolism of intervertebral disc cells encapsulated in microspheres. *Journal of orthopaedic research: official publication of the Orthopaedic Research Society* 10, 677-690

66. Malemud, C. J., Killeen, W., Hering, T. M., and Purchio, A. F. (1991) Enhanced sulfated-proteoglycan core protein synthesis by incubation of rabbit chondrocytes with recombinant transforming growth factor-beta 1. *J Cell Physiol* 149, 152-159

67. Johnson, A. R., and Erdos, E. G. (1977) Metabolism of vasoactive peptides by human endothelial cells in culture. Angiotensin I converting enzyme (kininase II) and angiotensinase. *The Journal of clinical investigation* 59, 684-695

68. Lu, H., Dalgard, C. L., Mohyeldin, A., McFate, T., Tait, A. S., and Verma, A. (2005) Reversible inactivation of HIF-1 prolyl hydroxylases allows cell metabolism to control basal HIF-1. *The Journal of biological chemistry* 280, 41928-41939

69. Wicks, S. J., Lui, S., Abdel-Wahab, N., Mason, R. M., and Chantry, A. (2000) Inactivation of smad-transforming growth factor beta signaling by Ca(2+)-calmodulin-dependent protein kinase II. *Molecular and cellular biology* 20, 8103-8111

70. McKenna, L. A., Liu, H., Sansom, P. A., and Dean, M. F. (1998) An N-terminal peptide from link protein stimulates proteoglycan biosynthesis in human articular cartilage in vitro. *Arthritis and rheumatism* 41, 157-162

71. Abbott, R. D., Purmessur, D., Monsey, R. D., Brigstock, D. R., Laudier, D. M., and Iatridis, J. C. (2013) Degenerative grade affects the responses of human nucleus pulposus cells to link-N, CTGF, and TGFbeta3. *Journal of spinal disorders & techniques* 26, E86-94

72, Kandel, R., Roberts, S., and Urban, J. P. (2008) Tissue engineering and the intervertebral disc: the challenges. *European spine journal: official publication of the European Spine Society, the European Spinal Deformity Society, and the European Section of the Cervical Spine Research Society* 17 Suppl 4, 480-491

73. Ariga, K., Yonenobu, K., Nakase, T., Kaneko, M., Okuda, S., Uchiyama, Y., and Yoshikawa, H. (2001) Localization of cathepsins D, K, and L in degenerated human intervertebral discs. *Spine* (Phila Pa. 1976) 26, 2666-2672

74. Zigler, J. E., Glenn, J., and Delamarter, R. B. (2012) Five-year adjacent-level degenerative changes in patients with single-level disease treated using lumbar total disc replacement with ProDisc-L versus circumferential fusion. *Journal of neurosurgery. Spine* 17, 504-511

75. Ruberte, L. M., Natarajan, R. N., and Andersson, G. B. (2009) Influence of single-level lumbar degenerative disc disease on the behavior of the adjacent segments—a finite element model study. *Journal of biomechanics* 42, 341-348
76. Lund, T., and Oxland, T. R. (2011) Adjacent level disk disease—is it really a fusion disease? *The Orthopedic clinics of North America* 42, 529-541, viii
77 Hayes A J, Benjamin M, Ralphs J R. Extracellular matrix in development of the intervertebral disc. *Matrix Biol* 2001; 20:107-21.
78. Watanabe H, Yamada Y, Kimata K. Roles of aggrecan, a large chondroitin sulfate proteoglycan, in cartilage structure and function. J Biochem (Tokyo) 1998; 124:687-693.
79. Roughley P J. Biology of intervertebral disc aging and degeneration: involvement of the extracellular matrix. Spine. 2004; 29:2691-2699
80. Li X, An H S, Ellman M, Phillips F, Thonar E J, Park D K, et al. Action of fibroblast growth factor-2 on the intervertebral disc. Arthritis Res Ther 2008; 10:R48.
81. Smith L J, Nerurkar N L, Choi K S, Harfe B D, Elliott D M. Degeneration and regeneration of the intervertebral disc: lessons from development. Dis Model Mech. 2011; 14:31-41.
82. Miller J A, Schmatz C, Schultz A B. Lumbar disc degeneration: correlation with age, sex and spine level in 600 autopsy specimens. Spine. 1988; 14:173-178.
83, Masuda K, An HS. Growth factors and the intervertebral disc. Spine J. 2004; 4:330S-340S.
84. An H S, Takegami K, Kamada H, Nguyen C M, Thonar E J, Singh K, Andersson G B, Masuda K. Intradiscal administration of osteogenic protein-1 increases intervertebral disc height and proteoglycan content in the nucleus pulposus in normal adolescent rabbits. Spine. 2005; 30:25-31.
85. Henriksson H B, Svanvik T, Jonsson M, Hagman M, Horn M, Lindahl A, Brisby H. Transplantation of human mesenchymal stems cells into intervertebral discs in a xenogeneic porcine model. Spine. 2009; 34:141-148
86. Sakai D, Mochida J, Iwashina T, Watanabe T, Nakai T, Ando K, Hotta T. Differentiation of mesenchymal stem cells transplanted to a rabbit degenerative disc model: potential and limitations for stem cell therapy in disc regeneration. Spine. 2005; 30:2379-2387.
87. Liu H, McKenna L A, Dean M F. An N-terminal peptide from link protein can stimulate biosynthesis of collagen by human articular cartilage. Arch Biochem Biophys. 2000; 14:116-122.
88. Mwale F, Demers C N, Petit A, Roughley P, Poole A R, Steffen T, Aebi M, Antoniou J. A synthetic peptide of link protein stimulates the biosynthesis of collagens II, IX and proteoglycan by cells of the intervertebral disc. J Cell Biochem. 2003; 14:1202-1213.
89. Tchetina E, Mwale F, Poole A R. Distinct phases of coordinated early and late gene expression in growth plate chondrocytes in relationship to cell proliferation, matrix assembly, remodeling, and cell differentiation. J Bone Miner Res. 2003; 14:844-851.
90. Mwale F, Demers C N, Petit A, Antoniou J. Effect of the N-terminal peptide of Link protein on human mesenchymal stem cells from osteoarthritis patients. J Stem Cells. 2008; 14:99.
91. Li Z, Gunn J, Chen M H, et al. On-site alginate gelation for enhanced cell proliferation and uniform distribution in porous scaffolds. J Biomed Mater Res A 2008; 86:552-9.
92. Lin Y J, Yen C N, Hu Y C, et al. Chondrocytes culture in three-dimensional porous alginate scaffolds enhanced cell proliferation, matrix synthesis and gene expression. J Biomed Mater Res A 2009; 88:23-33.
93. Gawri R, Antoniou J, Ouellet J, Awwad W, Steffen T, Roughley P, Haglund L, Mwale F. Link-N can stimulate proteoglycan synthesis in the degenerated human intervertebral discs. Eur Cells Mater 2013, In Press.
94. Farndale R W, Buttle D J, Barrett A J. Improved quantitation and discrimination of sulphated glycosaminoglycans by use of dimethylmethylene blue. Biochim Biophys Acta 1986; 883:173-7.
95. Mwale F, Ciobanu I, Giannitsios D, Roughley P, Steffen T, Antoniou J. Effect of oxygen levels on proteoglycan synthesis by intervertebral disc cells. Spine 2011; 36(2): E131-8.
96. Alini M, Roughley P J, Antoniou J, Stoll T, Aebi M. A biological approach to treating disc degeneration: not for today, but maybe for tomorrow. Eur Spine J. 2002, Suppl 2:S215-20.
97. Chou A I, Reza A T, Nicoll S B. Distinct intervertebral disc cell populations adopt similar phenotypes in three-dimensional culture. Tissue Eng Part A. 2008; 14(12): 2079-87.
98. Roughley P J, Melching L I, Heathfield T F, Pearce R H, Mort J S. The structure and degradation of aggrecan in human intervertebral disc. Eur Spine J. 2006 Suppl 3:S326-32.

---

The invention claimed is:

1. An isolated polypeptide consisting of a sequence selected from DHLSDNYT (SEQ ID NO: 2) and DHHSDNYT (SEQ ID NO: 3).

2. An isolated nucleic acid that encodes the polypeptide of claim 1.

3. A vector comprising the Isolated nucleic acid of claim 2.

4. A recombinant cell expressing the polypeptide of claim 1.

5. The recombinant cell of claim 4, wherein the cell Is a chondrocyte lineage cell, a stem cell or a disc cell.

6. A pharmaceutical composition comprising the isolated polypeptide of claim 1 and a pharmaceutically acceptable carrier, stabilizing moiety, or diluent.

7. A pharmaceutical composition comprising a scaffold formed of a biocompatible material comprising the isolated polypeptide of claim 1, and a pharmaceutically acceptable carrier, stabilizing moiety, or diluent.

8. A method of inducing matrix synthesis in a cartilage, chondrocyte cell, and/or disc cell or in a tissue comprising a cartilage, chondrocyte cell, and/or disc cell, the method comprising incubating/culturing the cartilage, chondrocyte cell, and/or disc cell with an effective amount of the isolated polypeptide of claim 1 under conditions to induce proteoglycan and collagen synthesis, thus producing an induced cartilage, chondrocyte cell, and/or disc cell with increased matrix synthesis.

9. A method of producing cartilage, chondrocyte cell, and/or disc tissue for implanting into a subject, the method comprising incubating/culturing the cartilage, chondrocyte cell, and/or disc cell with an effective amount of the isolated polypeptide of claim 1 under conditions to induce proteoglycan and collagen synthesis, thus producing an induced cartilage, chondrocyte cell, and/or disc cell with increased matrix synthesis, wherein a substantially pure population of the induced cartilage, chondrocyte cell, and/or disc cell can be isolated.

10. A method of alleviating a symptom and/or treating a cartilage and/or disc disorder, comprising administering to a subject in need thereof the isolated polypeptide of claim 1.

11. The method of claim 10, wherein the cartilage and/or disc disorder is intervertebral disc degeneration or an inflammatory or degenerative joint disease, wherein the inflammatory or degenerative joint disease comprises arthritis, undesirable osteogenesis, and/or calcification condition.

12. A method of alleviating a symptom and/or treating a cartilage and/or disc disorder, comprising administering to a subject in need thereof the recombinant cell of claim 4.

13. A method of alleviating a symptom and/or treating a cartilage and/or disc disorder, comprising administering to a subject in need thereof the pharmaceutical composition of claim 6.

* * * * *